(12) United States Patent
Gill et al.

(10) Patent No.: US 9,072,572 B2
(45) Date of Patent: Jul. 7, 2015

(54) DENTAL LIGHT DEVICE

(71) Applicant: Kerr Corporation, Orange, CA (US)

(72) Inventors: Owen J. Gill, Southbury, CT (US); Ruth Barry, Stoughton, WI (US); Stacy L. Wyatt, Irvine, CA (US); Gopikrishnan Soundararajan, Aliso Viejo, CA (US)

(73) Assignee: Kerr Corporation, Orange, CA (US)

( * ) Notice: Subject to any disclaimer, the term of this patent is extended or adjusted under 35 U.S.C. 154(b) by 0 days.

(21) Appl. No.: 13/924,439

(22) Filed: Jun. 21, 2013

(65) Prior Publication Data

US 2014/0038124 A1 Feb. 6, 2014

Related U.S. Application Data

(63) Continuation-in-part of application No. 12/752,335, filed on Apr. 1, 2010.

(60) Provisional application No. 61/166,130, filed on Apr. 2, 2009.

(51) Int. Cl.
*B60Q 1/06* (2006.01)
*H05B 37/02* (2006.01)
*A61C 13/15* (2006.01)

(52) U.S. Cl.
CPC .............. *A61C 19/004* (2013.01); *H05B 37/02* (2013.01)

(58) Field of Classification Search
CPC ............ A61N 5/06; A61N 2005/0644; A61N 2005/0652; A61C 19/063
USPC ........................................................ 362/373
See application file for complete search history.

(56) References Cited

U.S. PATENT DOCUMENTS

| | | | |
|---|---|---|---|
| 2,218,678 A | 10/1940 | Hoffman | |
| 3,310,358 A | 3/1967 | Marcatili et al. | |
| 3,638,013 A | 1/1972 | Keller | |
| 3,666,180 A | 5/1972 | Coombs et al. | |
| 3,704,928 A | 12/1972 | Coombs et al. | |
| 3,712,984 A | 1/1973 | Lienhard | |
| 3,733,481 A | 5/1973 | Kuyt | |

(Continued)

FOREIGN PATENT DOCUMENTS

| | | |
|---|---|---|
| CA | 2190225 A1 | 6/1997 |
| CA | 2266845 A1 | 10/1999 |

(Continued)

OTHER PUBLICATIONS

Burgess, John O. et al., An Evaluation of Four Light-Curing Units Comparing Soft and Hard Curing, ; Pract. Periodont Aesthet. Dent. 11(1), 125-132, 1999.

(Continued)

*Primary Examiner* — Mary Ellen Bowman
(74) *Attorney, Agent, or Firm* — Wood, Herron & Evans, LLP

(57) ABSTRACT

A light device includes a body and a tip structure configured to be removably coupled with the housing. The tip includes a light engine that is operable for emitting light positioned at a distal end of the tip. A power supply circuit is positioned in the housing and coupled to the light engine. The power supply circuit is rechargeable and includes at least one ultracapacitor element. A non-imaging element is coupled with the light engine at the distal end.

19 Claims, 36 Drawing Sheets

(56) References Cited

U.S. PATENT DOCUMENTS

| | | |
|---|---|---|
| 3,755,900 A | 9/1973 | Friedman |
| 3,787,678 A | 1/1974 | Rainer |
| 3,829,676 A | 8/1974 | Nelson et al. |
| 3,868,513 A | 2/1975 | Gonser |
| 3,930,149 A | 12/1975 | French |
| 3,970,856 A | 7/1976 | Mahaffey et al. |
| 4,032,773 A | 6/1977 | Halliday, Jr. et al. |
| 4,041,304 A | 8/1977 | Spector |
| 4,045,663 A | 8/1977 | Young |
| RE29,421 E | 9/1977 | Scott |
| 4,048,490 A | 9/1977 | Troue |
| 4,080,737 A | 3/1978 | Fleer |
| 4,112,335 A | 9/1978 | Gonser |
| 4,114,274 A | 9/1978 | Jones |
| 4,114,946 A | 9/1978 | Hoffmeister et al. |
| 4,149,086 A | 4/1979 | Nath |
| 4,151,583 A | 4/1979 | Miller |
| 4,184,196 A | 1/1980 | Moret et al. |
| 4,185,891 A | 1/1980 | Kaestner |
| 4,186,748 A | 2/1980 | Schlager |
| 4,209,907 A | 7/1980 | Tsukada et al. |
| 4,221,994 A | 9/1980 | Friedman et al. |
| 4,229,658 A | 10/1980 | Gonser |
| 4,230,453 A | 10/1980 | Reimers |
| 4,233,649 A | 11/1980 | Scheer et al. |
| 4,245,890 A | 1/1981 | Hartman et al. |
| 4,266,535 A | 5/1981 | Moret |
| 4,280,273 A | 7/1981 | Vincent |
| 4,281,366 A | 7/1981 | Wurster et al. |
| 4,298,806 A | 11/1981 | Herold |
| 4,308,120 A | 12/1981 | Pennewiss et al. |
| 4,309,617 A | 1/1982 | Long |
| 4,325,107 A | 4/1982 | MacLeod |
| 4,337,759 A | 7/1982 | Popovich et al. |
| 4,348,180 A | 9/1982 | Schuss |
| 4,357,648 A | 11/1982 | Nelson |
| 4,360,860 A | 11/1982 | Johnson et al. |
| 4,385,344 A | 5/1983 | Gonser |
| RE31,279 E | 6/1983 | Mefferd et al. |
| 4,391,588 A | 7/1983 | Matsui |
| 4,392,827 A | 7/1983 | Martin |
| 4,398,885 A | 8/1983 | Loge et al. |
| 4,402,524 A | 9/1983 | D'Antonio et al. |
| 4,412,134 A | 10/1983 | Herold et al. |
| 4,445,858 A | 5/1984 | Johnson |
| 4,450,139 A | 5/1984 | Bussiere et al. |
| 4,522,594 A | 6/1985 | Stark et al. |
| 4,610,630 A | 9/1986 | Betush |
| 4,611,992 A | 9/1986 | Lokken |
| 4,634,953 A | 1/1987 | Shoji et al. |
| 4,666,405 A | 5/1987 | Ericson |
| 4,666,406 A | 5/1987 | Kanca, III |
| 4,673,353 A | 6/1987 | Nevin |
| 4,682,950 A | 7/1987 | Dragan |
| 4,698,730 A | 10/1987 | Sakai et al. |
| 4,716,296 A | 12/1987 | Bussiere et al. |
| 4,725,231 A * | 2/1988 | Boinot et al. .................. 433/29 |
| 4,729,076 A | 3/1988 | Masami et al. |
| 4,733,937 A | 3/1988 | Lia et al. |
| 4,757,381 A | 7/1988 | Cooper et al. |
| 4,762,862 A | 8/1988 | Yada et al. |
| 4,792,692 A | 12/1988 | Herold et al. |
| 4,794,315 A | 12/1988 | Pederson et al. |
| 4,810,194 A | 3/1989 | Snedden |
| 4,819,139 A | 4/1989 | Thomas |
| 4,826,431 A | 5/1989 | Fujimura et al. |
| 4,835,344 A | 5/1989 | Iyogi et al. |
| 4,836,782 A | 6/1989 | Gonser |
| 4,839,566 A | 6/1989 | Herold et al. |
| 4,846,546 A | 7/1989 | Cuda |
| 4,857,801 A | 8/1989 | Farrell |
| 4,888,489 A | 12/1989 | Bryan |
| 4,935,665 A | 6/1990 | Murata |
| 4,936,808 A | 6/1990 | Lee |
| 4,948,215 A | 8/1990 | Friedman |
| 4,963,798 A | 10/1990 | McDermott |
| 4,992,045 A | 2/1991 | Beisel |
| 4,999,310 A | 3/1991 | Kim |
| 5,003,434 A | 3/1991 | Gonser et al. |
| 5,007,837 A | 4/1991 | Werly |
| 5,013,144 A | 5/1991 | Silverglate et al. |
| 5,013,240 A | 5/1991 | Bailey et al. |
| 5,017,140 A | 5/1991 | Ascher |
| 5,029,957 A | 7/1991 | Hood |
| 5,043,634 A | 8/1991 | Rothwell, Jr. et al. |
| 5,046,810 A | 9/1991 | Steiner et al. |
| 5,063,255 A | 11/1991 | Hasegawa et al. |
| 5,070,258 A | 12/1991 | Izumi et al. |
| 5,071,222 A | 12/1991 | Laakmann et al. |
| 5,115,761 A | 5/1992 | Hood |
| 5,123,845 A | 6/1992 | Vassiliadis et al. |
| 5,139,495 A | 8/1992 | Daikuzono |
| 5,147,204 A | 9/1992 | Patten et al. |
| 5,150,016 A | 9/1992 | Sawase et al. |
| 5,161,879 A | 11/1992 | McDermott |
| 5,162,696 A | 11/1992 | Goodrich |
| 5,173,810 A | 12/1992 | Yamakawa |
| RE34,196 E | 3/1993 | Munro |
| 5,189,751 A | 3/1993 | Giuliani et al. |
| 5,198,678 A | 3/1993 | Oppawsky |
| 5,201,655 A | 4/1993 | Friedman |
| 5,209,169 A | 5/1993 | Basic, Sr. |
| 5,233,283 A | 8/1993 | Kennedy |
| 5,242,602 A | 9/1993 | Richardson et al. |
| 5,265,792 A | 11/1993 | Harrah et al. |
| 5,275,564 A | 1/1994 | Vassiliadis et al. |
| 5,278,629 A | 1/1994 | Schlager et al. |
| 5,283,425 A | 2/1994 | Imamura |
| 5,285,318 A | 2/1994 | Gleckman |
| 5,288,231 A | 2/1994 | Kuehn et al. |
| 5,290,169 A | 3/1994 | Friedman et al. |
| 5,302,124 A | 4/1994 | Lansing et al. |
| 5,312,249 A | 5/1994 | Kennedy |
| 5,316,473 A | 5/1994 | Hare |
| 5,328,368 A | 7/1994 | Lansing et al. |
| 5,346,489 A | 9/1994 | Levy et al. |
| 5,348,552 A | 9/1994 | Nakajima et al. |
| 5,371,826 A | 12/1994 | Friedman |
| 5,373,114 A | 12/1994 | Kondo et al. |
| 5,382,799 A | 1/1995 | May |
| 5,388,988 A | 2/1995 | Goisser et al. |
| 5,395,490 A | 3/1995 | Hoff et al. |
| 5,397,892 A | 3/1995 | Abdelqader |
| 5,415,543 A | 5/1995 | Rozmajzl, Jr. |
| 5,418,384 A | 5/1995 | Yamana et al. |
| 5,420,768 A | 5/1995 | Kennedy |
| 5,448,323 A | 9/1995 | Clark et al. |
| 5,457,611 A | 10/1995 | Verderber |
| 5,471,129 A * | 11/1995 | Mann .................. 340/636.1 |
| 5,475,417 A | 12/1995 | Ogata et al. |
| 5,485,317 A | 1/1996 | Perissinotto et al. |
| 5,487,662 A | 1/1996 | Kipke et al. |
| 5,521,392 A | 5/1996 | Kennedy et al. |
| 5,527,261 A | 6/1996 | Monroe et al. |
| 5,530,632 A | 6/1996 | Shikano et al. |
| 5,535,230 A | 7/1996 | Abe |
| 5,598,005 A | 1/1997 | Wang et al. |
| 5,613,751 A | 3/1997 | Parker et al. |
| 5,616,141 A | 4/1997 | Cipolla |
| 5,617,492 A | 4/1997 | Beach et al. |
| 5,621,303 A | 4/1997 | Shalvi |
| 5,634,711 A * | 6/1997 | Kennedy et al. .............. 362/119 |
| 5,639,158 A | 6/1997 | Sato |
| 5,660,461 A | 8/1997 | Ignatius et al. |
| 5,664,042 A | 9/1997 | Kennedy |
| 5,669,769 A | 9/1997 | Disel |
| 5,678,998 A | 10/1997 | Honkura et al. |
| 5,688,042 A | 11/1997 | Madadi et al. |
| 5,689,866 A | 11/1997 | Kasai et al. |
| 5,698,866 A | 12/1997 | Doiron et al. |
| 5,702,250 A | 12/1997 | Kipke |
| 5,707,139 A | 1/1998 | Haitz |
| 5,711,665 A | 1/1998 | Adam et al. |
| 5,733,029 A | 3/1998 | Monroe |

(56) References Cited

U.S. PATENT DOCUMENTS

| | | |
|---|---|---|
| 5,741,132 A | 4/1998 | Usui et al. |
| 5,747,363 A | 5/1998 | Wei et al. |
| 5,749,724 A | 5/1998 | Cheng |
| 5,759,032 A | 6/1998 | Bartel |
| 5,762,605 A | 6/1998 | Cane et al. |
| 5,766,012 A | 6/1998 | Rosenbaum et al. |
| 5,768,458 A | 6/1998 | Ro et al. |
| 5,772,643 A | 6/1998 | Howell et al. |
| 5,782,552 A | 7/1998 | Green et al. |
| 5,782,553 A | 7/1998 | McDermott |
| 5,791,898 A | 8/1998 | Maissami |
| 5,797,740 A | 8/1998 | Lundvik |
| 5,803,579 A | 9/1998 | Turnbull et al. |
| 5,803,729 A | 9/1998 | Tsimerman |
| 5,807,397 A | 9/1998 | Barreras |
| 5,857,767 A | 1/1999 | Hochstein |
| 5,880,839 A | 3/1999 | Ishizuka et al. |
| 5,882,082 A | 3/1999 | Moore |
| 5,885,082 A | 3/1999 | Levy |
| 5,886,401 A | 3/1999 | Liu |
| 5,897,314 A | 4/1999 | Hack et al. |
| 5,905,268 A | 5/1999 | Garcia et al. |
| 5,908,294 A | 6/1999 | Schick et al. |
| 5,908,295 A | 6/1999 | Kawata |
| 5,912,470 A | 6/1999 | Eibofner et al. |
| 5,921,652 A | 7/1999 | Parker et al. |
| 5,921,777 A | 7/1999 | Dorman |
| 5,928,220 A | 7/1999 | Shimoji |
| 5,928,505 A | 7/1999 | Inakagata et al. |
| 5,931,676 A | 8/1999 | Honkura et al. |
| 5,936,353 A | 8/1999 | Triner et al. |
| 5,971,755 A | 10/1999 | Liebermann et al. |
| 5,975,714 A | 11/1999 | Vetorino et al. |
| 5,975,895 A | 11/1999 | Sullivan |
| 6,001,058 A | 12/1999 | Sano et al. |
| 6,008,264 A | 12/1999 | Ostler et al. |
| 6,019,482 A | 2/2000 | Everett |
| 6,019,493 A | 2/2000 | Kuo et al. |
| 6,019,599 A | 2/2000 | Volcker et al. |
| 6,028,694 A | 2/2000 | Schmidt |
| 6,028,788 A | 2/2000 | Choi et al. |
| 6,033,087 A | 3/2000 | Shozo et al. |
| 6,033,223 A | 3/2000 | Narusawa et al. |
| 6,036,336 A | 3/2000 | Wu |
| 6,045,240 A | 4/2000 | Hochstein |
| 6,046,460 A | 4/2000 | Mertins |
| 6,059,421 A | 5/2000 | White et al. |
| 6,065,965 A | 5/2000 | Rechmann |
| 6,068,474 A | 5/2000 | Senn et al. |
| 6,072,576 A | 6/2000 | McDonald et al. |
| 6,077,073 A | 6/2000 | Jacob |
| 6,079,861 A | 6/2000 | Woodward et al. |
| 6,086,366 A | 7/2000 | Mueller et al. |
| 6,086,367 A | 7/2000 | Levy |
| 6,089,740 A | 7/2000 | Forehand et al. |
| 6,095,661 A | 8/2000 | Lebens et al. |
| 6,095,812 A | 8/2000 | Senn et al. |
| 6,099,520 A | 8/2000 | Shimoji |
| 6,102,696 A | 8/2000 | Osterwalder et al. |
| 6,103,203 A | 8/2000 | Fischer |
| 6,123,545 A | 9/2000 | Eggler et al. |
| 6,132,213 A | 10/2000 | Knorpp et al. |
| 6,155,823 A | 12/2000 | Nagel |
| 6,157,661 A | 12/2000 | Walker et al. |
| 6,159,005 A | 12/2000 | Herold et al. |
| 6,161,937 A | 12/2000 | Rosenstatter |
| 6,168,431 B1 | 1/2001 | Narusawa et al. |
| 6,171,105 B1 | 1/2001 | Sarmadi |
| 6,186,786 B1 | 2/2001 | Trushkowsky |
| 6,190,020 B1 | 2/2001 | Hartley |
| 6,193,510 B1 | 2/2001 | Tsimerman |
| 6,200,134 B1 | 3/2001 | Kovac et al. |
| 6,203,325 B1 | 3/2001 | Honkura et al. |
| 6,208,788 B1 | 3/2001 | Nosov |
| 6,210,042 B1 | 4/2001 | Wang et al. |
| 6,220,722 B1 | 4/2001 | Begemann |
| 6,257,883 B1 | 7/2001 | Voudouris |
| 6,266,576 B1 | 7/2001 | Okada et al. |
| 6,270,343 B1 | 8/2001 | Martin |
| 6,280,187 B1 | 8/2001 | Slone |
| 6,280,188 B1 | 8/2001 | Ross |
| 6,282,013 B1 | 8/2001 | Ostler et al. |
| 6,299,450 B1 | 10/2001 | Honkura et al. |
| 6,318,996 B1 | 11/2001 | Melikechi et al. |
| 6,322,358 B1 | 11/2001 | Senn et al. |
| 6,325,623 B1 | 12/2001 | Melnyk et al. |
| 6,328,456 B1 | 12/2001 | Mize |
| 6,331,111 B1 | 12/2001 | Cao |
| 6,345,982 B1 | 2/2002 | Meyer |
| 6,361,192 B1 | 3/2002 | Fussell et al. |
| 6,361,489 B1 | 3/2002 | Tsai |
| 6,371,826 B1 | 4/2002 | Pestonji |
| 6,379,149 B1 | 4/2002 | Franetzki |
| 6,382,967 B1 | 5/2002 | Rohner et al. |
| 6,384,099 B1 | 5/2002 | Ostler et al. |
| 6,398,398 B1 | 6/2002 | Moschkowitz |
| 6,402,511 B1 | 6/2002 | Calderwood |
| 6,417,917 B1 | 7/2002 | Jung et al. |
| 6,419,483 B1 | 7/2002 | Adam et al. |
| 6,425,761 B1 | 7/2002 | Eibofner |
| 6,439,888 B1 | 8/2002 | Boutoussov et al. |
| 6,444,725 B1 | 9/2002 | Trom et al. |
| 6,454,789 B1 | 9/2002 | Chen et al. |
| 6,465,961 B1 | 10/2002 | Cao |
| 6,468,077 B1 | 10/2002 | Melikechi et al. |
| 6,478,447 B2 | 11/2002 | Yen |
| 6,482,004 B1 | 11/2002 | Senn et al. |
| 6,485,301 B1 | 11/2002 | Gemunder et al. |
| 6,498,108 B2 | 12/2002 | Cao et al. |
| 6,511,317 B2 | 1/2003 | Melikechi et al. |
| 6,511,321 B1 | 1/2003 | Trushkowsky et al. |
| 6,514,075 B1 | 2/2003 | Jacob |
| 6,522,086 B2 | 2/2003 | Gemunder et al. |
| 6,528,555 B1 | 3/2003 | Nikutowski et al. |
| 6,554,463 B2 | 4/2003 | Hooker et al. |
| 6,558,048 B2 | 5/2003 | Kuhara et al. |
| 6,558,829 B1 | 5/2003 | Faris et al. |
| 6,561,802 B2 | 5/2003 | Alexander |
| 6,561,806 B2 | 5/2003 | Kyotani et al. |
| 6,563,269 B2 | 5/2003 | Robinett et al. |
| 6,604,847 B2 | 8/2003 | Lehrer |
| 6,611,110 B1 | 8/2003 | Fregoso |
| 6,634,770 B2 | 10/2003 | Cao |
| 6,634,771 B2 | 10/2003 | Cao |
| 6,635,363 B1 | 10/2003 | Duclos et al. |
| 6,638,063 B2 | 10/2003 | Otsuka |
| 6,666,612 B2 | 12/2003 | Lorigny et al. |
| 6,692,251 B1 | 2/2004 | Logan et al. |
| 6,692,252 B2 | 2/2004 | Scott |
| 6,692,525 B2 | 2/2004 | Brady et al. |
| 6,695,614 B2 | 2/2004 | Plank |
| 6,700,158 B1 | 3/2004 | Cao et al. |
| 6,702,576 B2 | 3/2004 | Fischer et al. |
| 6,709,128 B2 | 3/2004 | Gordon et al. |
| 6,709,270 B2 | 3/2004 | Honkura et al. |
| 6,719,446 B2 | 4/2004 | Cao |
| 6,719,558 B2 | 4/2004 | Cao |
| 6,719,559 B2 | 4/2004 | Cao |
| 6,746,885 B2 | 6/2004 | Cao |
| 6,755,647 B2 | 6/2004 | Melikechi et al. |
| 6,755,648 B2 | 6/2004 | Cao |
| 6,755,649 B2 | 6/2004 | Cao |
| 6,764,719 B2 | 7/2004 | Russell et al. |
| 6,767,109 B2 | 7/2004 | Plank et al. |
| 6,780,010 B2 | 8/2004 | Cao |
| 6,783,362 B2 | 8/2004 | Cao |
| 6,783,810 B2 | 8/2004 | Jin et al. |
| 6,793,490 B2 | 9/2004 | Bianchetti et al. |
| 6,799,967 B2 | 10/2004 | Cao |
| 6,815,241 B2 | 11/2004 | Wang |
| 6,821,119 B2 | 11/2004 | Shortt et al. |
| 6,824,294 B2 | 11/2004 | Cao |
| 6,829,260 B2 | 12/2004 | Hsia et al. |
| 6,832,849 B2 | 12/2004 | Yoneda et al. |

(56) References Cited

U.S. PATENT DOCUMENTS

| | | |
|---|---|---|
| 6,835,219 B2 | 12/2004 | Gittleman |
| 6,857,873 B2 | 2/2005 | Bianchetti et al. |
| 6,873,111 B2 | 3/2005 | Ito et al. |
| 6,880,954 B2 | 4/2005 | Ollett et al. |
| 6,880,985 B2 | 4/2005 | Hoshino et al. |
| 6,890,175 B2 | 5/2005 | Fischer et al. |
| 6,890,234 B2 | 5/2005 | Bortscheller et al. |
| 6,910,886 B2 | 6/2005 | Cao |
| 6,918,762 B2 | 7/2005 | Gill et al. |
| 6,926,524 B2 | 8/2005 | Cao |
| 6,929,472 B2 | 8/2005 | Cao |
| 6,932,600 B2 | 8/2005 | Cao |
| 6,933,702 B2 | 8/2005 | Hsu |
| 6,940,659 B2 | 9/2005 | McLean et al. |
| 6,951,623 B2 | 10/2005 | Wu |
| 6,953,340 B2 | 10/2005 | Cao |
| 6,954,270 B2 | 10/2005 | Ostler et al. |
| 6,955,537 B2 | 10/2005 | Cao |
| 6,957,907 B2 | 10/2005 | Fischer et al. |
| 6,969,253 B2 | 11/2005 | Cao |
| 6,971,875 B2 | 12/2005 | Cao |
| 6,971,876 B2 | 12/2005 | Cao |
| 6,974,319 B2 | 12/2005 | Cao |
| 6,976,841 B1 | 12/2005 | Osterwalder |
| 6,979,193 B2 | 12/2005 | Cao |
| 6,979,194 B2 | 12/2005 | Cao |
| 6,981,867 B2 | 1/2006 | Cao |
| 6,981,876 B2 | 1/2006 | Bleckley et al. |
| 6,986,782 B2 | 1/2006 | Chen et al. |
| 6,988,890 B2 | 1/2006 | Cao |
| 6,988,891 B2 | 1/2006 | Cao |
| 6,991,356 B2 | 1/2006 | Tsimerman et al. |
| 6,991,456 B2 | 1/2006 | Plank |
| 6,994,546 B2 | 2/2006 | Fischer et al. |
| 6,994,551 B2 | 2/2006 | Wang et al. |
| 7,001,057 B2 | 2/2006 | Plank et al. |
| 7,011,519 B2 | 3/2006 | Castellini |
| 7,029,277 B2 | 4/2006 | Gofman et al. |
| 7,056,116 B2 | 6/2006 | Scott et al. |
| 7,066,732 B2 | 6/2006 | Cao |
| 7,066,733 B2 | 6/2006 | Logan et al. |
| 7,074,040 B2 | 7/2006 | Kanca |
| 7,077,648 B2 | 7/2006 | Cao |
| 7,086,111 B2 | 8/2006 | Hilscher et al. |
| 7,086,858 B2 | 8/2006 | Cao |
| 7,094,054 B2 | 8/2006 | Cao |
| 7,097,364 B2 | 8/2006 | Wang |
| 7,101,072 B2 | 9/2006 | Takada et al. |
| 7,104,793 B2 * | 9/2006 | Senn et al. ............. 433/29 |
| 7,106,523 B2 | 9/2006 | McLean et al. |
| 7,108,504 B2 | 9/2006 | Cao |
| 7,118,563 B2 | 10/2006 | Weckwerth et al. |
| 7,119,515 B2 | 10/2006 | Senn et al. |
| 7,134,875 B2 | 11/2006 | Oxman et al. |
| 7,139,580 B2 | 11/2006 | Stein et al. |
| 7,144,250 B2 | 12/2006 | Fischer et al. |
| 7,153,015 B2 | 12/2006 | Brukilacchio |
| 7,163,181 B2 | 1/2007 | Omps |
| 7,163,318 B2 | 1/2007 | Panagotacos et al. |
| 7,167,824 B2 | 1/2007 | Kallulli |
| 7,178,941 B2 | 2/2007 | Roberge et al. |
| 7,179,860 B2 | 2/2007 | Cao et al. |
| 7,182,597 B2 | 2/2007 | Gill et al. |
| 7,189,983 B2 | 3/2007 | Aguirre et al. |
| 7,192,276 B2 | 3/2007 | Fischer et al. |
| 7,195,482 B2 | 3/2007 | Scott |
| 7,202,489 B2 | 4/2007 | Aguirre et al. |
| 7,202,490 B2 | 4/2007 | Aguirre et al. |
| 7,207,694 B1 | 4/2007 | Petrick |
| 7,210,814 B2 | 5/2007 | Scott et al. |
| 7,210,930 B2 | 5/2007 | Kovac et al. |
| 7,223,270 B2 | 5/2007 | Altshuler et al. |
| 7,224,001 B2 | 5/2007 | Cao |
| 7,250,611 B2 | 7/2007 | Aguirre et al. |
| 7,252,678 B2 | 8/2007 | Ostler et al. |
| 7,267,457 B2 | 9/2007 | Ostler et al. |
| 7,267,546 B2 | 9/2007 | Scott et al. |
| 7,271,420 B2 | 9/2007 | Cao |
| 7,273,369 B2 | 9/2007 | Rosenblood et al. |
| 7,283,230 B2 | 10/2007 | Ostler et al. |
| 7,294,364 B2 | 11/2007 | Cao |
| 7,300,175 B2 | 11/2007 | Brukilacchio |
| 7,320,593 B2 | 1/2008 | Ostler et al. |
| 7,323,849 B1 | 1/2008 | Robinett et al. |
| 7,329,887 B2 | 2/2008 | Henson et al. |
| 7,410,283 B2 | 8/2008 | West et al. |
| 7,422,598 B2 | 9/2008 | Altshuler et al. |
| 7,443,133 B2 | 10/2008 | Hamada et al. |
| 7,452,924 B2 | 11/2008 | Aasen et al. |
| 7,471,068 B2 | 12/2008 | Cegnar |
| 7,483,504 B2 | 1/2009 | Shapira et al. |
| 7,485,116 B2 | 2/2009 | Cao |
| 7,507,491 B2 | 3/2009 | Finkelshtain et al. |
| 7,530,707 B2 | 5/2009 | Plank et al. |
| 7,530,808 B2 | 5/2009 | Cao et al. |
| 7,624,467 B2 | 12/2009 | Hilscher et al. |
| 7,645,056 B1 | 1/2010 | Mills et al. |
| 7,645,086 B2 | 1/2010 | Zhang et al. |
| 7,651,268 B2 | 1/2010 | Cao et al. |
| 7,654,086 B2 | 2/2010 | Gong et al. |
| 7,661,172 B2 | 2/2010 | Hilscher et al. |
| 7,677,888 B1 | 3/2010 | Halm |
| 7,677,890 B2 | 3/2010 | Turner |
| 7,696,728 B2 | 4/2010 | Cross et al. |
| 7,704,074 B2 | 4/2010 | Jensen |
| 7,712,468 B2 | 5/2010 | Hargadon |
| 7,728,345 B2 | 6/2010 | Cao |
| 7,733,056 B2 | 6/2010 | Hartung et al. |
| 7,758,204 B2 | 7/2010 | Klipstein et al. |
| 7,786,499 B2 | 8/2010 | Cao |
| 7,861,363 B2 | 1/2011 | Moll et al. |
| 7,976,211 B2 | 7/2011 | Cao |
| 7,989,839 B2 | 8/2011 | Dahm |
| 7,995,882 B2 | 8/2011 | Wanninger et al. |
| 8,019,405 B2 | 9/2011 | Weber et al. |
| 8,096,691 B2 | 1/2012 | Mills et al. |
| 8,113,830 B2 | 2/2012 | Gill et al. |
| 8,174,209 B2 | 5/2012 | Bayer et al. |
| 8,203,281 B2 | 6/2012 | Cegnar et al. |
| 8,231,383 B2 | 7/2012 | Gill et al. |
| 8,269,469 B2 | 9/2012 | Cegnar et al. |
| 8,333,588 B2 | 12/2012 | Putz et al. |
| 8,337,097 B2 | 12/2012 | Cao |
| 8,568,140 B2 | 10/2013 | Kovac et al. |
| 8,569,785 B2 | 10/2013 | Cao |
| 8,602,774 B2 | 12/2013 | Wasyluscha |
| 8,653,723 B2 | 2/2014 | Cao et al. |
| 2001/0007739 A1 | 7/2001 | Eibofner et al. |
| 2002/0093833 A1 | 7/2002 | West |
| 2002/0168607 A1 | 11/2002 | Cao |
| 2003/0015667 A1 | 1/2003 | MacDougald et al. |
| 2003/0036031 A1 | 2/2003 | Lieb et al. |
| 2003/0060013 A1 | 3/2003 | Marchant et al. |
| 2003/0081430 A1 | 5/2003 | Becker |
| 2003/0147258 A1 | 8/2003 | Fischer et al. |
| 2003/0148242 A1 | 8/2003 | Fischer et al. |
| 2003/0152885 A1 | 8/2003 | Dinh |
| 2003/0186195 A1 | 10/2003 | Comfort et al. |
| 2003/0215766 A1 | 11/2003 | Fischer et al. |
| 2003/0235800 A1 | 12/2003 | Qadar |
| 2004/0029069 A1 * | 2/2004 | Gill et al. ............. 433/29 |
| 2004/0054386 A1 | 3/2004 | Martin et al. |
| 2004/0101802 A1 | 5/2004 | Scott |
| 2004/0117930 A1 | 6/2004 | Townley et al. |
| 2004/0120146 A1 | 6/2004 | Ostler et al. |
| 2004/0152038 A1 | 8/2004 | Kumagai et al. |
| 2004/0181154 A1 | 9/2004 | Peterson et al. |
| 2004/0185413 A1 * | 9/2004 | Gill et al. ............. 433/29 |
| 2004/0214131 A1 | 10/2004 | Fischer et al. |
| 2004/0256630 A1 | 12/2004 | Cao |
| 2005/0002975 A1 | 1/2005 | Cao |
| 2005/0033119 A1 | 2/2005 | Okawa et al. |
| 2005/0074723 A1 | 4/2005 | Ostler et al. |
| 2005/0077865 A1 | 4/2005 | Durbin et al. |

(56) References Cited

U.S. PATENT DOCUMENTS

| | | |
|---|---|---|
| 2005/0082989 A1 | 4/2005 | Jones et al. |
| 2005/0096661 A1 | 5/2005 | Farrow et al. |
| 2005/0099824 A1 | 5/2005 | Dowling et al. |
| 2005/0154081 A1 | 7/2005 | Yin et al. |
| 2005/0158687 A1 | 7/2005 | Dahm |
| 2005/0171408 A1 | 8/2005 | Parker |
| 2005/0174753 A1 | 8/2005 | Cao et al. |
| 2005/0174801 A1 | 8/2005 | Cao |
| 2005/0196721 A1 | 9/2005 | Jackson et al. |
| 2005/0282102 A1 | 12/2005 | Kert |
| 2006/0033052 A1 | 2/2006 | Scott |
| 2006/0040231 A1 | 2/2006 | Quan et al. |
| 2006/0044823 A1 | 3/2006 | Wong et al. |
| 2006/0084028 A1 | 4/2006 | Cheetham et al. |
| 2006/0084717 A1 | 4/2006 | Cohen et al. |
| 2006/0095095 A1 | 5/2006 | Cao |
| 2006/0188835 A1 | 8/2006 | Nagel et al. |
| 2006/0188836 A1 | 8/2006 | Logan et al. |
| 2006/0199144 A1 | 9/2006 | Liu et al. |
| 2006/0240375 A1 | 10/2006 | Soukos et al. |
| 2006/0252005 A1 | 11/2006 | Feinbloom et al. |
| 2006/0271068 A1 | 11/2006 | Cao |
| 2006/0274529 A1 | 12/2006 | Cao |
| 2006/0275732 A1 | 12/2006 | Cao |
| 2006/0275733 A1 | 12/2006 | Cao |
| 2007/0020578 A1 | 1/2007 | Scott et al. |
| 2007/0025658 A1 | 2/2007 | Fukai et al. |
| 2007/0031777 A1 | 2/2007 | Wang et al. |
| 2007/0037113 A1 | 2/2007 | Scott et al. |
| 2007/0054232 A1 | 3/2007 | Rauchenzauner |
| 2007/0128577 A1 | 6/2007 | Scott et al. |
| 2007/0170444 A1 | 7/2007 | Cao |
| 2007/0224570 A1 | 9/2007 | West et al. |
| 2007/0228392 A1 | 10/2007 | Plank et al. |
| 2007/0265607 A1 | 11/2007 | Cao et al. |
| 2007/0279011 A1 | 12/2007 | Jones et al. |
| 2008/0026103 A1 | 1/2008 | Fichtali et al. |
| 2008/0027518 A1 | 1/2008 | Island et al. |
| 2008/0071256 A1 | 3/2008 | Cao et al. |
| 2008/0080184 A1 | 4/2008 | Cao |
| 2008/0086117 A1 | 4/2008 | Cao |
| 2008/0154249 A1 | 6/2008 | Cao |
| 2008/0191941 A1 | 8/2008 | Saban et al. |
| 2008/0225019 A1 | 9/2008 | Hsiung |
| 2008/0285302 A1 | 11/2008 | Scott et al. |
| 2008/0311545 A1 | 12/2008 | Ostler et al. |
| 2008/0315829 A1 | 12/2008 | Jones et al. |
| 2009/0011385 A1 | 1/2009 | Jensen et al. |
| 2009/0087393 A1 | 4/2009 | Jensen et al. |
| 2009/0092947 A1 | 4/2009 | Cao et al. |
| 2009/0143842 A1 | 6/2009 | Cumbie et al. |
| 2009/0147505 A1 | 6/2009 | Robinett |
| 2009/0155740 A1 | 6/2009 | Jensen et al. |
| 2009/0208894 A1* | 8/2009 | Orloff et al. .................. 433/29 |
| 2009/0227875 A1 | 9/2009 | Cao et al. |
| 2009/0238779 A1 | 9/2009 | Jensen et al. |
| 2009/0271936 A1 | 11/2009 | Walanski et al. |
| 2009/0315484 A1* | 12/2009 | Cegnar et al. ................ 315/307 |
| 2010/0004640 A1 | 1/2010 | Cao et al. |
| 2010/0117560 A1 | 5/2010 | Cao |
| 2010/0173267 A1 | 7/2010 | Cao et al. |
| 2010/0207502 A1 | 8/2010 | Cao et al. |
| 2010/0273123 A1 | 10/2010 | Mecher |
| 2011/0070553 A1* | 3/2011 | Stempfle et al. ............. 433/29 |
| 2011/0143304 A1 | 6/2011 | Jamnia et al. |
| 2012/0230017 A1 | 9/2012 | Duffy |
| 2014/0038125 A1 | 2/2014 | Logan et al. |
| 2014/0051031 A1 | 2/2014 | Kovac et al. |

FOREIGN PATENT DOCUMENTS

| | | |
|---|---|---|
| CA | 2298993 A1 | 9/2000 |
| DE | 2315709 A1 | 10/1974 |
| DE | 2842938 A1 | 4/1980 |
| DE | 3411996 A1 | 10/1985 |
| DE | 3706852 A1 | 10/1987 |
| DE | 9017070 U1 | 4/1992 |
| DE | 4211233 A1 | 8/1993 |
| DE | 29511927 U1 | 1/1997 |
| DE | 19624087 | 12/1997 |
| DE | 19624087 | 12/1997 |
| DE | 19803755 A1 | 8/1999 |
| EP | 000266038 A2 | 5/1988 |
| EP | 000320080 A1 | 6/1989 |
| EP | 0531438 A1 | 3/1993 |
| EP | 000568666 A1 | 11/1993 |
| EP | 000591613 A1 | 4/1994 |
| EP | 000672435 A1 | 9/1995 |
| EP | 000678282 A2 | 10/1995 |
| EP | 000709698 A1 | 5/1996 |
| EP | 000736307 A2 | 10/1996 |
| EP | 000740567 A1 | 11/1996 |
| EP | 000750889 A1 | 1/1997 |
| EP | 000755662 A1 | 1/1997 |
| EP | 000780101 A2 | 6/1997 |
| EP | 000780103 A2 | 6/1997 |
| EP | 000830850 A1 | 3/1998 |
| EP | 000830851 A1 | 3/1998 |
| EP | 000830852 A1 | 3/1998 |
| EP | 0879582 | 11/1998 |
| EP | 000879582 A2 | 11/1998 |
| EP | 000880945 A2 | 12/1998 |
| EP | 000884025 A1 | 12/1998 |
| EP | 000885025 A1 | 12/1998 |
| EP | 000959803 A1 | 12/1999 |
| EP | 000998880 A2 | 5/2000 |
| EP | 001031326 A1 | 8/2000 |
| EP | 001090607 A1 | 4/2001 |
| EP | 001090608 A1 | 4/2001 |
| EP | 001093765 A2 | 4/2001 |
| EP | 001103232 A1 | 5/2001 |
| EP | 001112721 A1 | 7/2001 |
| EP | 001138276 A1 | 10/2001 |
| EP | 001138349 A2 | 10/2001 |
| EP | 001206923 A1 | 5/2002 |
| EP | 001228738 A1 | 8/2002 |
| EP | 001253547 A2 | 10/2002 |
| EP | 001374797 A1 | 1/2004 |
| EP | 001843079 A2 | 10/2007 |
| EP | 2058636 A2 | 5/2009 |
| GB | 002212010 A | 7/1989 |
| GB | 002218636 A | 11/1989 |
| GB | 002329756 A | 3/1999 |
| GB | 002385137 A | 8/2003 |
| JP | 7240536 | 9/1985 |
| JP | 8141001 | 6/1996 |
| JP | H06285508 A | 6/1996 |
| JP | 910238 | 1/1997 |
| JP | 928719 | 4/1997 |
| JP | 9187825 | 7/1997 |
| JP | 1033573 | 2/1998 |
| JP | 10245245 | 9/1998 |
| JP | 11267140 | 1/1999 |
| JP | 2000312688 | 11/2000 |
| JP | 2001522635 | 11/2001 |
| JP | 2002125984 | 5/2002 |
| JP | 2002320683 | 5/2002 |
| JP | 2002200100 | 7/2002 |
| JP | 2003093405 | 4/2003 |
| JP | 2003524501 A | 8/2003 |
| JP | 2003288201 | 10/2003 |
| JP | 2004040998 A | 2/2004 |
| JP | 2004355852 | 12/2004 |
| JP | 2005168231 A | 6/2005 |
| JP | 2006149190 A | 6/2006 |
| JP | 2007509669 A | 4/2007 |
| JP | 2007128667 | 5/2007 |
| JP | 2007514454 | 6/2007 |
| JP | 2007516689 A | 6/2007 |
| JP | 2011135973 A | 7/2011 |
| WO | 8301311 | 4/1983 |
| WO | 8404463 | 11/1984 |
| WO | 9202275 | 2/1992 |

(56) References Cited

FOREIGN PATENT DOCUMENTS

| | | |
|---|---|---|
| WO | 9309847 | 5/1993 |
| WO | 9321842 | 11/1993 |
| WO | 9507731 | 3/1995 |
| WO | 9519810 | 7/1995 |
| WO | 9526217 | 10/1995 |
| WO | 9736552 | 10/1997 |
| WO | 9737722 | 10/1997 |
| WO | 1997039880 A2 | 10/1997 |
| WO | 9746279 | 12/1997 |
| WO | 9746280 | 12/1997 |
| WO | 9803131 | 1/1998 |
| WO | 9803132 | 1/1998 |
| WO | 9804317 | 2/1998 |
| WO | 9836703 | 8/1998 |
| WO | 9909071 | 2/1999 |
| WO | 9911324 | 3/1999 |
| WO | 9916136 | 4/1999 |
| WO | 9920346 | 4/1999 |
| WO | 9935995 | 7/1999 |
| WO | 9937239 | 7/1999 |
| WO | 0002491 | 1/2000 |
| WO | 0013608 | 3/2000 |
| WO | 0014012 | 3/2000 |
| WO | 0015296 | 3/2000 |
| WO | 0041726 | 7/2000 |
| WO | 0041767 | 7/2000 |
| WO | 0041768 | 7/2000 |
| WO | 0043067 | 7/2000 |
| WO | 0043068 | 7/2000 |
| WO | 0043069 A1 | 7/2000 |
| WO | 2000043069 A1 | 7/2000 |
| WO | 0045733 A1 | 8/2000 |
| WO | 2000045733 A1 | 8/2000 |
| WO | 0067048 A2 | 11/2000 |
| WO | 0067660 A1 | 11/2000 |
| WO | 2000067048 A2 | 11/2000 |
| WO | 2000067660 A1 | 11/2000 |
| WO | 0103770 A1 | 1/2001 |
| WO | 2001003770 A1 | 1/2001 |
| WO | 0119280 A1 | 3/2001 |
| WO | 2001019280 A1 | 3/2001 |
| WO | 0124724 A1 | 4/2001 |
| WO | 2001024724 A1 | 4/2001 |
| WO | 0154770 A1 | 8/2001 |
| WO | 0160280 A1 | 8/2001 |
| WO | 2001054770 A1 | 8/2001 |
| WO | 2001060280 A1 | 8/2001 |
| WO | 0164129 A1 | 9/2001 |
| WO | 0168035 A2 | 9/2001 |
| WO | 0169691 A1 | 9/2001 |
| WO | 2001064129 A1 | 9/2001 |
| WO | 2001068035 A2 | 9/2001 |
| WO | 2001069691 A1 | 9/2001 |
| WO | 0206723 A1 | 1/2002 |
| WO | 2002006723 A1 | 1/2002 |
| WO | 0209610 A1 | 2/2002 |
| WO | 0211640 A2 | 2/2002 |
| WO | 2002009610 A1 | 2/2002 |
| WO | 2002011640 A2 | 2/2002 |
| WO | 0232505 A1 | 4/2002 |
| WO | 0233312 A2 | 4/2002 |
| WO | 2002032505 A1 | 4/2002 |
| WO | 2002033312 A2 | 4/2002 |
| WO | 0249721 A1 | 6/2002 |
| WO | 2002049721 A1 | 6/2002 |
| WO | 02056787 A2 | 7/2002 |
| WO | 2002056787 A2 | 7/2002 |
| WO | 02069839 A1 | 9/2002 |
| WO | 2002069839 A1 | 9/2002 |
| WO | 02080808 A1 | 10/2002 |
| WO | 2002080808 A1 | 10/2002 |
| WO | 03083364 A1 | 10/2003 |
| WO | 2003083364 A1 | 10/2003 |
| WO | 2005006818 | 1/2005 |
| WO | 2005043709 A1 | 5/2005 |
| WO | 2006014363 A2 | 2/2006 |
| WO | 2006014597 A1 | 2/2006 |
| WO | 2009134885 A1 | 11/2009 |
| WO | 2010029519 A2 | 3/2010 |
| WO | 2010115082 A1 | 10/2010 |

OTHER PUBLICATIONS

Davidson-Kaban, Saliha S. et al., The Effect of Curing Light Variations on Bulk Curing and Wall-to-Wall Quality of Two Types and Various Shades of Resin Composites, ; Dent. Mater. 13: 344-352, Nov. 1997.

Feltzer, A. J. et al., Influence of Light Intensity on Polymerization Shrinkage and Integrity of Restoration-Cavity Interface, Eur. J. Oral Sciences, 103: 322-326, 1995.

Kanca, III, John and Suh, Byoung I., Pulse Activation: Reducing Resin-Based Composite Contraction Stresses at the Enamel Cavosurface Margins, Am. J. of Dentistry, 12(3), 107-112, 1999.

Kato, Hiromasa, Relationship Between the Velocity of Polymerization and Adaptation to Dentin Cavity Wall of Light-Cured Composite, Dental Materials J. 6(1): 32-37, 1987.

Koran, Peter and Kurschner, Ralf, Effect of Sequential versus Continuous Irradiation of a Light-Cured Resin Composite on Shsrinkage, Viscosity, Adhesion, and Degree of Polymerization, Am. J. of Dentistry, 11, No. 1, 17-22, 1998.

LumiLeds Lighting LLC, Luxeon™ Power Light Sources of the Future, Jan. 2001—Mike Holt.

LumiLeds Lighting LLC, Application Note 1149-5, Secondary Optics Design Considerations for Super Flux LEDs, Copyright© 2000 LumiLeds Lighting, Obsoletes Publication No. 5968-1215E, Publication No. ANO6 (3/O0).

LumiLeds Lighting LLC, LED Application Note Dental Light Curing, LumiLeds Lighting Publication No. XXX(03.01), Copyright© 2000.

LumiLeds Lighting LLC, Concept Evaluation Data Luxeon™ Star 5-Watt, Luxeon™ 5-Watt Prelminary Target Data Sheet, Publication No. JP10 (Jan. 2002).

LumiLeds Lighting LLC, Application Bulletin AB XXX, Luxeon™ Data Sheet, Publication No. xxxx-xxxx.

LumiLeds Lighting LLC, Lumen Maintenance of White Luxeon™ Power Light Sources, Application Brief AB07, LumiLeds Lighting, US LLC.

Luxeon Dental Technical Data, Power Light Source, ; Apr. 2002.

Mayes, Joe H., Curing Lights: An Overview, Unknown, p. 15-17.

Mehl, et al., Softstartpolymerisation von Kompositen in Klasse-V-Kavitatent, Dtsch Zhnarzl Z. 52/1997, pp. 824-827 (in German).

Mehl, A. et al., Physical Properties and Gap Formation of Light-Cured Composites With and Without 'Softstart-Polymerization', J. of Dentistry, 25, 321-330, 1997.

Mehl, et al., 496 The Influence of Pre-Curing on the Material Properties of Composite Resins, Journal of Dental Research, vol. 74, 1995, Special Issues S.462 (abstract).

Mehl, et al., Soft Start Polymerization of Composites in Class V Cavities, Dtsch Zhnarztl Z. 52/1997, pp. 824-827.

Mills, Robin W., et al., Blue LED's for Curing Polymer-Based Dental Filling Materials, LEO's Newsletter, Jun. 1998.

Mills, R. W., et al., Optical Power Outputs, Spectra and Dental Composite Depths of Cure, Obtained with Blue Light Emitting Diode (LED and Halogen Light Curing Units (LCU's), Oct. 26, 2002.

Reinhardt, et al., Unischerheiten bei der Prufung von Photopolymerisation, Dtsch zahnarzl Z. 36,635-640, 1981 (in German).

Reinhardt, et al, Uncertaintaies ini the Testing of Photopolymers, Dtsch zahnarzl Z. 635-640, 1981 (English Translation of cite No. 5 above).

Sakaguchi, Ronald L. and Berge, Hong Xu, ; Sakaguchi & Berge, Reduced Light Energy Density Decreases Post-Gel Contraction While Maintaining Degree of Conversion in Composites, J. of Dentistry, 26, 695-700, 1998.

(56) References Cited

OTHER PUBLICATIONS

Schlager, Kenneth J., Ignatius, Ronald W., ; An LED-Array Light Source for Medical Therapy, ; SPIE vol. 1892 Medical Lasers and Systems II (1993) p. 26-35.
Swift Jr., Edward J. et al., Ed., Contemporary Photocuring Issues, Part II, J. Esthetic Dentistry, 12 (1), 50-57, 2000.
Tarle, Z. et al., The Effect of the Photopolymerization Method on the Quality of Composite Resin Samples, ; J. of Oral Rehab. 25: 436-442, 1998.
TIR Technologies, Inc., Miniaturized TIR lenses for Light Emitting Diodes, TIR Technical Publication, pp. 1-14, 1992.
Uno, Shigeru and Asmussen, Erik, Marginal Adaptation of a Restorative Resin Polymerized at Reduced Rate, ; Scand J. Dent. Res. 1991; 99: 440-4.
Seventeen-Page International Search Report mailed Sep. 20, 2010 for International Application No. PCT/US2010/029756.
George W. Gaines, Lieutenant Colonel, USAF, DC & Curtis D. Wyrauch, Major, USAG, DC, A New Generation of Visible—Light Curing Units, USAF School of Aerospace Medicine, Final Report for Period Oct. 1987-Sep. 1988.
Thirteen—Page European Search Report mailed Nov. 21, 2014 for European Patent Application No. EP14172118.

* cited by examiner

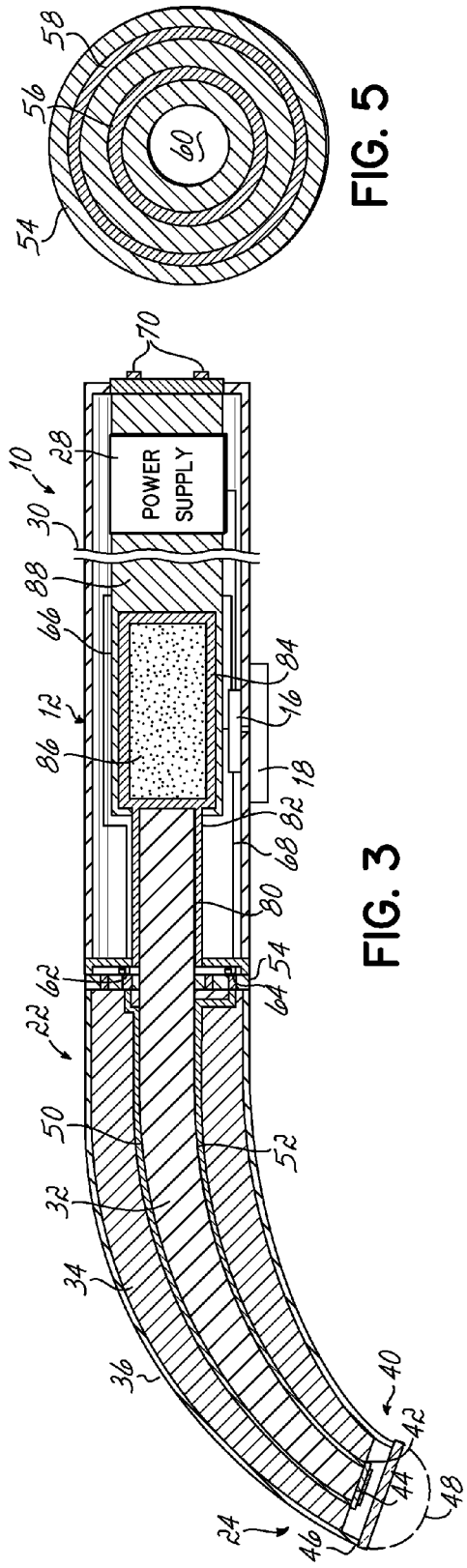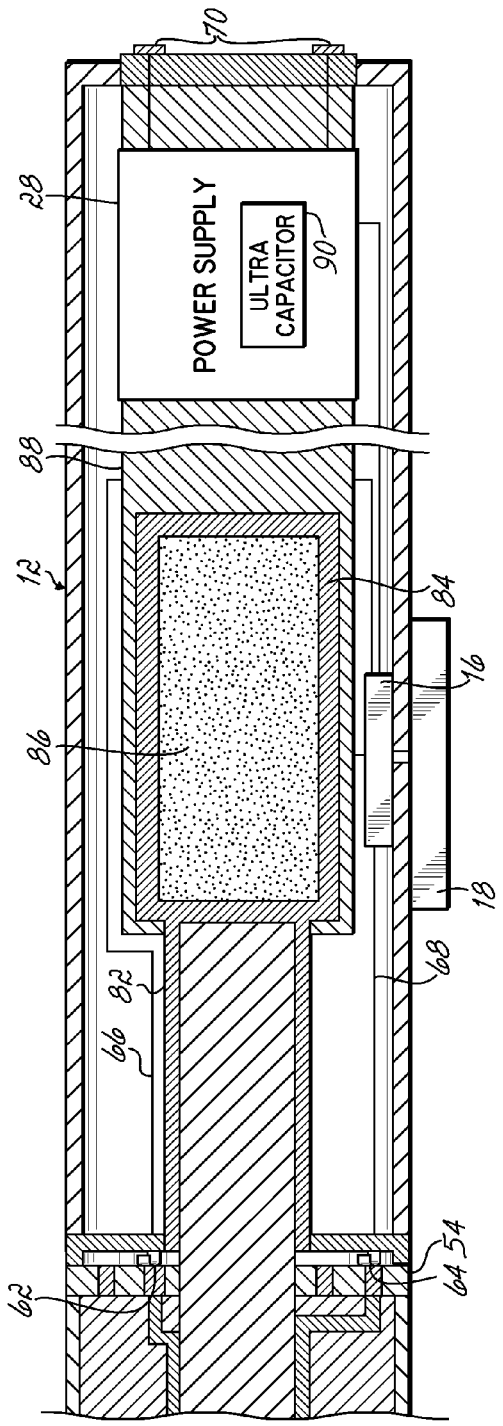

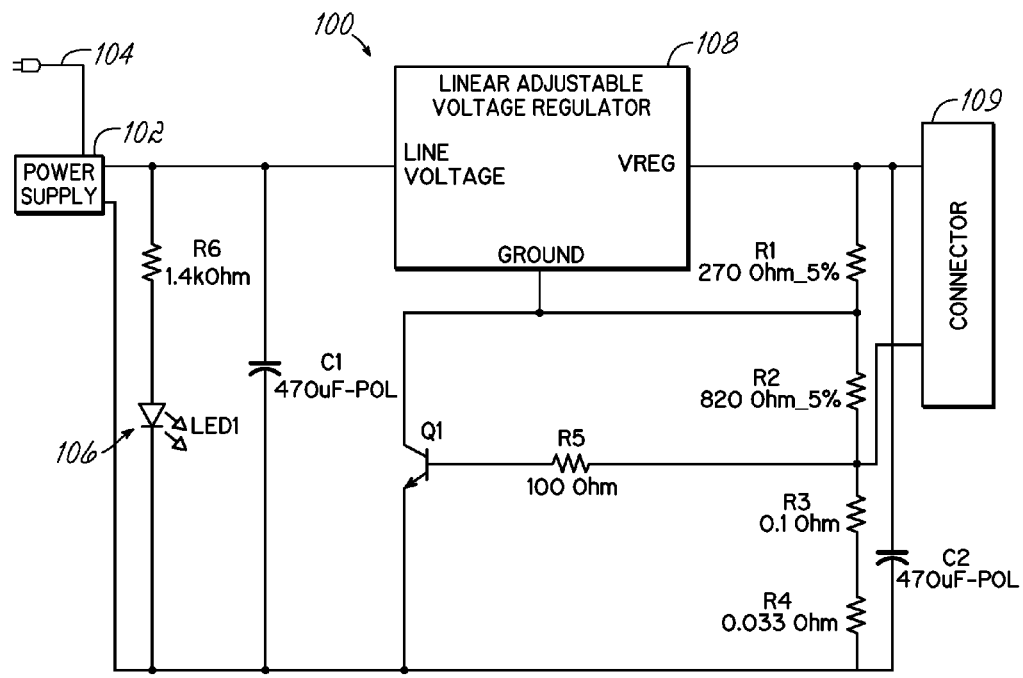
FIG. 6
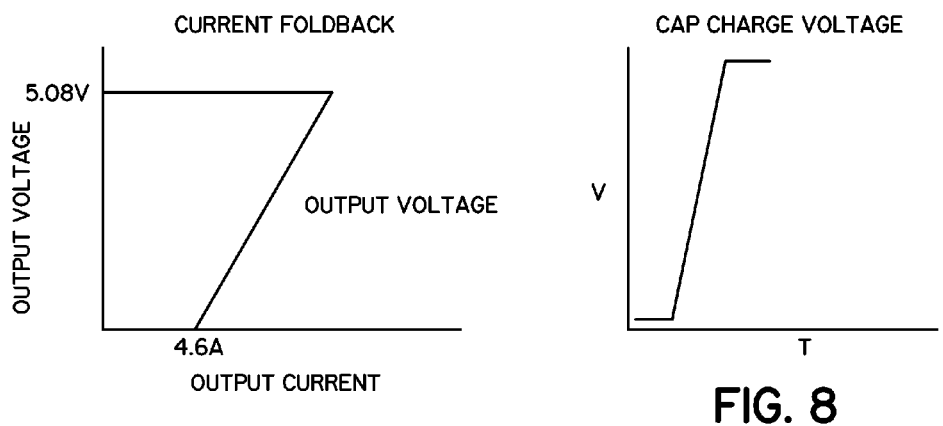
FIG. 7
FIG. 8

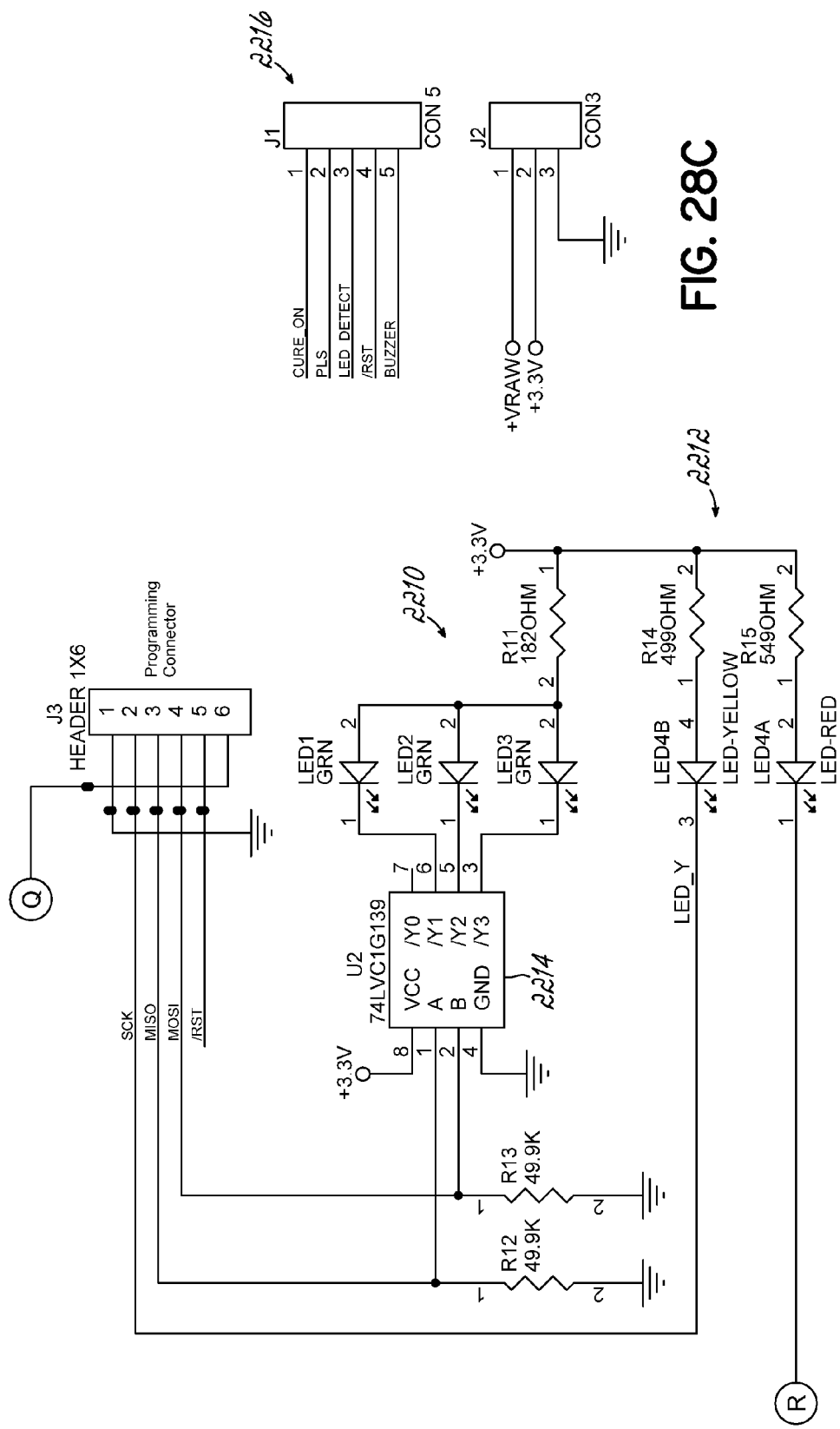

DENTAL LIGHT DEVICE

RELATED APPLICATIONS

This Application is a continuation-in-part Application of U.S. Ser. No. 12/752,335, filed Apr. 1, 2010, and entitled "CURING LIGHT DEVICE", which is a non-provisional application of U.S. Provisional Application No. 61/166,130, filed Apr. 2, 2009, and entitled "CURING LIGHT DEVICE", which applications are incorporated herein by reference in their entireties.

FIELD OF THE INVENTION

This invention relates to illumination or light devices, and more specifically to an illumination device that is used for oral and dental applications and provides light to illuminate and to cure light-curable compounds in dental applications

BACKGROUND OF THE INVENTION

Many illumination devices or light devices exist for use in dental and oral applications. One specific category of dental illumination devices is directed to hand-held devices that are held in proximity to the mouth of the patient to illuminate an area within the patient's mouth for various reasons. One particular usage is directed to curing light-curable compounds in the mouth. While suitable hand-held light devices exist for dental applications, there are often various drawbacks associated with such light devices, particularly with respect to dental curing lights.

Many such dental lights have a body, which contains the light elements, such as light-emitting diodes (LED). A tapered and curved light guide, then interfaces with the end of the body and the light-emitting elements to capture the light and direct it where desired. Generally, such light guides are bundles of fiber-optic elements, which operate to capture the light in the device, away from the patient's mouth, and then forward that light to a tip that may be placed at the area of interest within a patient's mouth. While such light guides operate in a suitable manner, they are also very inefficient. Almost half of the light generated in the device is lost in the transmission from its source down to the tip, through the light guide. Such inefficiency requires a significantly large light engine to generate the light needed at the curing site, such as for curing a compound. In turn, heat is generated, which must be properly removed and directed away from the light engine. The greater the output required by the light engine, the more heat that must be addressed.

Another issue associated with such dental lights is their sterilization. As may be appreciated, the tip of the dental light is generally brought into proximity or into actual contact with the mouth of the patient or some portion of the mouth. Thus, the tip of the light device is exposed to various germs and bacteria. Accordingly, in order to prevent the propagation of germs or infection between patients, dental instruments are often sterilized, such as by being autoclaved at a very high temperature. While suggestions and some attempts have been made in the art to move the light engine of a dental light closer to the operating tip, such attempts have not thoroughly addressed the issue of sterilization. For example, the temperature at which autoclaving is achieved is potentially damaging to a light engine, such as the light-emitting elements in an LED array. Accordingly, the issue of sterilization has not been adequately addressed by existing dental lights, such as dental curing lights.

Another drawback to existing dental lights is directed to their need for a power source. Often times, such lights are actually plugged into a base that then couples to an AC source, such as a wall outlet. Some are connected directly to an AC wall outlet. Some portable dental light devices are not attached to a base, but rather utilize batteries, such as rechargeable batteries. However, rechargeable batteries require a significant amount of time to charge, and thus, there may be some valuable down time required for the dental light, when it might otherwise be put to use. Furthermore, existing battery charging technology uses batteries that are subject to a somewhat limited number of charge cycles. Their continued ability to take and maintain a charge is reduced over time and usage. After a somewhat limited number of cycles, the batteries have to be replaced. Thus, there is still a need to address power issues in portable curing lights.

As such, various drawbacks remain in the field of dental lights, particularly dental curing lights, which are not addressed by the current art.

BRIEF DESCRIPTION OF THE DRAWINGS

FIG. 3 is a side cross-sectional view of the light device of FIG. 1 showing the tip structure engaging the housing.

FIG. 4 is a partial cross-sectional view of an alternative embodiment of the light device of the invention.

FIG. 5 is a plan view of an end cap structure for a tip structure of the invention.

FIG. 6 is a circuit schematic for a charging circuit to be used to charge the invented light device.

FIG. 7 is a graphical depiction of the curve for operation of the circuit of FIG. 7.

FIG. 8 is a graphical depiction of the charging of the ultracapacitors according to an embodiment of the invention.

DETAILED DESCRIPTION OF THE DRAWINGS

The accompanying drawings, which are incorporated in and constitute a part of this specification, illustrate embodiments of the invention and, together with a general description of the invention given below, serve to explain the principles of the invention.

Figure 1:
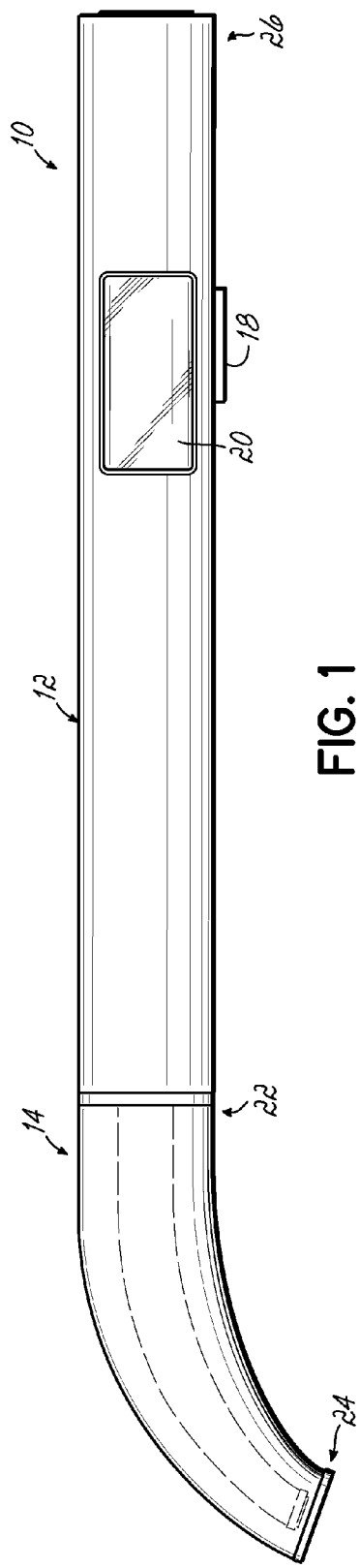
FIG. 1 is a side view of a light device incorporating features of the present invention.
Figure 1A:
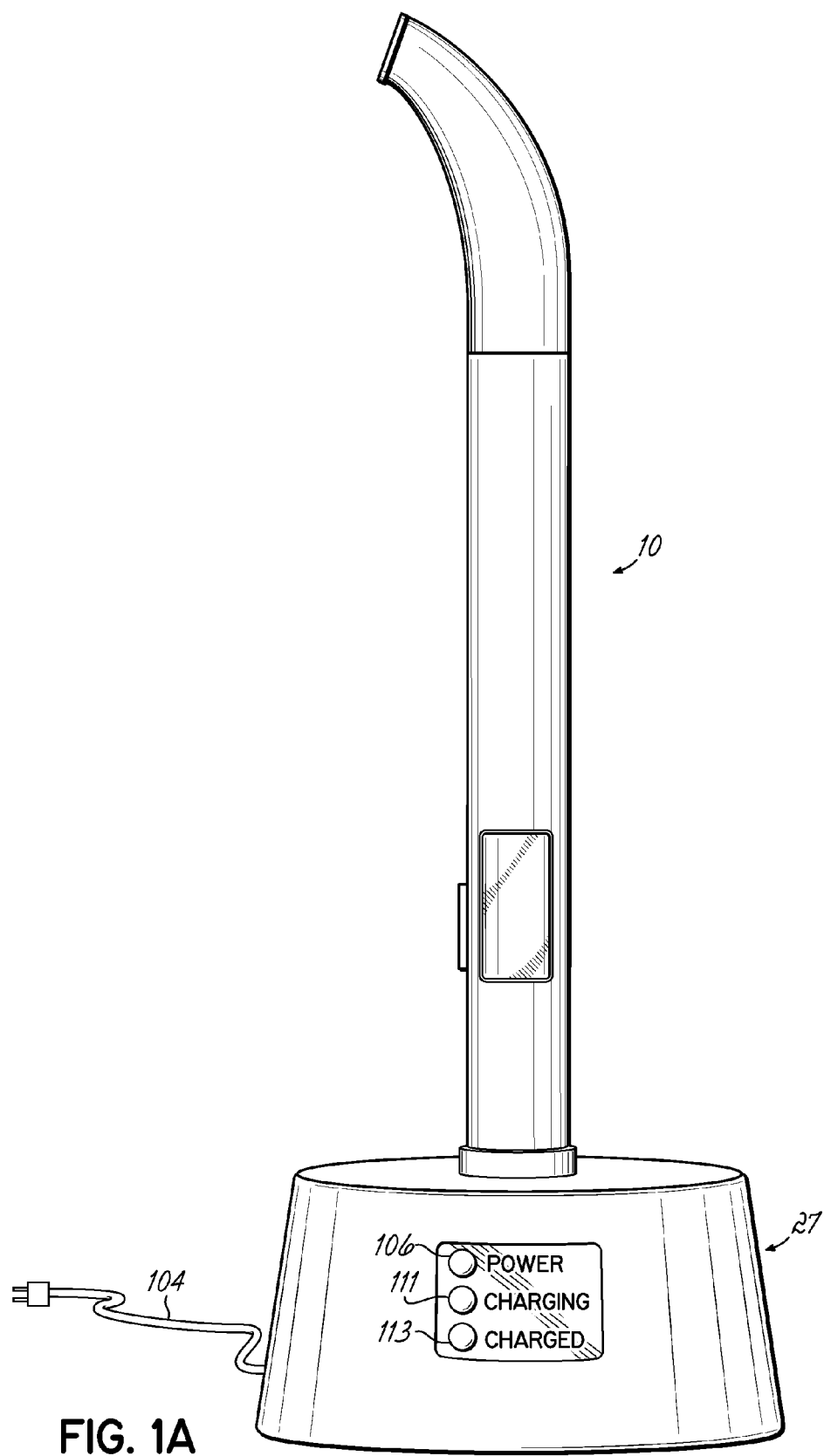
FIG. 1A is a perspective view of a light device in a charging base.

FIG. 1 illustrates one embodiment of a light device 10 of the present invention. While one embodiment of light device 10 might be used for curing, other uses are also anticipated, such as illumination, tooth whitening, or other treatment applications. Thus, the present invention is not limited to the particular use described herein for an exemplary embodiment. Curing device 10 includes the housing 12 and a tip structure 14 that is removably coupled to the housing 12. In accordance with one aspect of the invention, as discussed further hereinbelow, the tip structure 14 may be removed so that it may be separately autoclaved from the overall device. Device 10 also includes suitable control electronics 16 (See FIG. 2) with external controls 18 that may include buttons, switches, or other suitable manual controls for controlling device 10. A display device 20 might also be utilized and may include a screen, individual light elements, or other graphical elements for providing a visual display of the operation of device 10. For example, the operational mode or setting of the device, the selectable curing times, the remaining curing time, the charging or power status, and diagnostic graphics might also be illustrated utilizing a visual display 20. The tip structure 14 includes a proximal end 22 that is removably coupled with housing 12, and a distal end 24, which is placed within the mouth of a patient for curing a light-curable compound, in accordance with the invention. The base 26 of housing 12 might be coupled to a suitable external power supply, such as an AC or DC source in the form of a charging base or dock 27, as shown in FIG. 1A, for charging rechargeable internal elements of power supply circuit 28 of the device 10 (See FIG. 2). Base 26 might also be configured to fit within a suitable structure, such as a standalone, table-mounted base, a mounting structure for mounting it on a wall, pole, or chair, or might be incorporated in a portion of a dental chair for holding and charging the curing device 10.

Figure 2:
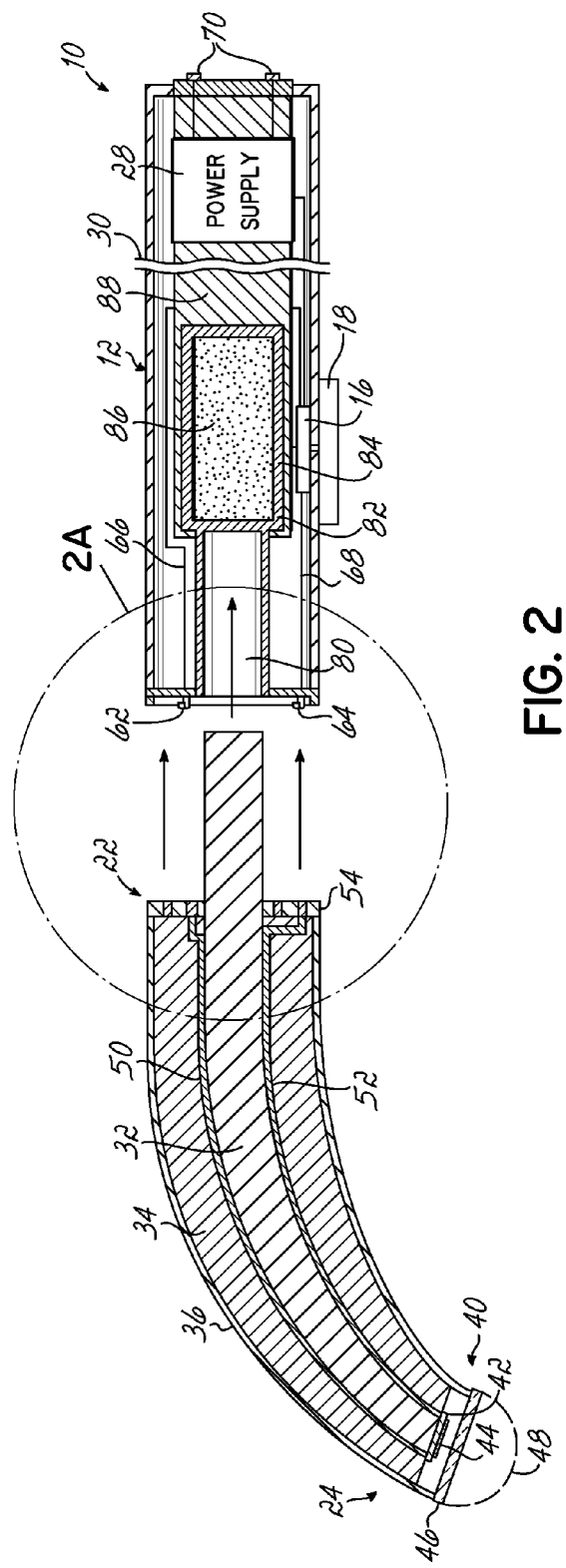
FIG. 2 is an exploded cross-sectional view of the light device of FIG. 1.
Figure 2A:
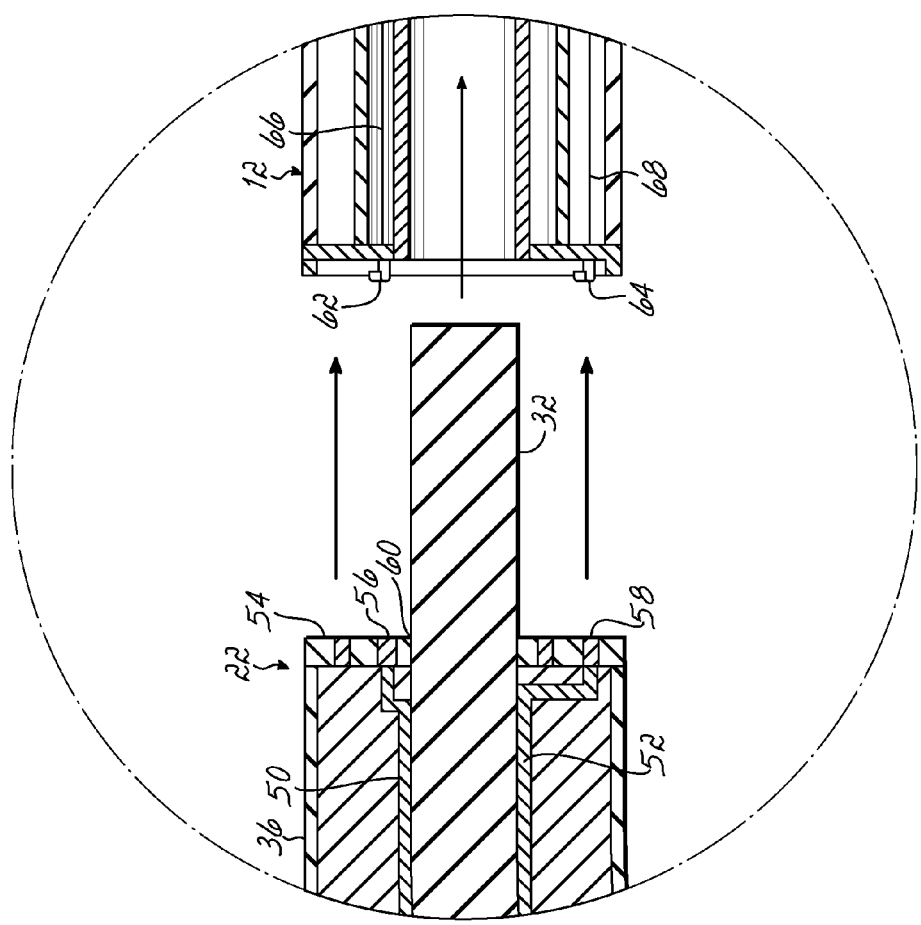
FIG. 2A is an enlarged view of a portion of FIG. 2.

FIGS. 2 and 2A illustrate cross-sectional views of device 10, showing the interface between the tip structure 14 and housing 12.

FIG. 3 illustrates the tip structure 14 engaging the housing. In the figures, section lines 30 are shown indicating a removable portion of the housing 12 for illustrative purposes. The housing 12, as well as the tip structure 14, may be sized as appropriate for a hand-held curing device that may be manipulated to position the distal end 24 of the device in the mouth of a patient, or otherwise proximate to light-curable material and compounds.

Tip structure 14 includes a heat sink structure or element 32 that extends in the tip structure from the proximal end 22 to the distal end 24. In one embodiment of the invention, as illustrated in FIGS. 2 and 2A, the heat sink 32 extends past the proximal end 22 of the tip structure 14 to engage the housing 12 for appropriate thermal transfer of heat from a curing light device. The heat sink may be made from a suitable heat-transfer or heat-conducting material, such as a metal (e.g. copper) or aluminum. Alternatively, a high thermal conductivity material such as Pyrolytic Graphite sheets (PGS) might be used for heat sink 32. In one embodiment, the heat sink 32 is an elongated copper tube formed in an appropriate shape for positioning inside the tip structure 14. Suitable thermal insulation material 34 surrounds the heat sink 32. Tip structure 14 includes a body 36 that houses the elements of the tip structure, and is appropriately sealed at its proximal and distal ends 22 and 24, as discussed further hereinbelow. The body 36 is made from an autoclavable material in accordance with one aspect of the invention. As noted above, it is desirable to sterilize certain reusable dental elements, such as those that are used in or inserted into or onto or proximate to the mouth of a patient. Past curing light devices have not been autoclavable to the degree desired by dental professionals. The present invention provides the tip structure enclosed within a sealed body 36 made from an autoclavable material that is able to withstand high temperature autoclaving, such as above 121° C., thus making the entire tip structure, including the light-emitting device or engine therein, autoclavable as well.

In one embodiment of the invention, the autoclavable body 36 is formed of a suitable metal, such as stainless steel. Alternatively, the body 36 might be formed of a ceramic, glass, or porcelain material that is able to withstand the temperatures associated with autoclaving. Generally, the body 36 will be formed to a suitable shape in conjunction with the heat sink 32 and insulation material 34. For example, the heat sink 32 and insulation material 34 might be formed and the body 36 then formed by coating with the ceramic, glass porcelain, polymeric, or other autoclavable material. In the embodiment illustrated in the figures, the tip structure 14 is appropriately curved from manipulation at a curing site, such as the mouth of a patient, and thus, the body 36 is formed in a curved fashion as well.

Coupled at the distal end of the heat sink 32 is a light-emitting device, or light-emitting engine 40. Such light-emitting devices may include one or more LED elements that are known for curing light-curable compounds, such as dental compounds, and are available from various manufacturers.

High power LED elements are one suitable type of elements for the inventive device. For example, a high-power dental LED might be used. The light-emitting engine might use a single LED element or a plurality of elements in an array. Generally, for curing purposes, the light-emitting device will emit a light in a particular desired wavelength for curing a light-curable compound. For various dental compounds, a suitable light is in the wavelength range of 370-500 nanometers, or the blue light range. For other uses of the inventive light, such as for examination of the oral regions to detect caries, illuminate areas, and provide cancer screening, other wavelengths might be used.

However, in accordance with another aspect of the invention, various different tip structures 14 may be readily removed and inserted into the housing 12 so that multiple different tip structures might be utilized with a single housing 12. To that end, the light-emitting devices of the various tip structures might be directed to other applications, such as to whiten teeth, or for illumination within the mouth of a patient, but would still be operated with the same housing 12 and its controls. As such, the present invention is not limited to a specific type of lighting device or use, and various different tip structures 14 might be utilized with light-emitting devices that emit light in an appropriate range of wavelengths for different uses, such as curing, whitening, illuminating, screening, etc.

Such light-emitting devices or light engine 40 generally include a base or substrate 42 that supports one or more light-emitting structures, or semi-conductor junctions, such as in the form of light-emitting diodes or LEDs. A single light-emitting structure might be utilized or an array of structures might be arranged on substrate 42 for providing device 40, depending upon the power of the structures or elements. High power LED elements may be used for example. The light-emitting device 40 is able to withstand high temperatures, and thus, utilizes high-temperature structures, or LED's. Substrate 42 is adhered directly to the distal end of heat sink 32 utilizing a high-temperature adhesive or cement. The direct coupling of the light-emitting device 40 to the heat sink 32 provides optimum thermal coupling for removal of the heat generated by the light-emitting structures 44 or substrate 42.

To seal the distal end 24 of housing 36, a glass window 46 or other transparent element is solder-sealed around its periphery to housing 36, as shown in FIGS. 2 and 3. The transparent element is configured to allow light to pass out of the distal end of the housing. To that end, the glass window 46 might include metalized portions around its periphery for proper solder-sealing to the housing 36 utilizing a high-temperature solder, or other appropriate high-temperature adhesive. Generally, the light-emitting device 40 operates with a lens 48 over the LEDs or other light-emitting structures in order to focus the light from those structures. A window 46 is illustrated in FIG. 2. Alternatively, a separate lens 48 might be sealed to the end of the housing 36 instead of a window 46. The lens 48 may be appropriately shaped for focusing light from light-emitting device 40. For example, a total internal reflective (TIR) lens might be used, as discussed further hereinbelow for the lens 48.

To power the light-emitting device 40, the present invention utilizes high-temperature flexible circuits, or flex circuits 50, 52. The flex circuits extend generally along the inside of the tip structure proximate the heat sink 32. The flex circuits are flexible, and thus, may follow the contour or shape of the heat sink 32. In one embodiment of the invention, suitable traces or channels might be formed in the heat sink 32 for placement of the flex circuits 50, 52. The flex circuits 50, 52, in turn, couple to a ceramic end cap 54, with suitable electrically-conductive elements, such as traces, thereon for coupling to the flex circuits, and ultimately to a power supply and control circuits, as discussed further below.

Referring now to FIG. 2A, the proximal end 22 of the tip structure 14, and particularly the proximal end of housing 36, is sealed utilizing a ceramic end cap 54 that has rotational circuit traces 56, 58 formed therein, as illustrated in FIG. 5. Specifically, in one particular feature of the invention, the tip structure 14 is rotatably coupled with housing 12. To facilitate such rotation, while maintaining the delivery of electrical signals to the light-emitting device 40, device 10 of the invention incorporates circular electrically-conductive elements or circuit traces 56, 58 formed on or in the end cap 54. As illustrated in FIG. 5, the circuit traces 56, 58 generally follow the shape of the end cap, and have a generally circular shape. Furthermore, end cap 54 has an appropriate center opening 60 formed therein for passage of the heat sink 32, as illustrated in FIG. 2A. As illustrated in FIG. 2A, the innermost circuit trace 56 is illustrated is being electrically-coupled to the flex circuit 50. Similarly, the outer circuit trace 58 on the end cap 54 is coupled with flex circuit 52. End cap 54 may be a ceramic end cap of a suitable ceramic material, such as aluminum oxide. The ceramic cap may be adhered to the body 36. If the body is metal, the edge of ceramic cap 54 may be metalized for soldering the cap to the end of the body. Alternatively, if the body is made from glass, a suitable high-temperature adhesive might be utilized to couple the end cap to the glass body.

As illustrated in FIGS. 2A and 5, the metal traces 56, 58 are formed through end cap 54 to present a connection for the flex circuits at the distal end of the tip structure. When coupled with or plugged into housing 12, as illustrated in FIG. 2A, the flex circuits 50, 52 via the ceramic end cap 54 are coupled to a suitable power supply circuit and controls. Specifically, spring contacts 62, 64 are mounted at the end of housing 12 that interfaces with tip structure 14. Those spring contacts 62, 64 are coupled through appropriate connections or circuits 66, 68 back to a suitable power supply circuit 28. The supplied power may then be controlled via suitable control circuit 16, such as to control the intensity of the light-emitting device, the duration of its illumination, and various other parameters associated with the operational modes of device 10. Housing 12 contains suitable control circuitry 16 and a power supply circuit 28, along with the various electrical connections/circuits 66, 68 for powering the tip structure 14 and the light-emitting device 40 at its distal end. Power supply circuit 28, through contacts 70 may be coupled to an external supply of power, such as an AC source or a DC source, for charging elements of the power supply. For example, as is illustrated in FIG. 1A, a base 27 might hold or dock device 10 for recharging purposes. In one embodiment of the invention, the power supply circuit includes rechargeable supply elements, such as a battery, which may be charged and removed from the external power source to be manipulated by an operator. In an alternative embodiment of the invention, as discussed below with respect to FIG. 4, an ultracapacitor element or circuit might be utilized to provide the desired power for the light-emitting device 40. Housing 12 may be formed of any suitable material, such as plastic or metal, or some other rigid material.

As illustrated in FIG. 3, when the tip structure 14 is coupled to housing 12, the contacts 62, 64 engage the circuit elements or traces 56, 58 respectively in the end of the tip structure. This electronically couples the light-emitting device with the power supply circuit. Because of the unique circular pattern of the traces, the tip structure 14 may be rotated in a range of 0°-360°, while the contacts 62, 64 still maintain connection to the traces 56, 58. Alternatively, the circular conductive element might only be contacted over some circular range less than 360°, but still allow at least partial rotation. In that way, the tip structure may be rotated without jeopardizing the electrical connection between the housing 12 and the tip structure 14. Although the electrically-conductive elements 56, 58 are illustrated as formed on the tip structure and the contact elements 62, 64, as positioned on the housing, their relative position might be reversed with elements 56, 58 on housing 12 and elements 62, 64 on tip structure 14. That is, the electrically-conductive elements or traces 56, 58 and contact elements 62, 64 may be positioned on either of the opposing housing and tip structure to pass power between the two. In an alternative embodiment, alternate pins and sockets might be used between the housing and tip structure to electrically couple the light-emitting device and power supply circuit.

At the same time, the proximal end of the heat sink 32 engages a suitable channel 80 formed in housing 12. The channel 80 is formed by an additional or secondary heat sink structure or element 82, which is preferably formed of a suitable metal, such as aluminum. In addition to the channel 80, the heat sink 82 includes a reservoir portion 84, which contains additional heat sink material. That reservoir portion might be all metal to form a metal heat sink. In accordance with one embodiment of the invention, the reservoir portion 84 might be made of metal, but then contains an amount of phase change material 86. Phase change material absorbs the heat from the secondary heat sink structure 82, and changes phase upon such absorption. For example, one suitable phase change material might be a paraffin wax that melts as it absorbs heat. This allows a suitable delay in the temperature rise of the light-emitting device 40 to provide a safe temperature level for the light-emitting device and the overall tip structure during normal usage. Other phase change materials might also be contained within the reservoir portion 84 of the secondary heat sink structure 82, and thus, the present invention is not limited to a particular phase change material 86.

As illustrated in FIG. 3, when the tip structure 14 is plugged into, or otherwise coupled to or engaged with, housing 12, the heat sink 32 engages the secondary heat sink structure 82 such that the end of the heat sink 32 is inserted into channel 80 to provide direct thermal connection or coupling between the heat sink 32 and the secondary heat sink structure 82. In that way, the metal of the secondary heat sink structure 82 may absorb the heat conducted by heat sink 32. If the reservoir portion 84 is simply solid metal or filled with a metal material, that metal would absorb heat, and thus, keep the temperature of the light-emitting device at a suitable operating point. Alternatively, if the phase change material 86 fills reservoir 84, the phase change material may melt in its absorption of heat, and thus, change phase to keep the operating point at a suitably low temperature. The circuits 66, 68 are high temperature circuits, and thus, will be suitable in their proximity to the secondary heat sink structure 82. Furthermore, a jacket of insulation 88 might surround a proportion of the secondary heat sink structure 82, such as the reservoir portion 84, and may also surround suitable electronic elements, such as the power supply circuit 28, and portions of the contacts 70 in order to protect them from the heat of the second heat sink structure 82.

Solid-liquid phase change materials absorb heat, and their temperature rises to a point where they change phase (their melting point). The materials then absorb additional amounts of heat without getting significantly hotter. When the ambient temperature in the reservoir provided by the secondary heat sink drops, the phase change material 86 solidifies, and thus, releases its stored heat. Therefore, the phase change material absorbs and emits heat while maintaining a generally constant temperature, which is desirable for the hand-held housing 12.

Another suitable phase change material is paraffin wax loaded with carbon. Once the heat sink engages with the bore hole, or channel 80 of the external heat sink, suitable thermal conduction is achieved.

The spring-loaded nature of the spring contacts 62, 64 provides a consistent and robust electrical connection between housing 12 and the tip structure 14.

Turning to FIG. 4, in accordance with another embodiment of the present invention, the power supply circuit 28 incorporates one or more ultracapacitors or super capacitors to provide the power for supplying the light-emitting device in the tip structure 14. The one or more ultracapacitors 90 could be utilized to replace batteries in the power supply circuit 28. The ultracapacitors provide high-energy storage, and are able to deliver power instantly when called upon, such as to power the light-emitting device. The ultracapacitors also charge very rapidly, sometimes in seconds, using the charging or charger circuits described herein in accordance with aspects of the invention. They can also be used to provide a necessary sudden burst of energy for applications of the device 10 of the invention. The rapid charging time provided by the power supply circuit 28 of the invention provides quick-charge applications, and eliminates the need for rechargeable batteries, which may require hours to fully charge. Furthermore, ultracapacitors have greater useful life. While a NiMH battery might be charged 500 cycles, or a Li-Ion battery 300 cycles, the present invention uses ultracapacitors that might be charged 500,000 cycles. Furthermore, such ultracapacitors that are charged and discharged as described herein do not have a memory (like battery units), have a reduced weight and cost, and do not yield hazardous waste upon disposal. For example, NiMH and Li-Ion batteries weigh significantly more on average than ultracapacitors.

A device 10, utilizing the features of the present invention, may be coupled to a suitable external power source, such as in a power base or dock 27 with sufficient contacts to engage the contacts 70 of device 10 (FIG. 1A). The ultracapacitors 90 may be charged and then discharged over a series of use cycles, such as curing cycles, for the device 10. The device may then be replaced into its charging base, or dock, to recharge the ultracapacitor. Generally, the ultracapacitor elements will not need replacement during the lifetime of the device 10, as would batteries. Since the ultracapacitors 90 charge very rapidly, the down time between charging cycles for a device 10 is very short. For example, while a NiMH battery or Li-Ion battery might take around 2.5 hours to charge fully, an ultracapacitor, as charged in accordance with the circuits of the invention, might be fully charged in 15 seconds.

FIG. 6 is a circuit schematic of one possible charging or charger circuit to be utilized within the base unit or dock 27 for charging device 10 and particularly for charging the ultracapacitors that would be provided in one such embodiment of the invention. Charger circuit 100 includes a power supply circuit/component 102 that provides suitable DC power to the circuit. For example, the power supply 102 may be coupled with an appropriate AC power cord 104 for plugging into an AC outlet, and provides DC power within the range of 5-24 Volts, for example. An indicator LED 106 might be used to provide an indication that the base 27 has power. (See FIG. 1A.) As shown in FIG. 1A, base 27 might also include indicators 111, 113 for indicating that device 10 is charging or fully charged. Circuit 100 is configured to operate as a current source in the form of a current foldback circuit, in accordance with one embodiment of the present invention. The current foldback circuit 100 is utilized to charge the ultracapacitor power supply circuit 28 of the invention, and provides a desirable rapid charge of the ultracapacitor elements 90 that differs from over how the capacitor might be charged generally. Specifically, in one embodiment of the invention, a current source is utilized to charge the ultracapacitor elements 90.

Figure 9A:
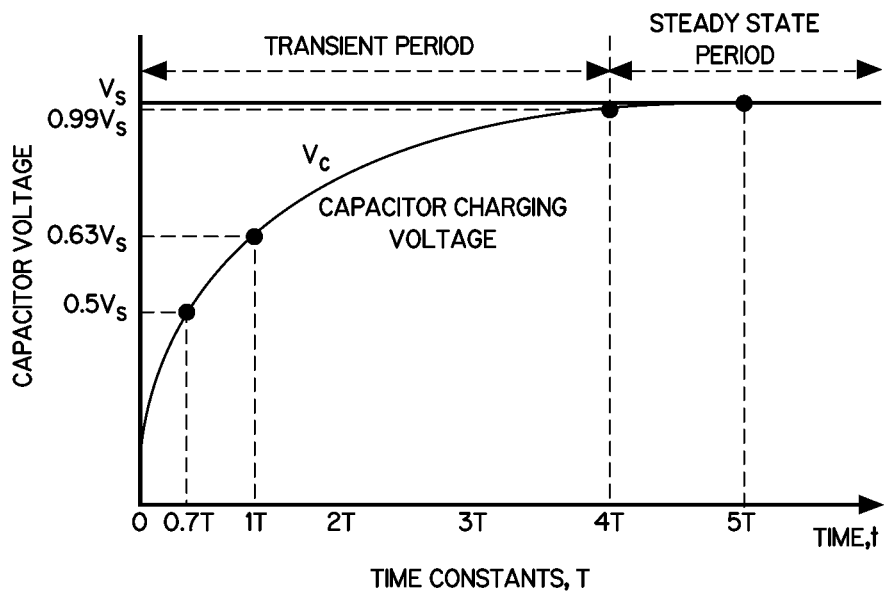
FIG. 9A is a graphical depiction of a capacitor charging curve.
Figure 9B:
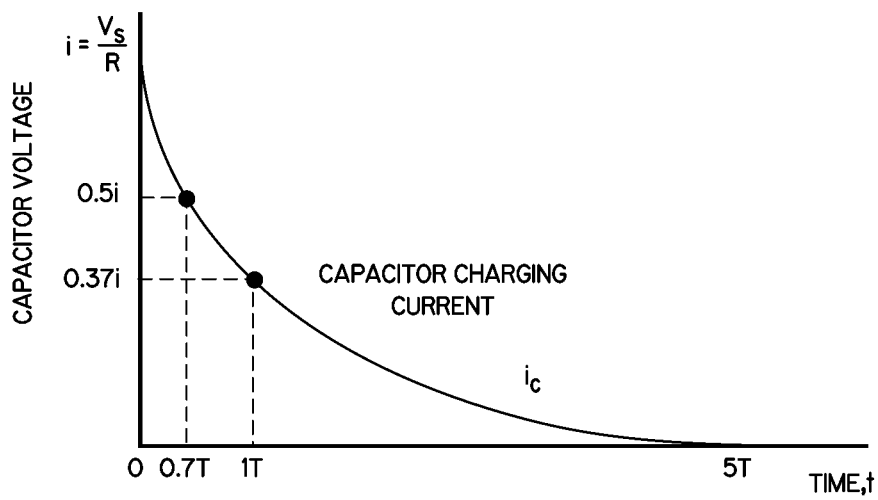
FIG. 9B is a graphical depiction of a capacitor discharging curve.

FIGS. 9A and 9B illustrate typical charge and discharge curves for a regular capacitor. For example, FIG. 9A shows a charge curve, and FIG. 9B shows a discharge curve. In general capacitor theory, the charge and discharge curves of a capacitor are considered to be exponential, as illustrated in FIGS. 9A and 9B. A single time constant, or 1T, indicates the amount of time that it takes for a capacitor to charge generally to around 63% of its full charge. The time for a full charge is expressed as 5T, as may be seen in FIG. 9A. FIG. 9B shows the discharge curve that is also exponential, wherein the time constant 1T is indicative of the time it takes to discharge to about 37% of its full charge.

However, in the present invention, it is necessary to charge ultracapacitors faster than traditional charging for the purposes of efficient use by an operator of the device 10 of the invention. That is, for certain uses, such as for curing dental compounds, it is desirable to charge the ultracapacitor very rapidly to avoid waiting and downtime in the curing process. In accordance with one embodiment of the invention as shown in FIG. 6, a current source power supply circuit 100 is used to charge the ultracapacitor at the desired rate. As illustrated in FIG. 8, the invention provides a rapid, generally non-exponential charge function for the ultracapacitor. FIG. 8 illustrates a charging ultracapacitor voltage versus time for the charger circuit of FIG. 6, and it may be seen that a very steep linear slope and charging is provided by the invention for providing a linear change function, as shown in FIG. 6. This provides significant advantages for the invention.

Returning again to FIG. 6, circuit 100 acts as a linear power supply with a current foldback function. FIG. 7 illustrates a curve associated with the operation of a current foldback supply, as illustrated in FIG. 6. When the power supply is connected to be charged, such as when device 10 is placed into the charging base 27, current is constant until the ultracapacitors are fully charged, and then there is effectively little or no output current to the ultracapacitors.

Charger circuit 100 utilizes a linear adjustable voltage regulator 108, such as an LM1084IT regulator available from National Semi-Conductor. In circuit 100, regulator 108 is a standard linear regulator where the control feedback signal is controlled by the transistor Q1 voltage Vbe. The current, through the charging ultracapacitor elements coupled to a connector 109, develops a voltage across sensing resistors (R3/R4). When the voltage across the sensing resistors is equal to the Vbe of transistor Q1 (0.6V), the transistor turns ON, and forces the linear voltage regulator 108 to foldback and limit the current generally to a value of I=0.6V/R3+R4. Once the ultracapacitors are fully charged, the current is generally or effectively 0 Amps. The capacitor charge time with such a circuit acting as a current source is illustrated in FIG. 8 as approximately T=C(V/I).

The constant power charging topology, as utilized in the invention and disclosed herein, generally transfers all the available power from the charging source or base into the energy storage ultracapacitors. The straight linear constant current or power delivery can generally provide a recharge of the power supply of the invention faster than 1T versus having to wait up to 5T, as with conventional charging of a capacitor. Effectively, the practical charge time will be set by the maximum peak current that the ultracapacitors can accept.

While FIG. 6 illustrates a charger circuit 100 that is a linear constant current foldback power supply, another alternative embodiment of the invention for fast ultracapacitor charging is to use a switched mode current mode power supply with pulse limit and pulse-by-pulse limit. In another embodiment, a lithium Ion (Li-Ion) battery charger might be utilized. Alternatively, a nickel metal hydride (NiMH) battery charger might also be utilized for the purposes of charging the ultracapacitors.

For the purposes of the invention, various different ultracapacitors might be utilized. In one embodiment, the ultracapacitor element or elements has a capacity of around 150 Farad. A range of 50-1,000 Farad might be suitable for the purposes of the invention. A multi-layer ultracapacitor might be utilized, such as one from Illinois Capacitor. Alternatively, ultracapacitors made from carbon nanotubes might also be utilized. In still another embodiment, an ultracapacitor made from carbon aerogel might be used. Lithium Ion ultracapacitors might also be utilized and provide significant cycling (e.g., 100,000 cycles) with a very low self-discharge characteristic. Another desirable feature of ultracapacitors is that they may be smaller, thinner, and lighter than conventional power supplies, such as rechargeable batteries.

Figure 14:
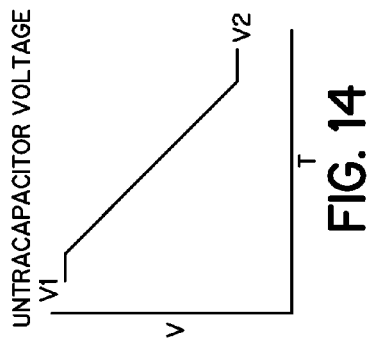
FIG. 14 is a graphical depiction of a discharge function according to an embodiment of the invention.

In one embodiment of the invention, the device 10 is utilized for curing dental compounds. In such an application, the LEDs that are used for the light device or engine 40 are generally high-power blue LEDs, such as an array of such LEDs. Such devices are generally current devices, and the light output from the LEDs is a direct function of the current provided from the power supply. In accordance with one aspect of the invention, to maintain a constant light output, the current to the LED elements or array 40 should be constant. In one feature of the invention, the present invention provides a current source to power the LEDs. That is, the ultracapacitors are discharged as a current source. To that end a desirable discharge function for the ultracapacitors of the invention is a straight linear function, as shown in FIG. 14, where the discharge time would be:

$$T_{discharge} = C(V1 - V2)/I$$

Where V1 is the full charge voltage and V2 is the lowest operating voltage.

In one embodiment of the invention, the power supply to drive the one or more LED elements or an array making up light engine 40 could be a boost pulse width modulated (PWM) current source, or a buck PWM current source. Alternatively, a buck-boost PWM current source might be utilized. Also, a flyback current source or SEPIC current source might be used as discussed below. A buck-boost topology would provide a desirable long run time (discharge time) for device 10 by providing power to the one or more LED elements when the ultracapacitors are fully charged and the voltage may be higher than the forward voltage necessary for the LED. Such a topology then also provides power to the LED when the charge on the ultracapacitors due to discharge is lower than the forward voltage for the LED. In one embodiment, using two 100 F ultracapacitors, 30-40 discharge curing cycles of 10 second each might be achieved on a single charge, for example.

Figure 10:
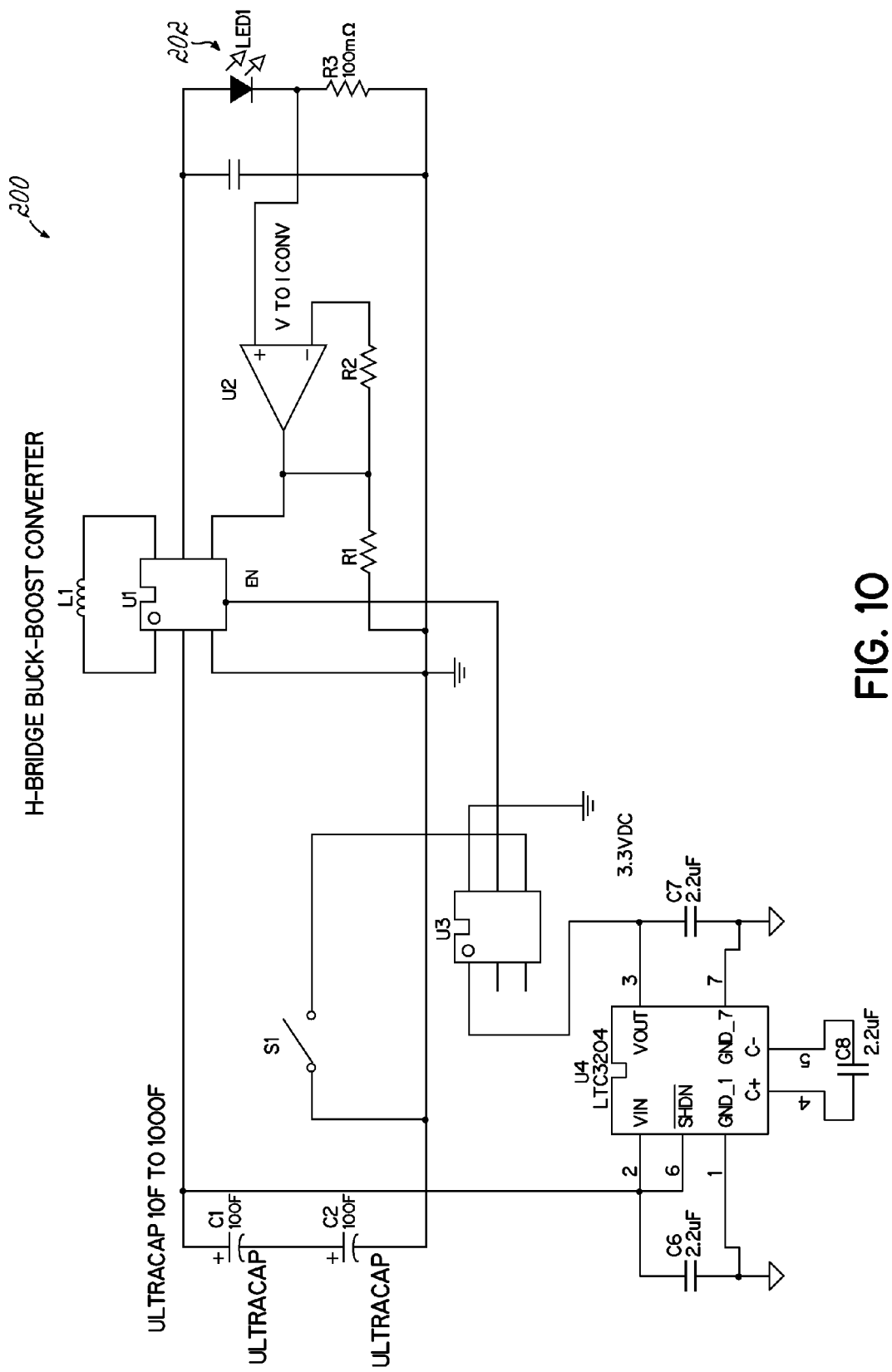
FIG. 10 is a circuit schematic showing a power supply current source circuit for one embodiment of the invention.

FIG. 10 illustrates one embodiment of a suitable buck-boost converter 200 for use in an embodiment of the invention. The embodiment illustrated in FIG. 10 illustrates two ultracapacitors C1, C2. Alternatively, a single ultracapacitor might be utilized. Still further, more than two ultracapacitors might be utilized to realize the invention, as discussed below.

As such, the present invention is not limited to any particular number of ultracapacitors that might be utilized in the power supply.

Power supply circuit 200 utilizes a PWM integrated circuit U1. U1 is coupled with inductor L1 and provides power to one or more LEDs. FIG. 10 illustrates symbolically a single LED1, however, such a symbol also covers an array of multiple LEDs. PWM circuit U1 provides power through a current sensing resistor R3. The power supply might be controlled through an ON/OFF switch S1 coupled with a suitable control circuit U3, which provides ON/OFF control and timing functionality for the operation of the LEDs and the light device. Circuit U4 provides a local power supply for the U3 control circuit. In order to control U1 as a current source in the present invention, circuit U2, such as an operational amplifier, converts the current through the LED, sensed by resistor R3, into a feedback voltage. The feedback voltage is used to control the U1 circuit as a current source, as desired. Resistors R1 and R2 set the voltage feedback level to the U2 circuit.

Figure 11:
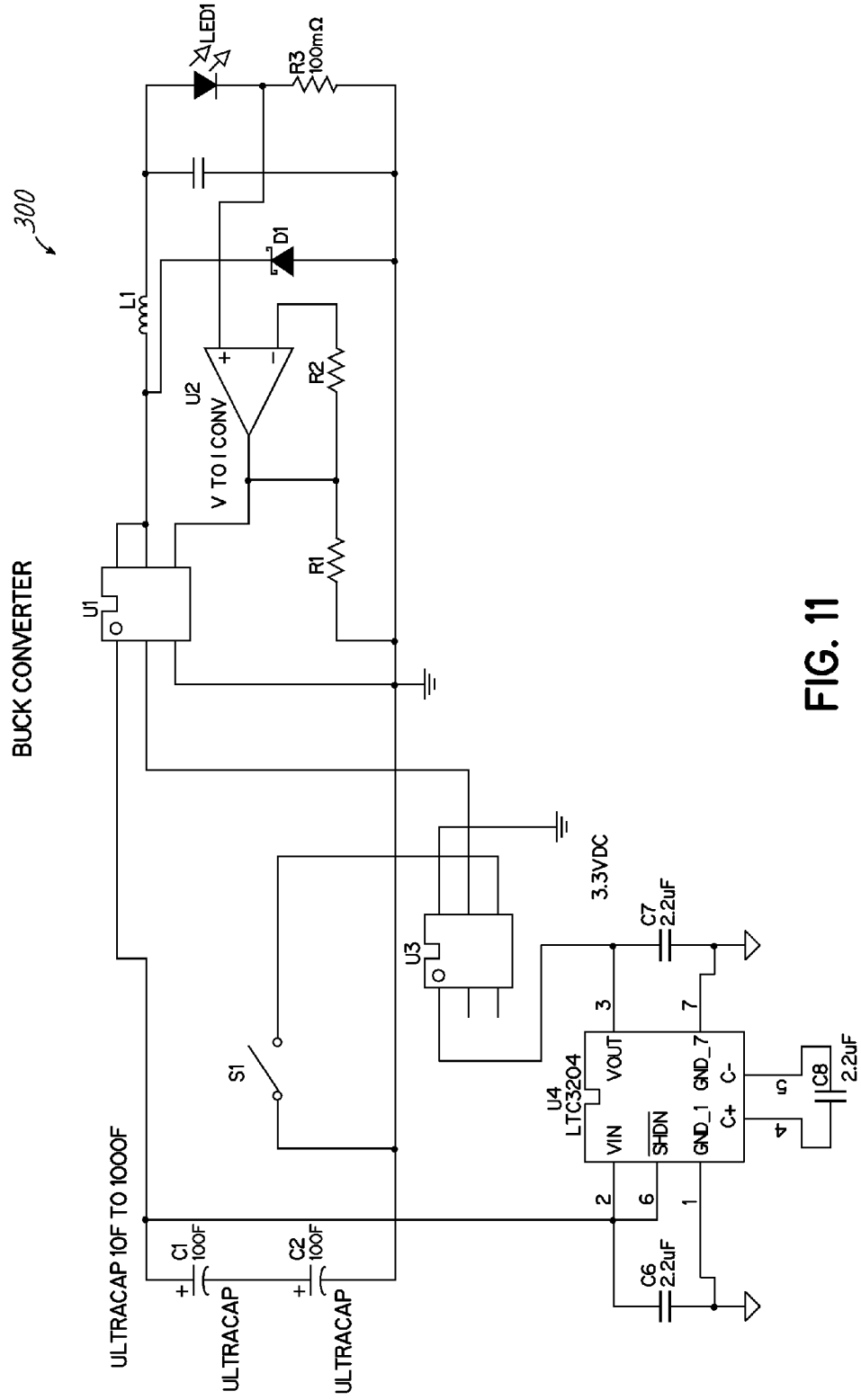
FIG. 11 is a circuit schematic showing a power supply current source circuit for another embodiment of the invention.

In an alternative embodiment of the invention, a buck converter power supply 300 might be utilized to provide a constant power load on the ultracapacitors and provide a constant current to any LED element. A buck converter topology, as illustrated in FIG. 11, somewhat resembles the buck-boost topology, as set forth in FIG. 10 with like elements sharing like reference numerals. The power path from the PWM circuit U1 includes a Schottky diode element D1 and inductor L1, as illustrated. The buck converter circuit 300 might be utilized if the LED light engine voltage requirement is less than the ultracapacitor stack voltage.

Figure 12:
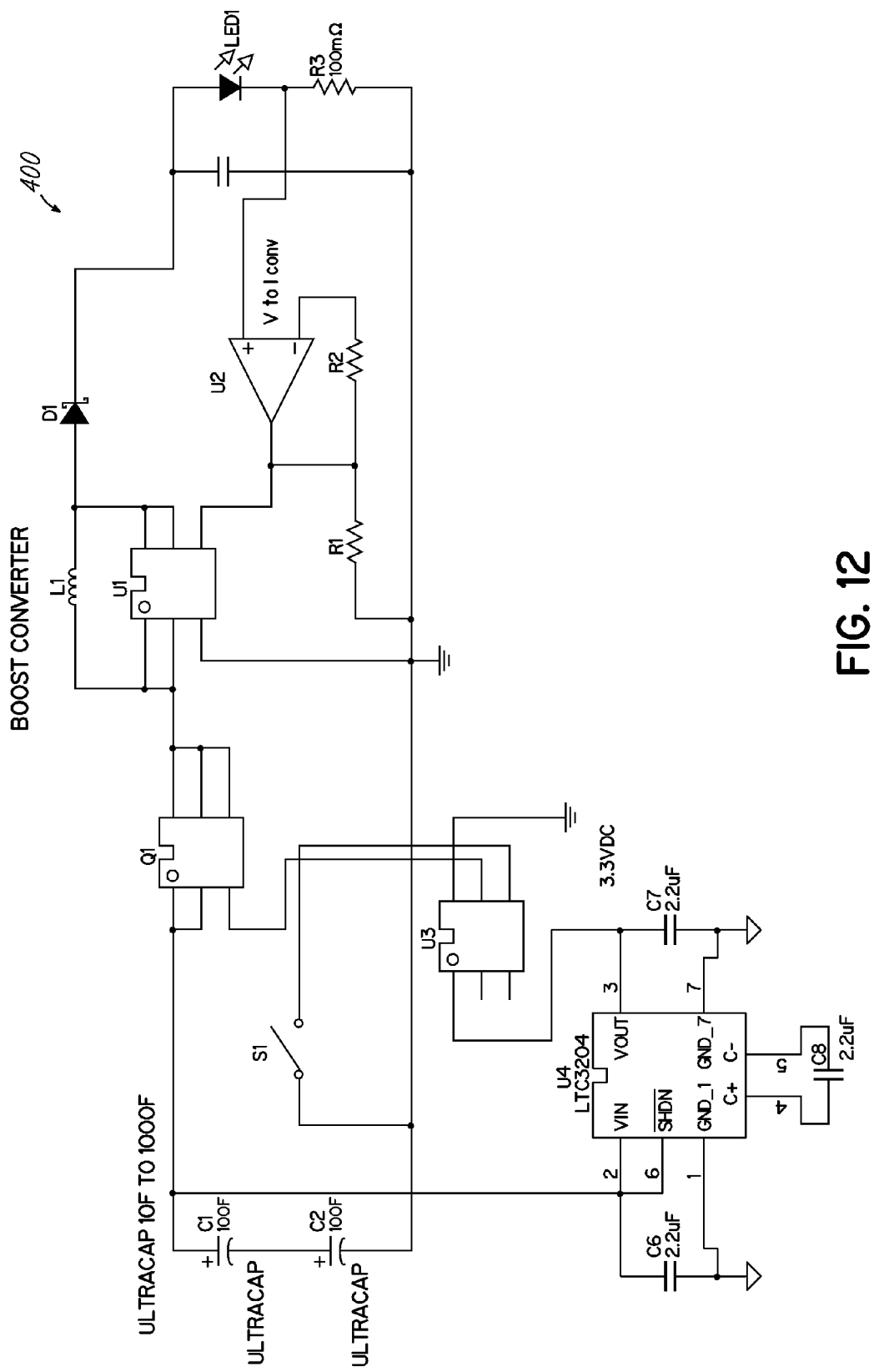
FIG. 12 is a circuit schematic showing a power supply current source circuit for another embodiment of the invention.

Alternatively, if the LED light engine voltage requirement is greater than the ultracapacitor stack voltage, a boost converter topology might be utilized. For example, the boost converter circuit 400, as illustrated in FIG. 12, might be used to drive the LED light engine. FIG. 12 resembles FIG. 10, with like reference numerals being utilized for like elements. In the boost topology of circuit 400, a solid state switch Q1 provides the functionality to turn the power supply ON/OFF based on the control of switch S1. Such a switch Q1 might also be desirable for circuits 200 and 300 as well. Schottky diode D1 and inductor element L1 are coupled appropriately for the boost converter operation.

In the circuits of FIGS. 10-12, 15, 16, PWM circuit U1 can be a standard buck, boost, or buck-boost PWM circuit that can operate at low voltages, such as from 1.5 Volts to 12 Volts. In each of the five circuits, the U2 circuit element is utilized to control the voltage feedback to the PWM U1 to provide the current source function. The voltage across the R3 element is directly proportional to the current through the LED, and the error amplifier amplifies the small voltage drop across the low Ohm sensing resistor R3 to equal the internal PWM reference voltage. The U3 circuit is a control circuit that controls the ON time of the light engine and the shutdown when the ultracapacitor has discharged to a point that is too low for use by the PWM circuit U1. The U3 circuit could be a microprocessor, microcontroller, complex programmable logic device (CPLD), or a simple analog timer, such as a ZSCT1555. The U4 circuit is a charge pump power supply that acts as a low power buck-boost controller, and provides a stable, constant supply voltage to the control circuit during the discharge of the ultracapacitor. The Q1 circuit acts as a solid state switch to disconnect the LED power supply from the ultracapacitors when the power supply is turned OFF. The power circuit 400 illustrated in FIG. 12 utilizes the Q1 element. Such a solid state switch Q1 may or may not be necessary with the buck converter of FIG. 11 or the buck-boost converter of FIG. 10. Inductor element L1 is an electronic element required for the switched power mode power supply (SMPS). The value of L1 could range generally from 1 µH up to 300 µH. The D1 element, as noted above, is a Schottky diode that generally would be utilized for the buck or boost converter configurations of FIGS. 11 and 12.

Figure 15:
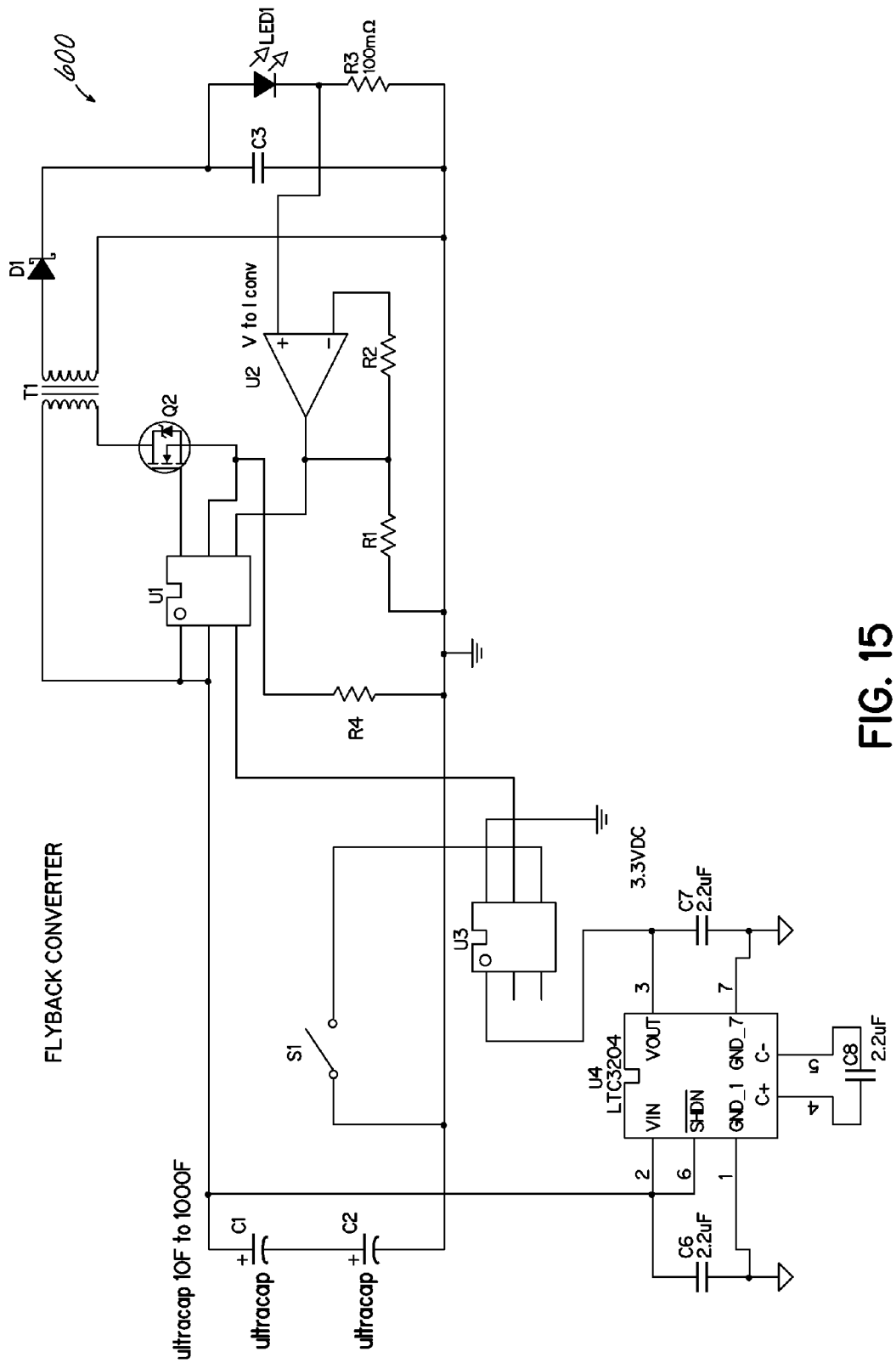
FIG. 15 is a circuit schematic showing a power supply current source circuit for another embodiment of the invention.

FIG. 15 illustrates and alternative current source for powering the LED light engine in accordance with an embodiment of the invention. FIG. 15 illustrates a flyback current source 600, wherein similar elements are used, as noted above, with respect to other embodiments. In FIG. 15, T1 indicates a flyback transformer and element Q2 illustrates a flyback switch, wherein resistor R4 is a current limit sensing resistor for switch Q2. In operation, when the switch Q2 is ON, the primary of the transformer T1 is directly connected to the input voltage source. The voltage across the secondary winding is negative, so the diode D1 is reverse-biased (i.e., blocked). The output capacitor supplies energy to the output load, such as LED 1. When the switch is OFF, the energy stored in the transformer is transferred to the output of the converter. The feedback signal from the current sensing resistor R3 is sent back to the PWM circuit U1 to control the LED current.

Figure 16:
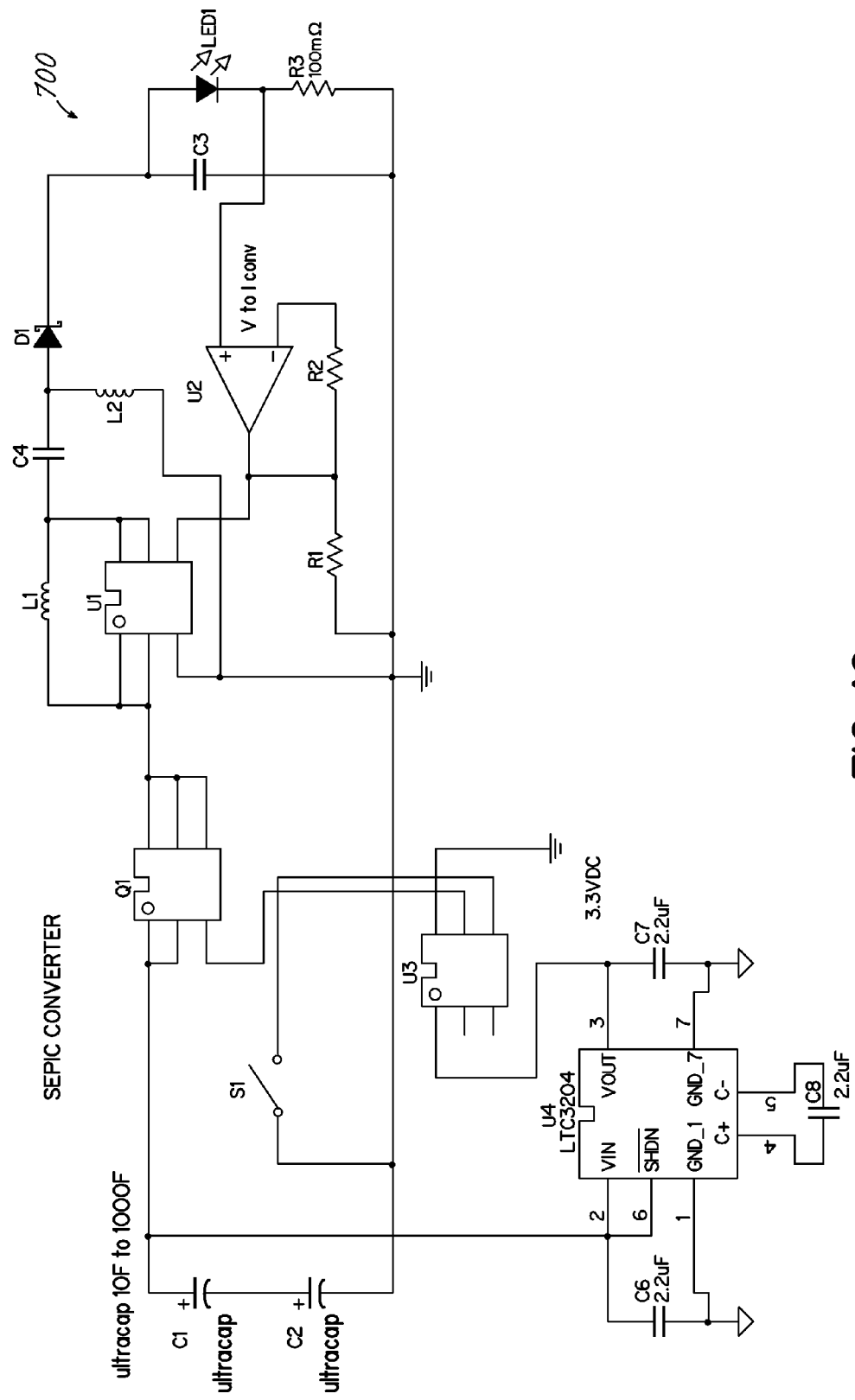
FIG. 16 is a circuit schematic showing a power supply current source circuit for another embodiment of the invention.

FIG. 16 illustrates another alternative current source in the form of a "single-ended primary inductor converter" (SEPIC) converter 700. A SEPIC converter is a type of DC-DC converter that allows the electrical voltage at its output to be greater than, less than, or equal to, that of its input. The output of the SEPIC converter is controlled by the duty cycle of the U1 circuit from the feedback signal from current sense resistor R3 that is sent back to the U1 PWM circuit to control the LED current. Similar references are used in FIG. 16 as used in FIGS. 10-13 and 15. Q1 is a solid state switch that turns the power supply ON/OFF. The split inductors L1 and L2 provide the boost function (L1) and the buck function (L2). Capacitor C4 provides AC coupling in the circuit of FIG. 16.

While the various FIGS. 10-13, 15, 16 illustrate two ultracapacitors C1 and C2 in series, a single ultracapacitor might be utilized, as noted above. Alternatively, the ultracapacitors C1, C2 might be connected together in parallel. Still further, more than two ultracapacitors might be utilized, and they might be coupled together in a series-parallel arrangement to provide the required voltage and power for the light device 10.

Figure 13:
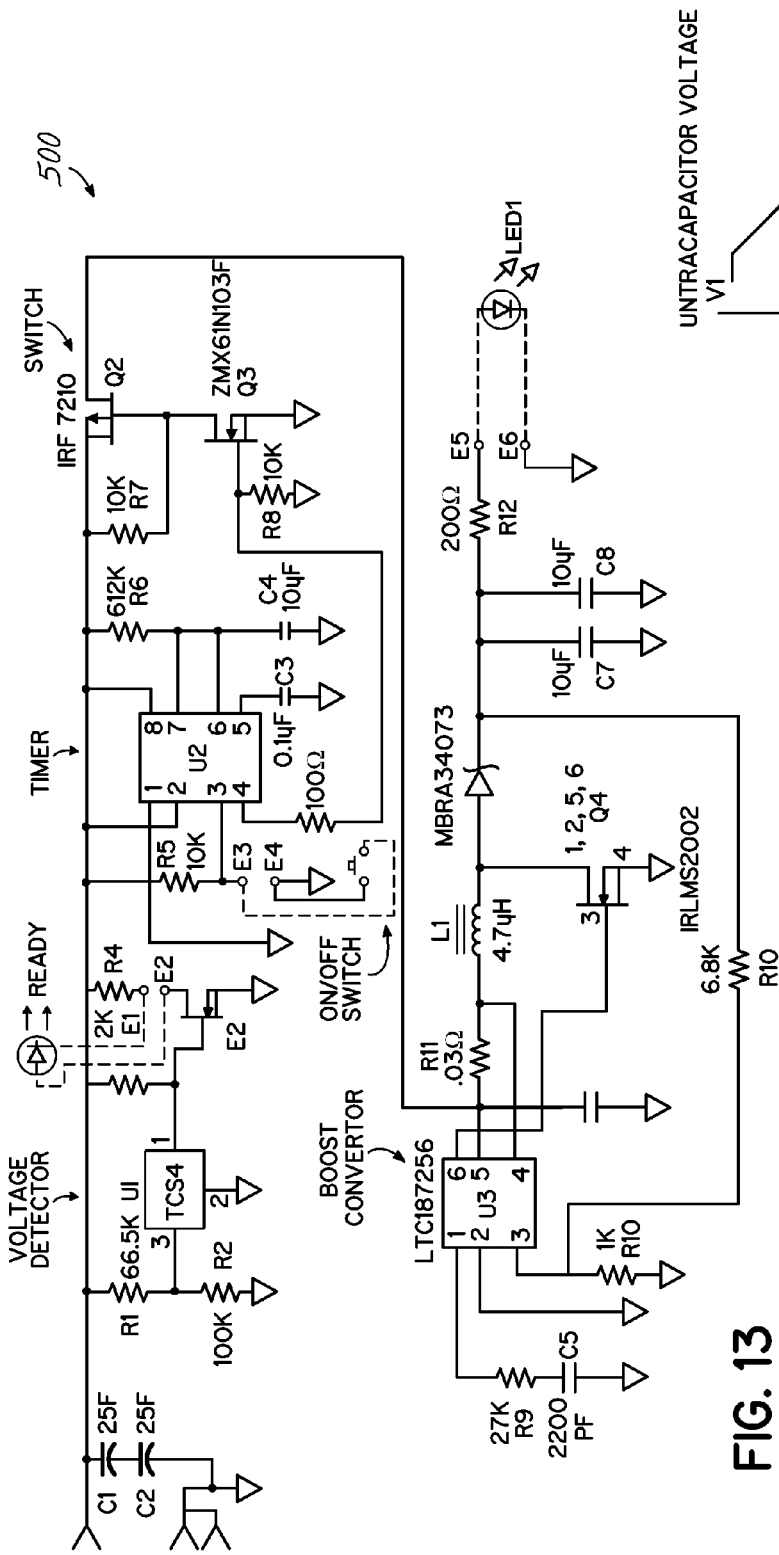
FIG. 13 is a circuit schematic showing a power supply current source circuit for another embodiment of the invention.

In an alternative embodiment of the invention, the circuit as illustrated in FIG. 13 might be utilized, such as for providing power to lower power LEDs for applications other than curing dental compounds. Circuit 500 in FIG. 13 is in the form of a boost converter, which is powered by ultracapacitors C1, C2. A voltage detector portion of the circuit provides power to a "Ready" LED (See FIG. 1A) to indicate that the light device 10 is fully charged. An ON/OFF switch portion powers a timer circuit, which drives a solid state switch Q2 to turn the power supply ON and OFF after a selected period of time (e.g., 5-40 seconds). A boost converter then provides the necessary power to an LED or LED array as shown.

Figure 17:
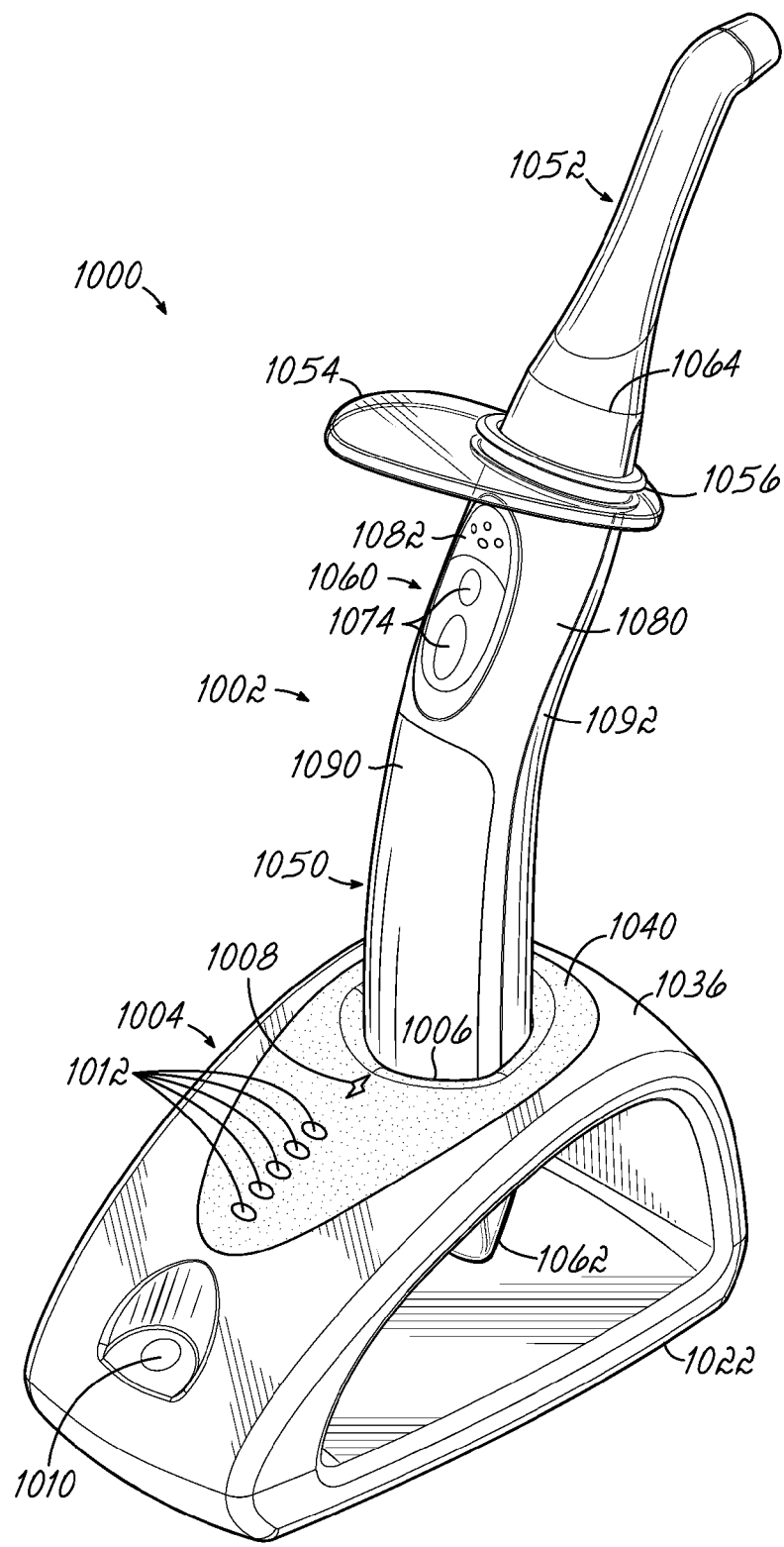
FIG. 17 is a perspective view of an alternative embodiment of a light device in a charger base.

FIG. 17 illustrates another embodiment of the invention incorporating various of the features and aspects disclosed here. Curing light system 1000 incorporates a curing light device 1002 that is shown plugged in a charger dock or base 1004. Charger base 1004, and the charger electronics therein, are coupled by a power connector cord (not shown) to an AC power supply, such as a wall outlet. The power connector cord includes an AC-to-DC converter, including appropriate transformer and inverter circuitry that provides a suitable and usable DC signal, such as a 12-Volt DC signal, to the charger base 1004. Charger base 1004 has an appropriate opening 1006 therein to hold an end of the light device 1002, as shown in FIG. 17. The light device may then be readily removed and used, such as for curing a dental compound, in the mouth of a patient. Charger base 1004 is configured to sit on a flat table or countertop surface. The charger base includes an appropriate indicator 1008 that is illuminated for indicating the charging status of a light device.

Charger base 1004 also includes a radiometer sensor for measuring the light output of the light device 1002. The radiometer sensor, as shown in FIG. 17, includes an input port 1010, and a plurality of indicator lights 1012. The output end of the light device 1002 may be placed adjacent to the input port 1010, and operated to output a beam of light. A reading by the indicators 1012 provides an indication of the power level of the output of the light device. Generally, light device 1002 will output a power level in the range of 1,100-1,800 mW/cm$^2$. The multiple indicators are illuminated in a graded fashion to provide a relative indication of that light output, as discussed below.

Referring to FIG. 17, a radiometer sensor 1010 has a plurality of indicator lights 1012 that provide a graded indication of the power of the light generated. In one embodiment of the invention, five indicators lights are used as shown in FIG. 17. The lights have different colors, and are illuminated in sequence to indicate the intensity of the light generated. To operate the radiometer, the curing time interval for the light is set to a 10 second cycle, as discussed below. Holding the tip over the radiometer sensor 1010 during the curing cycle, the indicator lights will illuminate from the bottom up, providing a reading of the light intensity. The radiometer sensor should be illuminated until the curing cycle is complete. In one embodiment of the invention, the bottom two lights are amber in color, and the top three lights are blue in color. In one feature of the invention, the indication lights have a minimum number that must be illuminated to indicate the light device is operational for a curing cycle. In accordance with one aspect of the invention, at least one blue light (3 lights total) must be illuminated for a proper cure. The first light is illuminated with an intensity of 750 mW/cm$^2$ and above. The second light is illuminated at 850 mW/cm$^2$ and above. The third light (the first blue light) is illuminated at 950 mW/cm$^2$ and above. The fourth light is illuminated at 1,050 mW/cm$^2$ and above, and the fifth light is illuminated at 1,250 mW/cm$^2$ and above. Generally, the first four lights will emit a steady glow when lit. The top indicator light is sensitive to the Periodic Level Shifting (PLS) of the light device, as noted below, and that will cause a blinking or flickering effect for the fifth light.

Figure 18:
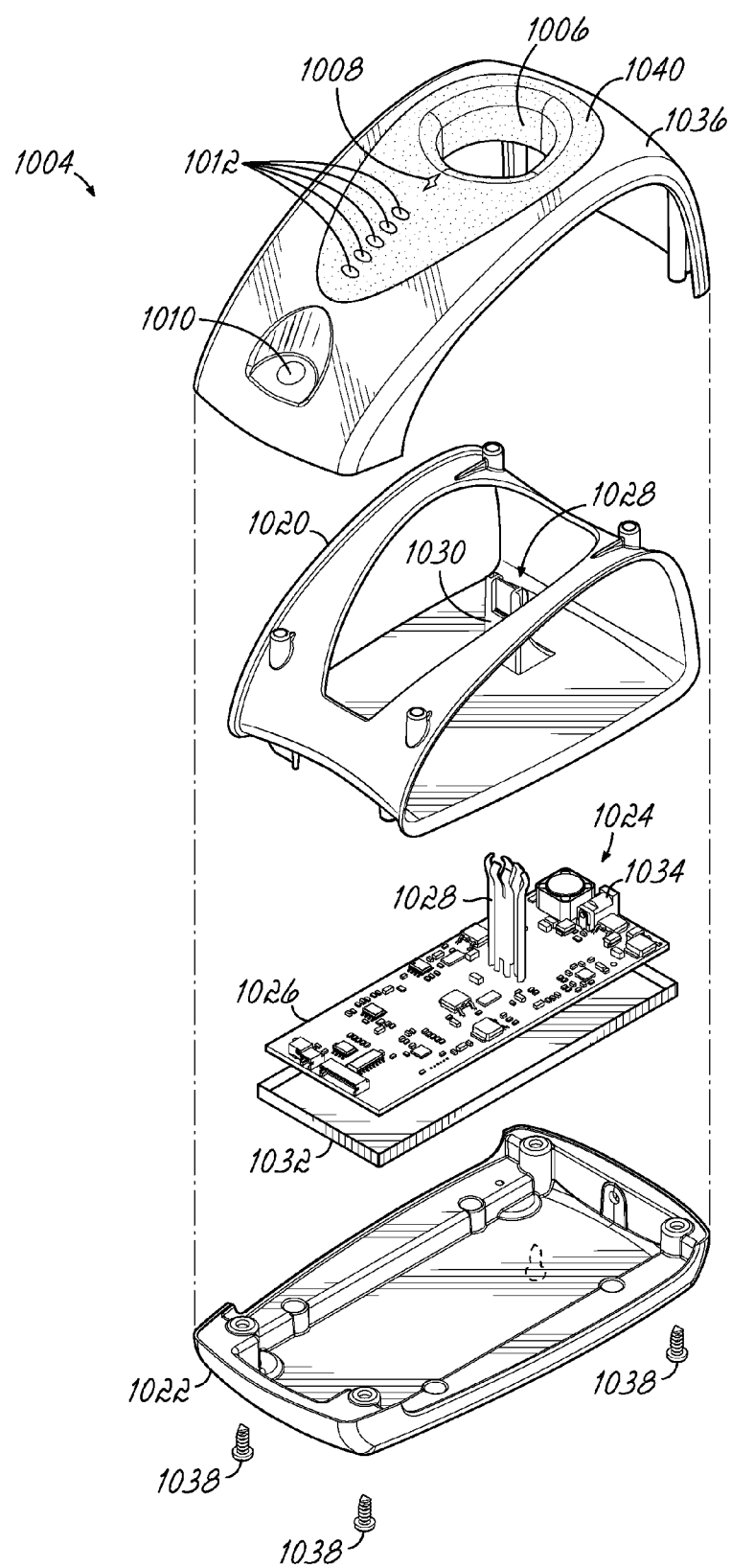
FIG. 18 is an exploded view of a charger base in accordance with the embodiment of FIG. 17.

Turning now to FIG. 18, an exploded view of the charger base 1004 is shown. Charger base 1004 includes a center portion 1020 formed out of a suitable thermoplastic, such a Valox resin, available from SABIC Innovative Plastics of Pittsfield, Massachusetts. Center portion 1020 sits on a metal base 1022. The metal base is made of a suitable metal, such as a zinc alloy, and weighs 300-320 grams, and in one embodiment, approximately 313 grams. The center portion 1020 is coupled to the various 1022 by appropriate fasteners, such as screws. Captured between the center portion and base are charger electronics 1024, which are positioned on an appropriate printed circuit board 1026. The charger electronics includes an upstanding charger plug 1028, which is captured in a suitable upstanding section 1030 of the center portion. Together, the plug and section provide an upstanding charger plug 1028 to be received into the end of the light device 1002 when the light device is seated into the charger base and plugged in, as shown in FIG. 17. To provide suitable insulation from metal base 1022, an insulator tray 1032 is positioned beneath the circuit board 1026. The charger electronics include a suitable outlet 1034 for receiving the plug of an AC/DC power cord, and delivering 12 Volts to the charger electronics 1024. A cover 1036 is then placed and appropriately secured to the center portion 1020 to provide the completed charger base 1004. Screw-in rubber feet 1038, which are secured with the metal base 1022, provide suitable engagement with a flat support surface.

A heavy metal base 1022 provides desirable weight to the charger base 1004 to hold the charger base down onto the support surface when the light device 1002 is inserted into and removed from the charger base. This provides the user the ability to readily remove the light device with a single hand, without having to hold down the charger base. The single-handed removal provides a desirable advantage and benefit, and allows the user to readily grab the light device for use with a single hand without upsetting the charger base, or otherwise securing the charger base with the other hand. The center portion 1020 and the cover, as noted, may be formed of a suitable thermoplastic, such as Valox resin. Other portions, such as indicator section 1040, might be formed of other materials, such as Lexan, a polycarbonate material. A person of ordinary skill in the art will understand that suitable materials are used for durability, aesthetics, and other purposes in forming the charger base, as well as the light device.

Figure 19:
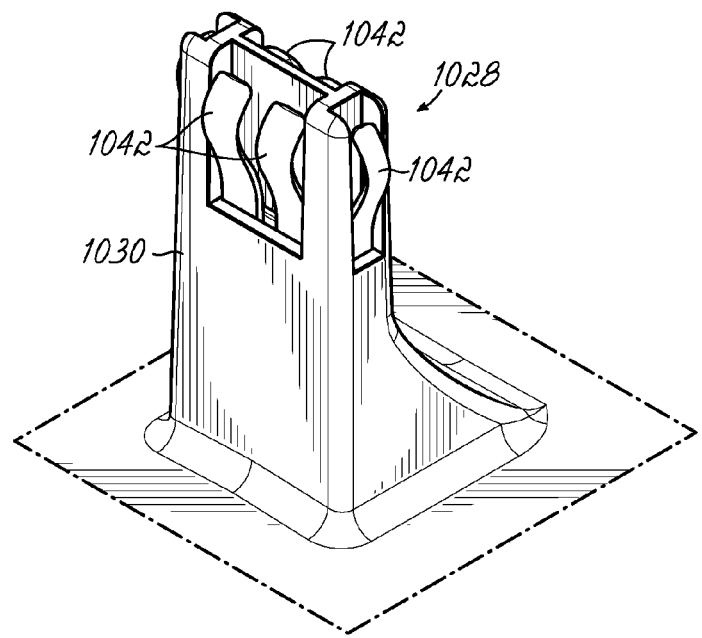
FIG. 19 is a perspective view of a plug of the charger base in accordance with the embodiment of FIG. 17.

FIG. 19 illustrates the upstanding charger plug 1028, which includes suitable charging contacts, such as metal spring-loaded fingers 1042, for providing suitable electrical contact with the light device 1002 when it is plugged in. A socket in the end of the light device receives the upstanding charge plug 1028, as discussed below. The spring-loaded charger contacts exert a force on the counterpart contacts of the plug socket 1081 in the body 150 to hold the device in the charger base and provide a robust and positive electrical contact between the device and charger base. When light device 1002 is plugged into the charger base 1004, indicator 1008 is illuminated to indicate the charging status of the light device. Different color lights indicate different status. If the light is illuminated in one color, the light device is currently charging. When the indicator light changes to another color, the light device is fully charged. In one embodiment of the invention, indicator light 1008 will illuminate in an amber color when the light device is charging, and will illuminate in a green color when the light device is fully charged. As discussed further hereinbelow, when the light device is recharged regularly, it will require only 40 seconds of charging for a full recharge. If the power source is fully drained after several days of inactivity, the unit may require up to 70 seconds for a full recharge, but then will again only require around 40 seconds for subsequent recharges.

In addition to the holding force of the spring-loaded contacts 1042, the charger base also provides a friction fit of the device 1002, when it is plugged in for charging. Specifically, a friction fit is presented between the plastic of the upstanding section 1030, and the plastic material of the plug socket 1086 at the base of device body 1050. A 4 to 5 Newton point force will be exerted by the charger base contacts 1042 on the body socket contacts (not shown) of socket 1086 at the contact points. However, the additional friction fit presented by the plastic material of section 1030 and plug socket 1086 adds an additional force on the body for a required manual removal force of approximately 7.8 Newtons. To counteract the force and provide for one-handed removal in accordance with an aspect of the invention, the charger base 1004 provides a weight of approximately 456 grams. In one embodiment, the metal base 1022 weighs around 313 grams, and the other parts and plastic portions provide the rest. To that end, a charger base weight in the range of 425-475 grams might be suitable to provide a one-handed removal. This ensures the removal force required to remove the curing light is less than the downward gravity force provided by the charger base.

Figure 20:
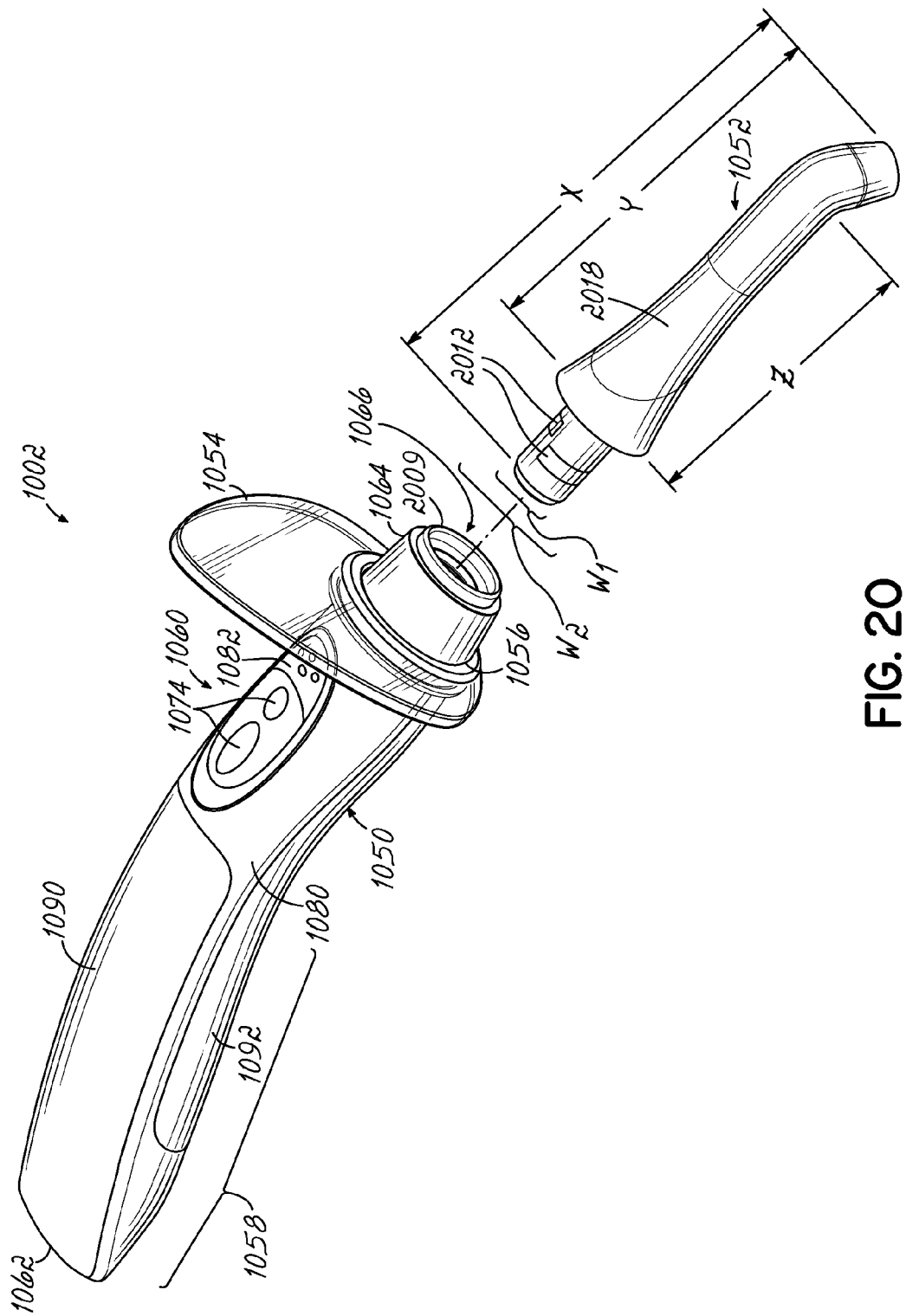
FIG. 20 is an exploded view of a light device in accordance with the embodiment of FIG. 17.

Referring to FIG. 20, in accordance with one aspect of the invention, the curing light device 1002 includes a hand piece or body 1050, and a removable LED light attachment referred to herein as tip 1052. The body is manually manipulated by a user, such as a dentist. The tip is plugged into the body, as illustrated in FIG. 20, and may be readily removed for changing or replacing the tip. Tip 1052 may also be rotated as appropriate for positioning the tip and the light therefrom at the curing site or other site. The light device also includes a light shield 1054 that is held onto the body 1050 by a rubber grommet 1056. The light shield is made of a suitable plastic material, such as an orange plastic, and is optically clear. In accordance with another aspect of the invention, the rubber grommet provides an easy removal of the shield, as desired from the body 1050, and also facilitates easy rotation of the shield as desired, such as when the tip is rotated.

The hand piece or body 1050 has a handle section 1058 to be grasped by a user, and a suitable control and indicator section 1060 that may be manually manipulated, such as by the fingers of a user, when they are holding the light device body at the handle section. The curing light device body includes a proximal end 1062, which includes a socket for plugging into the charger base, and a distal end 1064, which also includes a socket 1066 for receiving the removable tip 1052.

Figure 25:
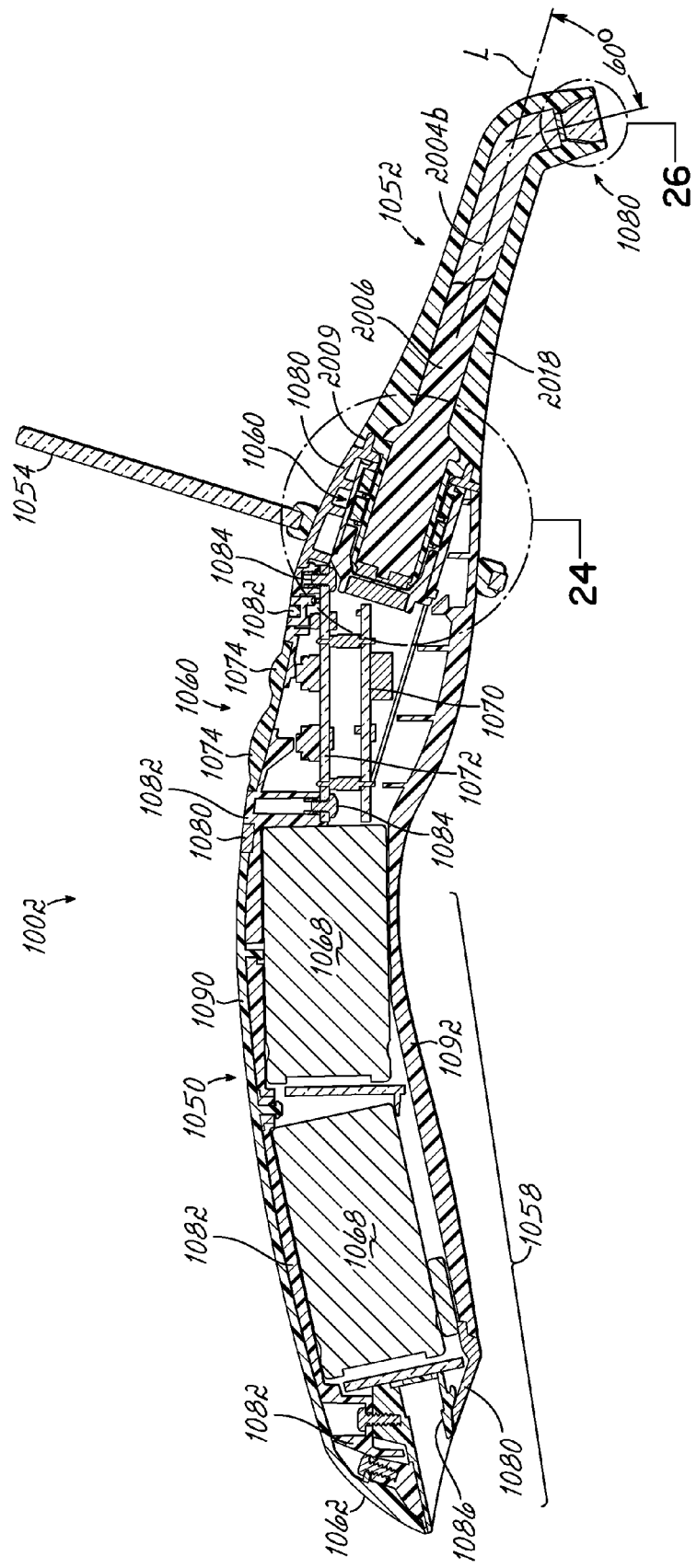
FIG. 25 is a cross-sectional view of the light device in accordance with the embodiment of FIG. 20.

FIG. 25 illustrates a cross-sectional view of curing light device 1002 showing the various components of the light device, as well as sections of the body 1050. Body 1050 encloses a power supply for the light device in the form of a plurality of ultracapacitors 1068. Light device body 1050 also encloses suitable power discharge electronics and control electronics that are positioned appropriately on a pair of printed circuit boards 1070, 1072. Generally, the ultracapacitors 1068 are contained in the handle section 1058, while the electronics 1070, 1072, are proximate the control section 1060, so that individual control buttons 1074 can interface with the electronics, and may be used to control the light device, such as to start a curing cycle.

Referring to FIGS. 20 and 25, body 1050 forms a housing for components of the device and includes an internal frame 1080, which forms a rigid structure and base for the body. The frame also provides a suitable structure for holding the socket 1066 that receives tip 1052. Frame 1080 is made of a suitable rigid material, such as aluminum. The body also includes an upper subsupport 1082 that cooperates with the frame, and provides structure for securing the boards of circuits 1070, 1072, such as with screws 1084. The sub support 1082 also supports a plug socket 1086 at the proximal end 1062 of the body, as illustrated in FIG. 25. The socket 1086 receives the upstanding plug 1028 and contacts 1042, when the curing light device is plugged into the base charger, and the socket includes appropriate metal contacts (not shown) to interface with the spring contacts 1042 of the plug in the charger base to deliver power to the ultracapacitors and light device. An upper cover 1090 and a lower cover 1092 operate with the frame and upper subsupport 1082 for forming the hand piece body 1050. The upper subsupport 1082 and covers 1090, 1092 may be formed of a suitable thermoplastic material, such a Valox resin and/or GLS VersaFlex TPE Alloy, available from PolyOne GLS of Avon Lake, Ohio. A person of ordinary skill in the art will understand that the body 1050 might be formed in various different ways, and thus, the invention is not limited specifically to the materials or arrangement of the various sections and body elements.

Figure 21:
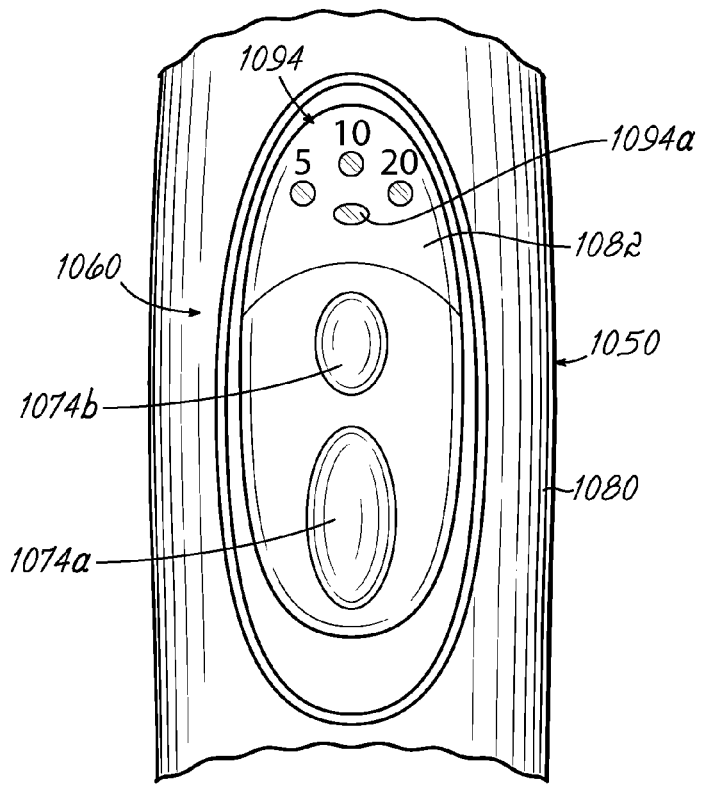
FIG. 21 is a sectional view of the light device in accordance with the embodiment of FIG. 20.

The subsupport 1082 that couples with frame 1080 defines the control section 1060, as illustrated in FIG. 21. The control section includes operational buttons 1074a, 1074b for turning the device ON and selecting an operational mode, as well as indicator lights 1094, such as for indicating the length of the cure process that has been selected, as discussed further hereinbelow.

Figure 22:
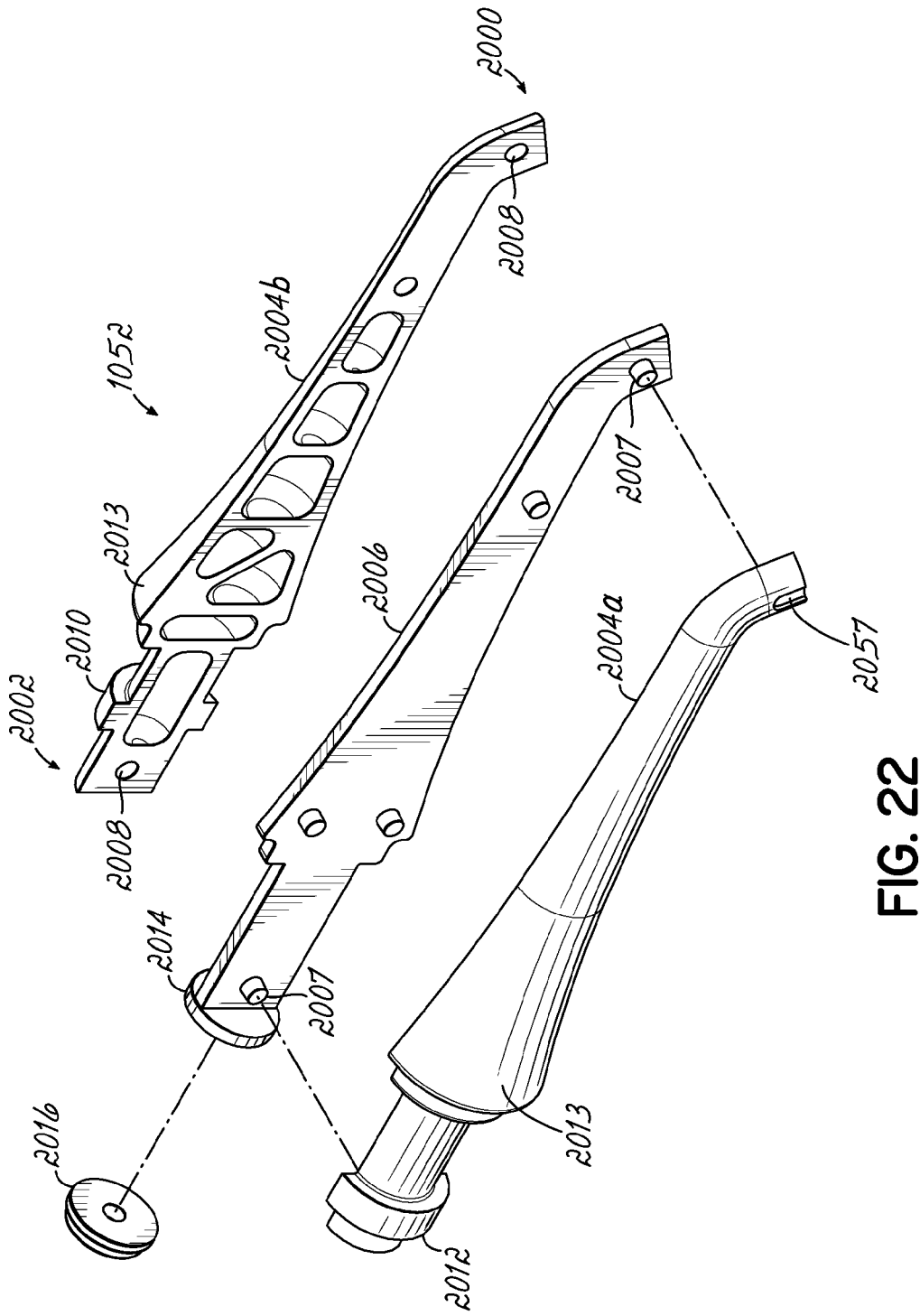
FIG. 22 is an exploded view of a removable tip for a light device in accordance with the embodiment of FIG. 20.

FIG. 22 illustrates one embodiment of the removable tip 1052 shown in the exploded view. Specifically, FIG. 22 illustrates the structure of removable tip that holds, cools, and supports the LED light engine on the distal end 2000 of the tip. The proximal end 2002 of the tip then plugs into an appropriate socket 1066, as illustrated in FIG. 20.

Tip 1052 includes two core or body elements 2004a, 2004b, which fit together in a clam-shell fashion, as illustrated. The body elements are formed of an electrically and thermally conductive material. In one embodiment, the elements 2004a, 2004b are formed of copper to provide both the conduction of electrical energy to the light engine at the distal end 2000, and to also provide thermal conduction for removing and dissipating heat that is generated when the light engine is operated. As shown in FIG. 22, an insulator plate or element 2006 is positioned between the conductive body elements 2004a, 2004b. Therefore, the body elements are electrically isolated, and may act as the positive and negative conductors, as desired below, to deliver power to the light engine of the device. The insulator element is in the form of a plate structure, and generally has the same cross-sectional shape as the body elements, as shown in FIG. 22. That insulator element incorporates alignment structures 2007 that cooperate with alignment apertures 2008 in the body elements 2004a, 2004b for proper alignment to form the finished tip 1052, as illustrated in FIG. 20, for example. The core or body elements as shown are solid out near the distal end 2000, but are also hollowed out along portions of their length, as illustrated. The proximal ends each include integral electrical contact structures 2010, 2012 that are formed with the body elements and are positioned along the length of the tip to be longitudinally offset from each other. The electrical contact structures 2010, 2012 provide electrical contact with a power source (ultracapacitors) for the tip, in order to provide electrical power out to the light engine on the distal end 2000 of the tip, as discussed further hereinbelow. In the complete tip, as shown in FIG. 20, the offset contact structures 2010, 2012 provide longitudinally separated and electrically isolated contact points, so that positive and negative contacts presented in the socket 1066, and coupled with the power supply, may make appropriate electrical contact for providing power to the light engine. The insulator element 2006 keeps the body elements 2004a, 2004b electrically insulated from each other, so that both the positive and negative positions of the signals from the power supply may be delivered from the body 1050 out to the distal end of the tip and the light engine. The insulator element includes a flat base 2014 that abuts with the ends of the body elements 2004a, 2004b. Copper body elements 2004a, 2004b might be appropriately plated, such as with a nickel plating. A steel disk 2016 is also abutted against the base 2014. The steel disk 2016 might also be plated with the nickel plating, and provides part of the securement apparatus for the tip 1052, to secure the tip in socket 1066, as discussed below.

Figure 26:
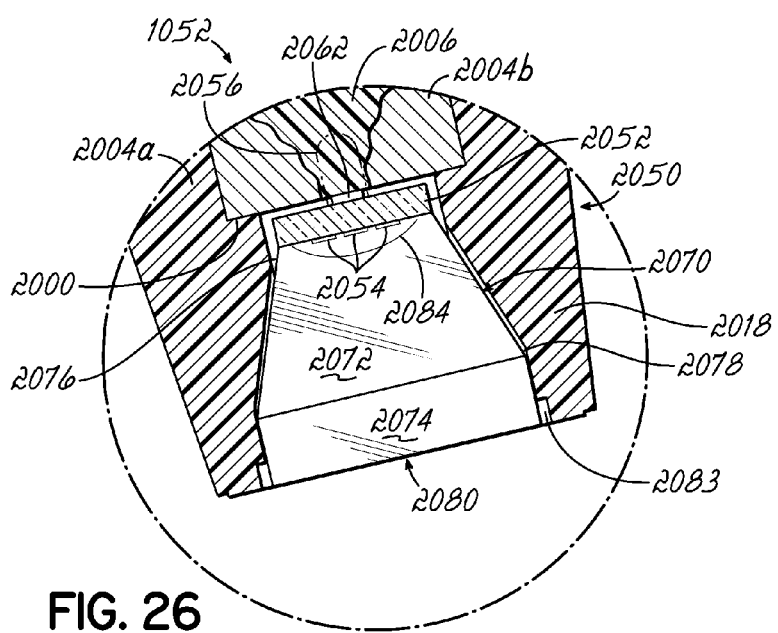
FIG. 26 is a partial cross-sectional view of a light engine for a light device in accordance with the embodiment of FIG. 20.

Once the tip is assembled as shown in FIG. 22, the entire body of the tip is appropriately covered with a suitable thermoplastic material 2018, such as Valox resin. (See FIG. 25.) A plastic material layer 2018 will generally follow the surface contours of the elements making up the tip, while still leaving the contact structures 2010, 2012 exposed for proper electrical contact, as shown in FIG. 20. As shown in FIG. 26, and discussed further hereinbelow, the light engine utilized in the curing light device 1002 is coupled to the distal end 2000 of the tip 1052.

The tip 1052 might be dimensioned for a length X end to end of approximately 4.10 inches, a length Y of approximately 3.22 inches, and a length Z of approximately 2.58 inches. The width of the plug end of the tip W might be approximately 0.34 inches, and the width $W_2$ approximately 0.94 inches, as shown in FIG. 20. This provides a stable base 2013 to tip 1052 that is wider than the proximal end 2002. Referring to FIG. 25, the distal end 2000 of the tip might be angled approximately 60° from a longitudinal axis L of the tip.

Figure 23:
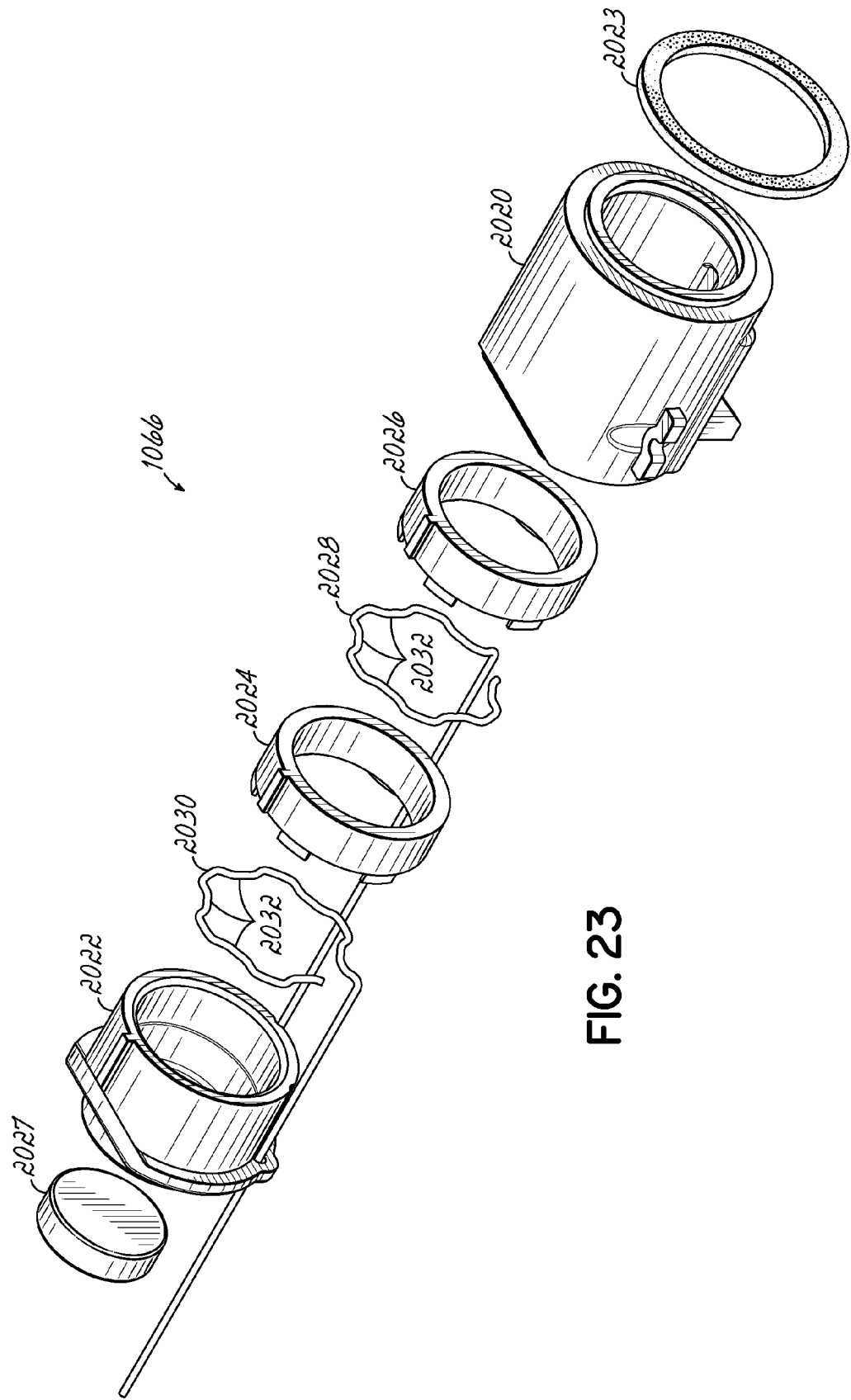
FIG. 23 is an exploded view of a socket for a light device in accordance with the embodiment of FIG. 20.
Figure 24:
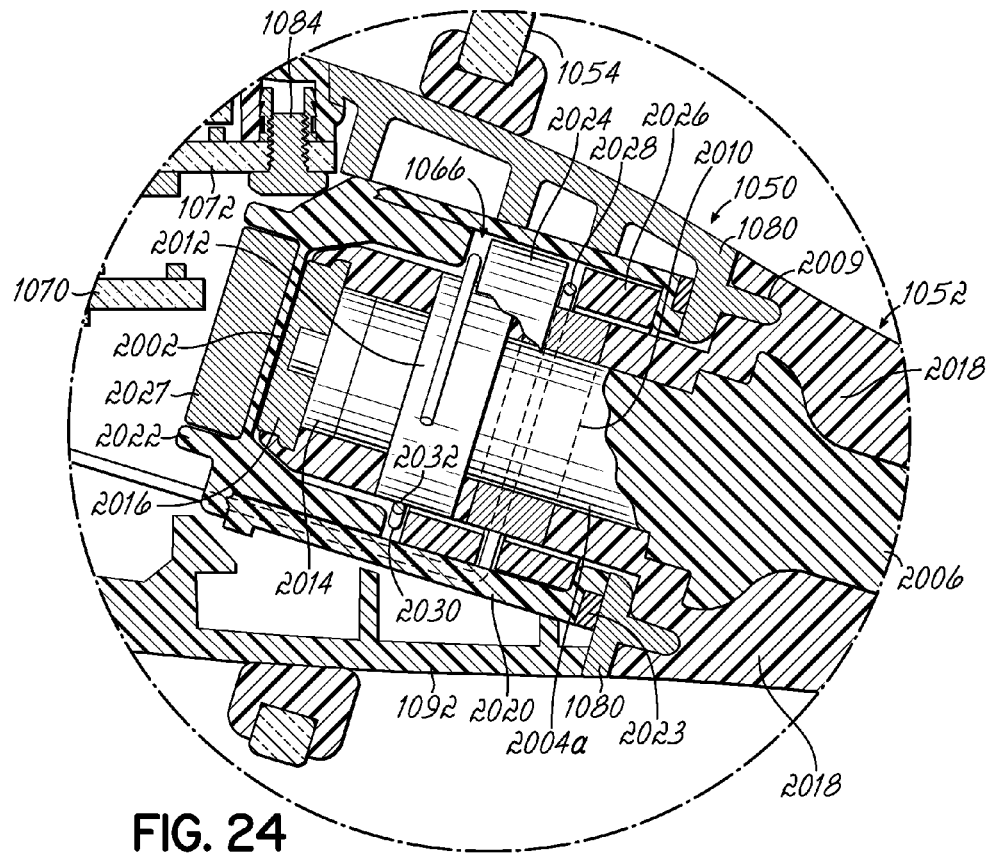
FIG. 24 is a partial cross-sectional view of the socket for a light device in accordance with the embodiment of FIG. 20.

Turning now to FIG. 23, an exploded view of the socket 1066 that is positioned at the distal end 1064 of body 1050 is shown. The socket incorporates a housing 2020, a cap 2022 that engages the housing and holds a plurality of spacers 2024, 2026 therebetween. Electrical spring contacts 2028 are appropriately held between the spacers and are aligned to physically contact the contact structures 2010, 2012 in the tip 1052 when the tip is plugged into and secured in the socket 1066. To that end, the electrical contacts are in the form of shaped spring contacts that generally surround the inside of the socket roughly 360°. The shaped spring contacts create a plurality of shoulders 2032 that provide desirable physical and electrical contact with the contact structures 2010, 2012 of the tip. As illustrated in FIG. 24, the contacts 2028 and 2030 are spaced along the length of the socket to coincide with the longitudinal offset spacing of the contact structures 2010 and 2012 at the proximal end 2002 of the tip. A gasket 2023 positioned at an end of the socket engages the subsupport 1080, as shown in FIG. 24.

In accordance with one aspect of the invention, the tip 1052 is secured in socket 1066 with a magnetic mechanism. Referring to FIG. 24, when the tip 1052 is plugged into the socket 1066, the contact structures 2010 and 2012 each are seated to press against their respective electrical contacts 2028, 2030. More specifically, the contact structures 2010, 2012 abut against the shoulders 2032 of those electrical spring contacts. The contacts 2028, 2030 and structures 2010, 2102 are dimensioned to provide a solid electrical contact all the way around the socket. To hold the tip in place, a magnet, such as a magnetic disk 2027, is positioned at the back end of the cap 2022, as illustrated in FIGS. 23 and 24. The magnetic disk magnetically attracts the steel disk 2016 in the tip proximal end. In that way, the tip is securely yet removably held in the socket 1066 of body 1050.

The magnet or magnetic disk 2027 is made of a rare earth magnetic material, such as, for example, a Neodymium Iron Boron magnet (NdFeB) that is rated N52. In the invention, other suitable rare earth magnets rated N28-N52 in their magnetic scale, or 28 $MGO_e$-52 $MGO_e$ must be used The N52 magnetic disk provides a strong securement of tip 1052 in the body 1050. This strong magnetic engagement not only physically secures the tip, but also maintains a strong and robust electrical contact between the proximal end of the tip and the contacts 2028, 2030 of the socket 1066. The magnetic securement of tip 1052 also allows the tip to be freely rotated around the socket, while staying secured in the socket. This provides greater flexibility to the user. The magnetic disk 2027 creates a pull force in the range of 0.5-6 pounds to secure the tip, and, in one embodiment, a pull force of approximately 2 pounds is provided for securing the tip in the socket. The tip can be readily rotated, but also may be readily removed when desired by manually overcoming the magnetic force. Although the magnetic mechanism is illustrated with the magnetic disk in the socket and the disk is on the tip, the arrangement might be reversed with the magnetic disk on the tip and the disk in the socket.

The spring contacts extend back from socket 1066, and contact the appropriate circuits 1070 and 1072 for providing the control for the light device and electrical power to the tip and the LED light engine. As noted, the body elements of the tip 2004a and 2004b, which are copper in an exemplary embodiment, provide the electrical connection from the electrical spring contacts 2028, 2030 to the light engine at the distal end 2000 of the tip. That is, electrical current is conducted down the length of the tip and the elements 2004a, 2004b. Simultaneously, the body elements 2004a, 2004b are also thermally conductive, and are thermally coupled with the light engine so as to draw heat away from the light engine, and away from the distal end of the tip. The heat is conducted away along the length of the tip through the body elements, and is appropriately dissipated through those body elements and through the thermoplastic material layer 2018. In that way, the light device 1002 of the invention removes the heat and provides a desirable long operating life for the light engine and the LED emitters.

Figure 26A:
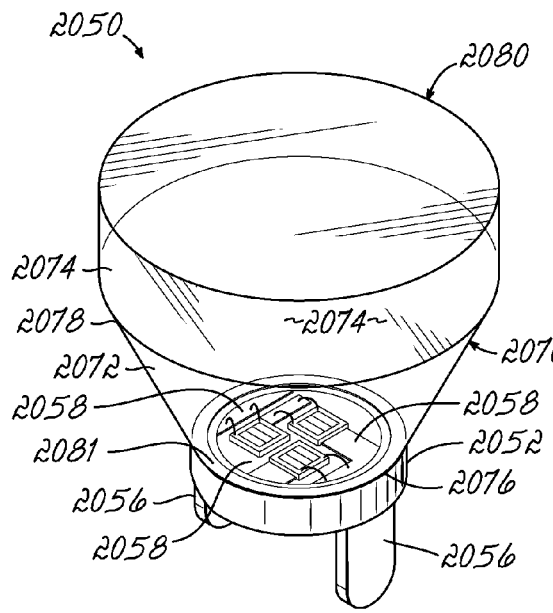
FIG. 26A is a perspective view of the light engine for a light device in accordance with the embodiment of FIG. 20.
Figure 26B:
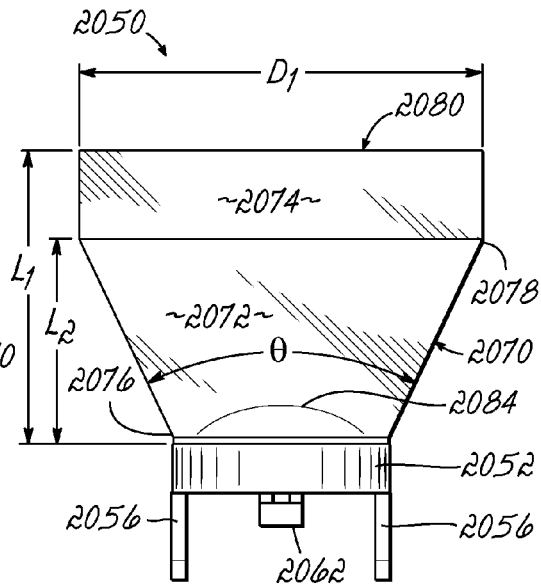
FIG. 26B is a side view of the light engine for a light device in accordance with the embodiment of FIG. 20.
Figure 26C:
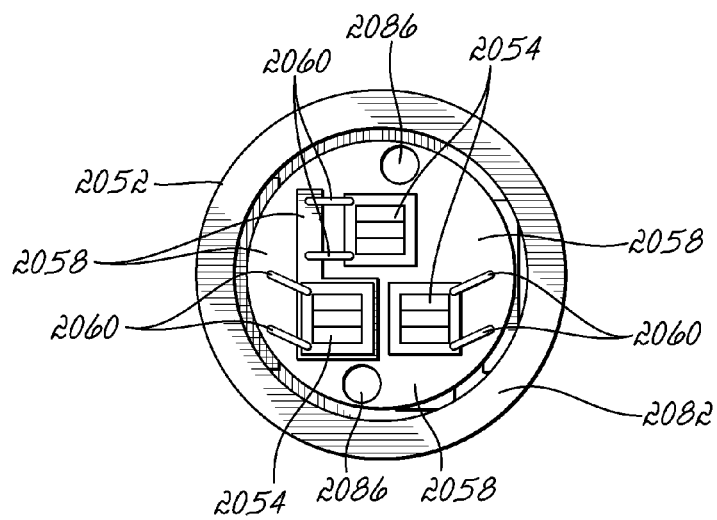
FIG. 26C is a top view of the light engine for a light device in accordance with the embodiment of FIG. 20.

Turning now to FIGS. 26-26C, one exemplary light engine for use in the invention is illustrated. Referring to FIG. 26, light engine 2050 utilizes a substrate base 2052 with one or more LED emitter devices 2054 positioned thereon. Referring to FIG. 26A, an exemplary illustrated embodiment utilizes three LED emitters that form an array. The present invention implements a light engine with this number of LED emitters in order to provide the curing light output power in the range of 1100-1800 $mW/cm^2$, as noted, while at the same time, controlling the heat generated by the light engine. The body elements 2004a, 2004b of the tip are configured and dimensioned to draw heat away to prevent a significant rise of tooth pulp temperature. The three (3) LED emitters, in combination with the unique thermal dissipation features of the tip, ensure that the heat generated during a curing cycle does not overheat or burn up the LED emitters, and does not provide heat at the distal end of the light tip that would damage the tissue of a tooth being cured. More specifically, the combination of the three LED emitters and the configurations and dimensions of the body element 2004a, 2004b are their thermal properties ensures that temperature is controlled, and the pulp temperature of a tooth being curing is not raised more than 5 degrees Centigrade. In one exemplary embodiment, LED emitters from CREE, Inc. of Durham, N.C., are utilized. Specifically, suitable CREE LED's in the EZ-900 Series might be utilized. In one embodiment, C470 EZ-900 emitters are utilized, which have a dominant wavelength 464-468.5 nm, and a radiated flux of 400 mW-420 mW. The LED emitters 2054 are appropriately physically and electrically secured to base 2052. Base 2052, for example, might be an aluminum nitride substrate that provides electrical isolation, as well as good thermal conductivity. Base 2052 is then electrically adhered to the distal end 2000 of the tip 1052. Suitable positive and negative electrical connections are provided through the body elements 2004a, 2004b of the tip, and thus, suitable electrical connections are provided to the light engine 2050.

In accordance with one embodiment of the invention, the base 2052 includes contacts 2056 that connect with the two respective body elements 2004a, 2004b of the tip. In the embodiment illustrated, the contacts 2056 are in the form of tabs that fit into slots 2057 found in the elements 2004a, 2004b, as shown in FIG. 22. Such a direct connection provides a robust electrical connection, and eliminates the need for any wiring between the tip elements 2004a, 2004b, and the substrate. As illustrated in FIGS. 26A and 26C, the top layer of the substrate includes suitable microstrip conductors and patterns 2058, and jumper wires 2060 for coupling the LED emitters 2054 together in a series electrical connection. A protective circuit component, such as a zener diode 2062 might be utilized between the contacts 2056 on the bottom of base 2052 for protection of the LED emitter elements 2054, as shown in FIG. 26B. The base and LED emitters comprising the light engine are coupled to the distal end 2000 of the tip to provide light directly to the curing site. The light does not have to pass through a long light guide, and thus, the proper amount of light can be provided while generating less heat than curing lights that implement the light engine inside the body of the device and rely upon an elongated light guide. The unique tip design, wherein the elements 2004a, 2004b act as both electrical conductors, as well as thermal conductors, also ensures that sufficient power if delivered to the light engine, while the generated heat is directed away from the light engine, and away from the distal end of the tip.

The present invention also provides greater efficiency in the light delivery by using a non-imaging optical device, such as a non-imaging lens, to capture and collimate the generated light. Referring again to FIG. 26, to collimate the light, a non-imaging lens element 2070 is coupled with the light engine. More specifically, the lens element is positioned over the light engine 2050, and particularly over the LED emitters 2054, at the distal end of the tip. Lens element 2070, as illustrated in FIGS. 26 and 26A, has a frustoconical section 2072 and a cylindrical section 2074. One end of the frustoconical section, and particularly the small diameter end 2076, is positioned over the LED emitters. The frustoconical section 2072 then tapers outwardly in diameter along its length to a larger diameter end 2078, where it continues, at that diameter, as the cylindrical section 2074. In one embodiment, the lens has lengths L of approximately 0.279 inches, and $L_2$ of approximately 0.219 inches, and a diameter D of approximately 0.320 inches. Also, the frustoconical section has a taper angle $\Theta$ of approximately 42 degrees.

Lens element 2070 is a non-imaging lens element, which collimates the light generated from LED emitters 2054, and directs that light out of a distal end 2080 of the lens element. The lens distal end or face surface 2080 generally represents the distal end of the tip 1052, and ultimately the distal end of the curing light device. In use, the distal end 2080 is positioned proximate to a work site, such as a site containing dental composite material that is to be cured. Light generated from the LED emitters 2054 is captured and collimated and effectively reflected in the body of the lens element 2070 to be directed out of the distal end 2080. In one embodiment of the invention, the lens element 2070 is a total internal reflector (TIR) lens element that is configured for capturing, collimating, and efficiently directing the light out to the end of the lens element for less optical loss and greater delivery of light energy to the curing cite. A suitable non-imaging lens element would be available from Schott North America, Inc. of Elmsford, N.Y.

To attach lens element 2070, the small diameter end 2076 might be coated to have a metalized body surface along its periphery, as illustrated in FIG. 26A by circular metal pattern 2081. Similarly, the substrate forming base 2052 includes a metallization pattern 2082 thereon for abutting metal pattern 2081 and the lens element and sealing the light engine 2050 (See FIG. 26C). The small diameter end 2076 of the lens element also incorporates a convex indentation 2084, as illustrated in FIG. 26B. The convex indentation at the small diameter end 2076 of the lens element overlies the LED emitters 2054. For further attaching the lens element and sealing the LED emitters from the environment, a silicone adhesive is injected into the convex cavity 2084, such as through openings or holes 2086 in the base 2052. More specifically, a suitable silicone adhesive might be injected into one hole, filling the cavity, while air is directed out of the other hole 2086. One suitable silicone adhesive might be available from Schott North America, Inc. as a UV-200 index matching silicone adhesive. After the silicone adhesive is injected, the holes are then sealed, such as by soldering. Thus, the LED emitters are sealed from the environment, while allowing the radiant energy therefrom to pass through the interface to lens element 2070. The lens may be further secured in the tip 1052 using an adhesive around the periphery of the lens proximate the distal end 2080. A gap 2083 is provided in the tip for such adhesive. The end of plastic material 2018 is generally flush with the face or distal surface 2080.

The light system 1000 includes the curing light device 1002, and charger base 1004, as discussed herein. Appropriate circuitry contained in both the curing light device 1002 and the charger base 1004 provides the desirable charging, discharging, and operation of the system. In accordance with one aspect of the invention, the light device 1002 incorporates a plurality of ultracapacitors for storing energy to power a light device. In an exemplary embodiment, as illustrated in FIG. 25, two ultracapacitors 1068 (sometimes called supercapacitors) are charged through charger base 1004 and the circuitry therein, and are discharged to operate the light device 1002 and power the light engine at the distal end of the tip 1052. The appropriate charger circuitry is contained on the circuit board 1026 in the charger base, as illustrated in FIG. 18. The circuitry for turning on the curing light device, changing the operational mode to the curing light device, and other operational features are contained on the appropriate circuit boards 1070 and 1072, as illustrated in FIG. 25.

The curing light device has several operational curing modes. In one embodiment of the invention, the light device may be operated to provide several different curing cycles, including a five-second (5) cycle, a ten-second (10) cycle, and a twenty-second (20) cycle. As illustrated in FIG. 21, suitable indicator lights 1094, as shown in FIG. 21, provide an indication of the curing light cycle or mode that has been selected. Appropriate controls, such as push buttons 1074a, 1074b, may be used to turn the curing light device ON and OFF, to select the operational mode and curing cycle, and to begin the curing cycle. When a particular cycle is selected, the curing light will output a light beam for the selected amount of time. In accordance with another aspect of the invention, light device 1002 incorporates periodic level shifting (PLS). Such periodic level shifting provides an increased light output, while maintaining desirable heat characteristics. Such a PLS feature is disclosed further in U.S. Pat. No. 8,113,830, which is commonly owned with the present application, and which is incorporated by reference herein in its entirety. The control circuitry provides the several curing modes of five, ten, and twenty second, with the PLS feature, or without the PLS feature. Accordingly, six operational modes might be selected.

Referring again to FIG. 21, button 1074a turns the unit ON and OFF, and also selects or deselects the PLS feature. Button 1074b controls the operating mode, and also controls an audible beeper. A charge indicator light 1094a, as shown in FIG. 21, indicates the amount of time for curing that may be provided with the current charge. When there are 40 seconds or less of curing time left, the charge indicator light 1094a glows amber, warning the user that the charge is almost depleted. The charge indicator light turns red when there is not enough charge to complete the selected curing cycle duration. If the curing cycle duration is reduced, the light may change back to amber, indicating there is enough charge for a shorter curing cycle. The three top-most indicator lights 1094, as shown, indicate the time interval or operational cycle that is selected. To change the current selection, the selector button 1074b is pressed until a desired time interval is indicated by a respective illuminated light. That is, curing cycles of 5, 10, and 20 seconds may be selected. Then, when the proper curing cycle is selected, button 1074a is engaged to start the curing cycle. When button 1074a is pressed, the PLS feature will be automatically engaged. With the PLS feature, the LED emitters will appear to be flickering at the end of the tip. If button 1074a is pressed at any time during the curing cycle, it will stop the curing cycle. In accordance with one feature of the invention, the PLS feature may be disabled by pressing and holding button 1074a, when starting the curing cycle. The PLS feature will be disabled until the button is released. While the PLS is disabled, the curing light will maintain a steady light output of around 1,100 mW/cm$^2$, and the unit will beep once per second. The curing light emits a short, audible beep when button 1074a is pressed. The beep indicates that the curing cycle has begun. A slightly longer, audible beep will sound at the end of the curing cycle. During the 10 and 20 second cycles, a beep is sounded every 5 seconds, as well as at the end of the cycle. The curing light device might also be placed into silent mode by essentially holding down button 1074b when the curing cycle is being selected. As discussed further below, the processing circuitry is appropriately configured and programmed for providing the noted operational features and curing cycles.

Figure 27:
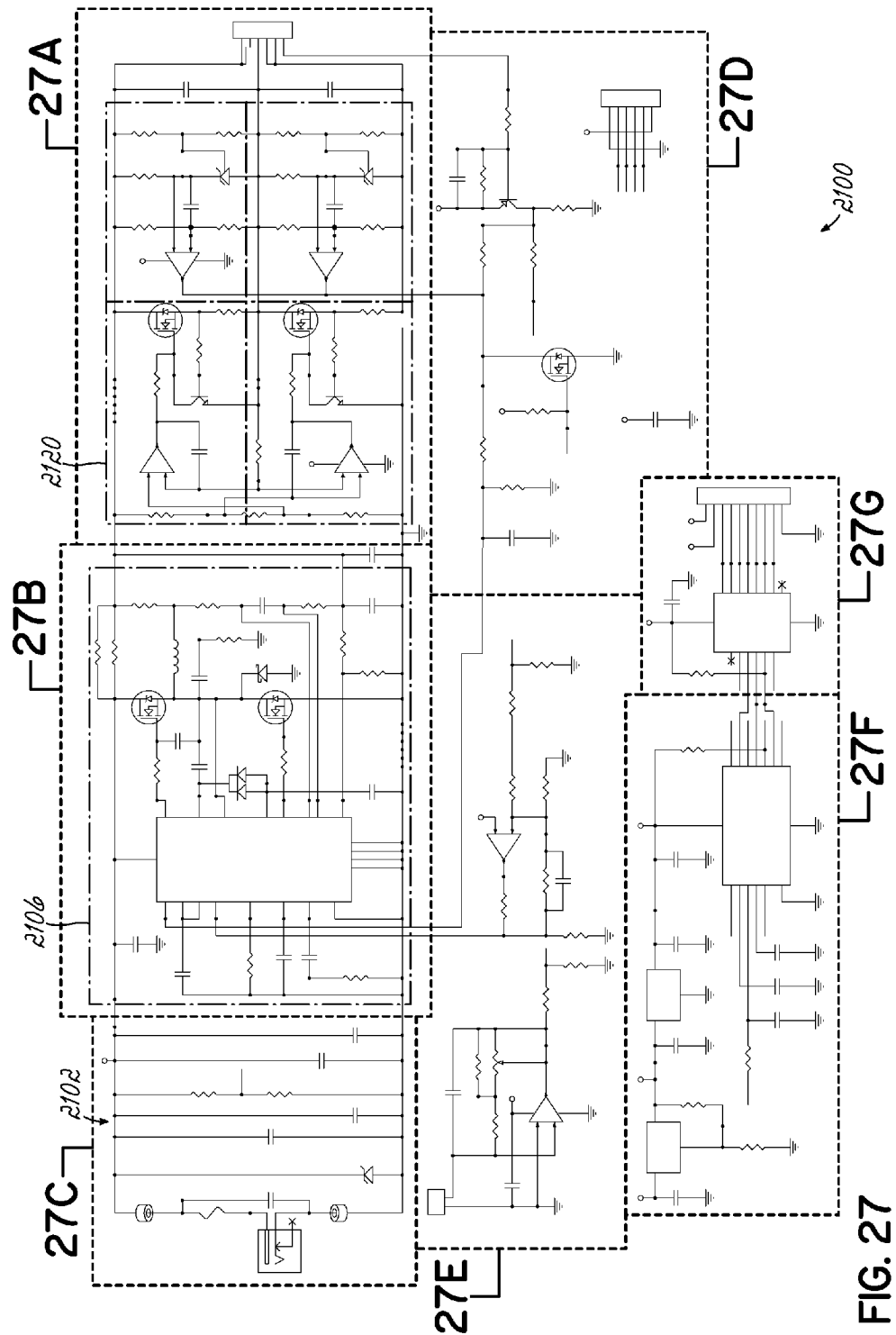
FIGS. 27-27G are circuit schematics for a charging circuit in the charger base in accordance with the embodiment of FIG. 17.

Turning to FIG. 27, a main charger circuit is shown for charging the power supply and ultracapacitors of a light device. In the exemplary embodiment described herein, various circuits and their locations will be indicated in particular locations, such as either in the charger base 1004, or in the light device 1002. However, it would be readily understood that the location of particular circuits or circuit components is not particularly limiting, and that other embodiments might incorporate different circuit components in different locations. The main charger circuit of FIG. 27 is shown broken up into several sections for the purposes of illustrating greater detail, such as in FIGS. 27A-27G. The circuitry of FIG. 27 is generally contained on board 1026, as illustrated in FIG. 18. The circuit of FIG. 27 provides voltage conversion and the delivery of the desired voltage and current to the ultracapacitors. In accordance with one feature of the invention, the charger circuit 2100 provides individual charging of two ultracapacitors in a three-point connection charging circuit for more rapid charging. Furthermore, charger circuit 2100 incorporates trickle charge sections for maximum charging. Therefore, the invention provides a very rapid charge of the light device in the order of less than, or around 40 second, so that the light device may be repeatedly used without significant downtime for the purposes of charging.

The curing light device begins immediately charging upon being engaged with the charger base. That is, when the light device is put into the appropriate opening 1006, and the upstanding plug 1028 is plugged into socket 1086, the ultracapacitors will begin to charge. Indicator 1008 on the charger base provides an indication that the charge process is ongoing, and when the device is completely charged. The ultracapacitors each have a capacitance value of 100 Farads, and will provide a desirable number of operational cycles when they are fully charged. One suitable ultracapacitor for the invention is available from Maxwell Technologies of San Diego, Calif.

In accordance with one aspect of the present invention, the power supply incorporates two 100 Farad capacitors to provide the user with a desirable run time, and desirable large number of operational cycles while still maintaining a rapid charging time. In accordance with one feature of the invention, the two ultracapacitors, operating together, when fully charged, will provide a working time or operational run time of at least 1 minute. In another embodiment of the invention, the two ultracapacitors, when fully charged, will provide an operational run time of up to 10 minutes. In accordance with one particular embodiment of the invention, approximately 250 seconds of run time are provided by a full charge of the two capacitors. For example, that would provide around 25 individual 10-second curing cycles. The inventors have determined that the two 100-Farad ultracapacitors, that are charged utilizing the unique charging circuit as noted below, will provide a rapid charge of the light device of around 40 seconds, while providing a desirable amount of run time, such as the 250 seconds of run time noted. Therefore, that unique combination of the multiple ultracapacitors and the unique charging circuitry provides desirable features for the curing light device.

In accordance with another feature of the invention, the ultracapacitors do not heat up significantly when they are being charged, or when they are being discharged, and thus, do not generate a significant amount of heat that affects their operational life like batteries do. Therefore, a consistent amount of run time may be achieved with each full recharge. Furthermore, the ultracapacitors will last up to 500,000 charging cycles, which provides a significant life to the power supply of the curing light device of the invention.

Figure 27A:
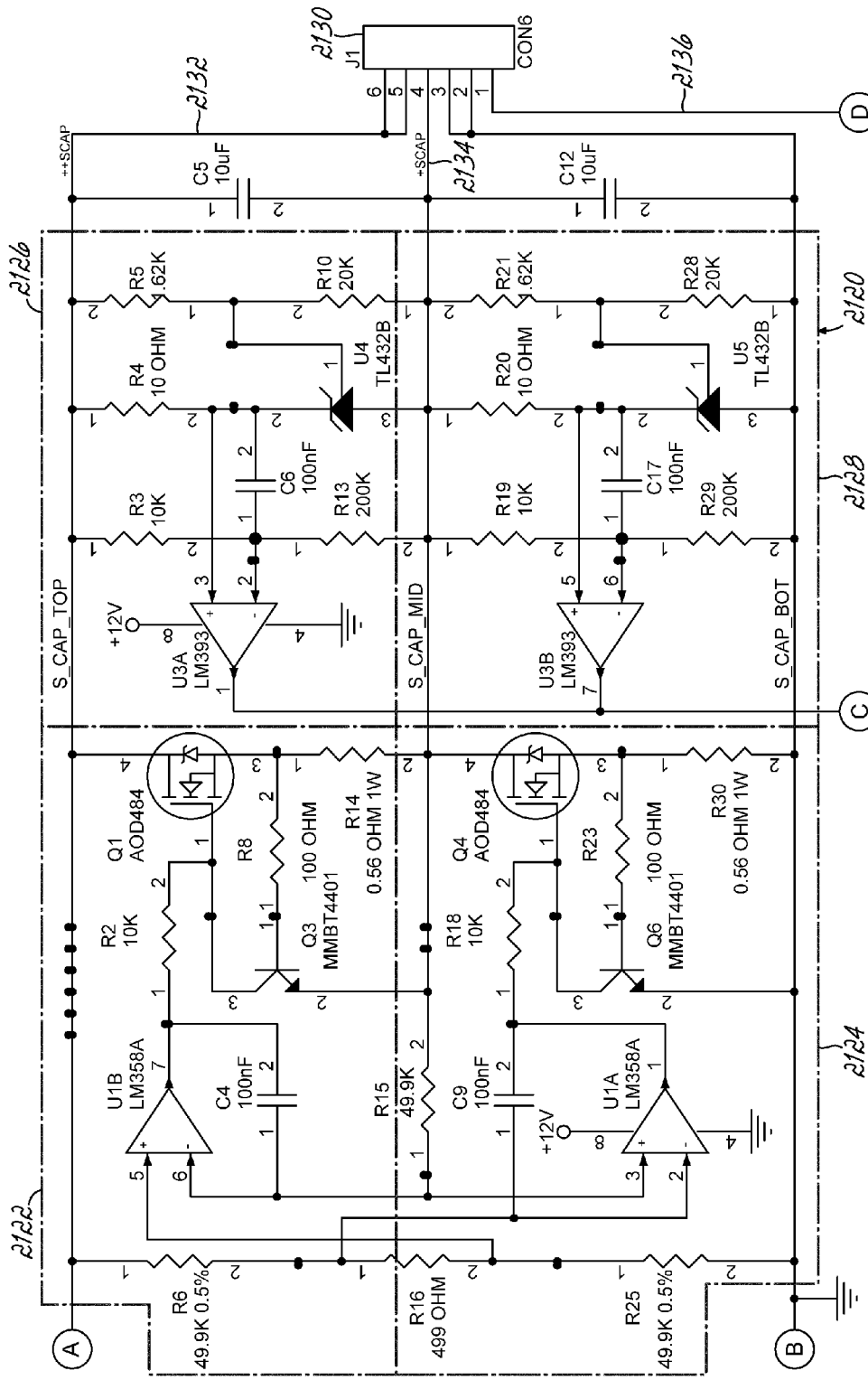
Figure 27B:
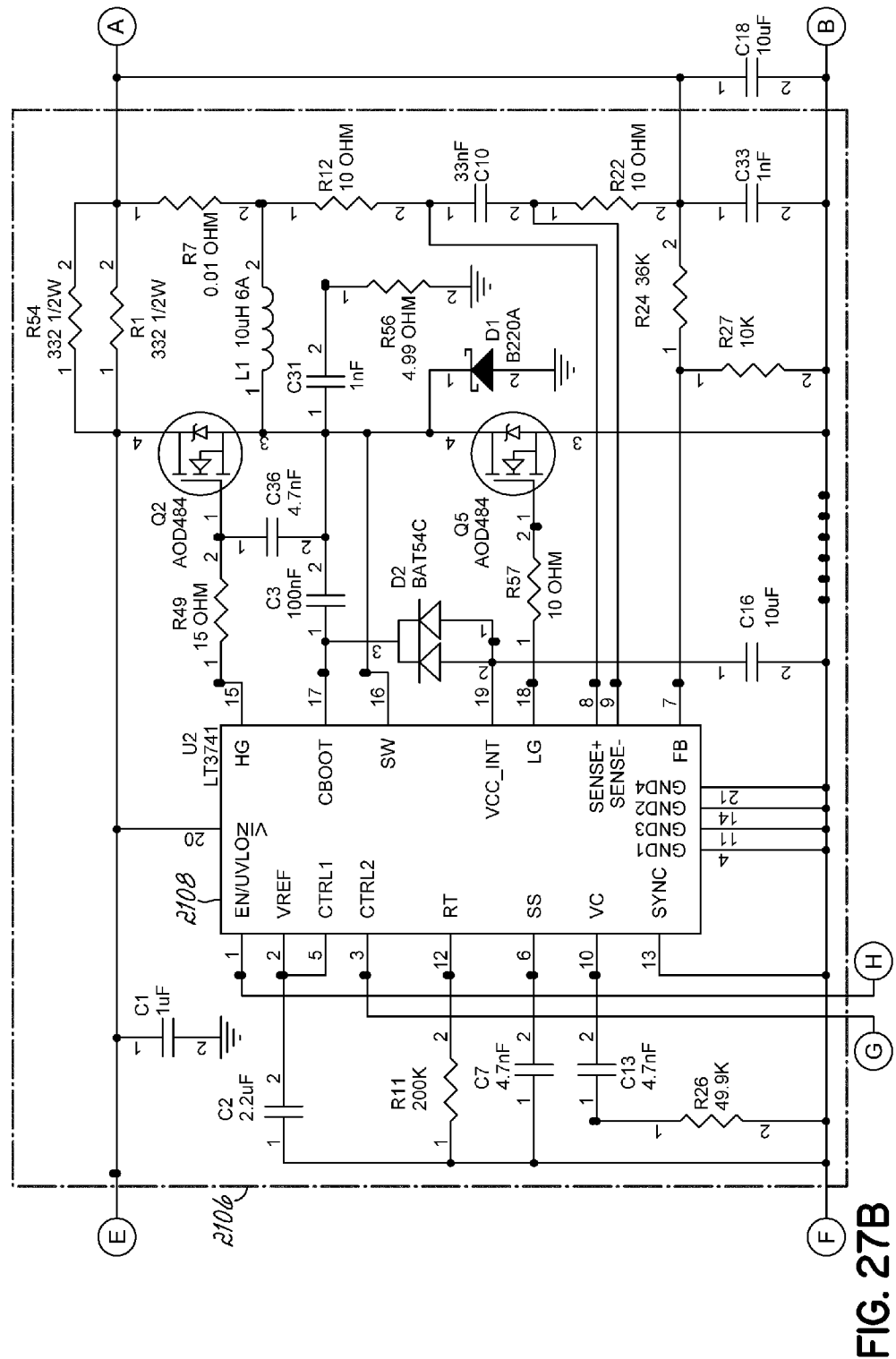
Figure 29D:
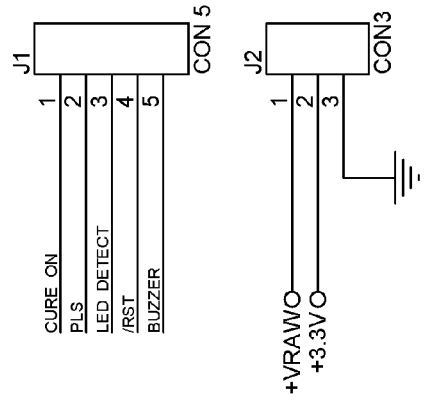
FIGS. 29-29D are circuit schematics for a discharge circuit for a light device in accordance with the embodiment of FIG. 20.
Figure 27C:
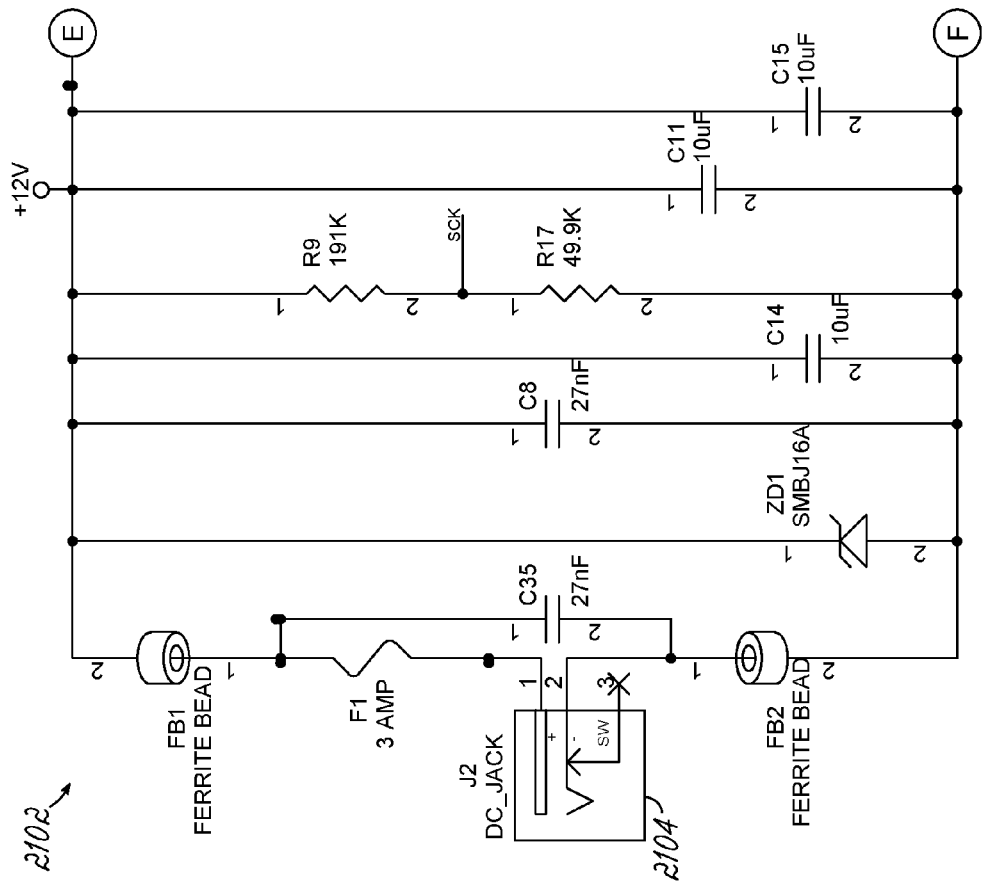

Referring to FIG. 27, the charger circuit 2100 includes an input section 2102, as illustrated in FIG. 27C. Input circuit section 2102 includes an appropriate DC jack 2104 for plugging into a DC power supply to provide the twelve-volt DC signal. Such a DC power supply (not shown) will generally include an AC plug and suitable converter circuitry to convert AC to DC to the desirable level, such as twelve volts DC. The input section delivers twelve volts DC to the main power supply section 2106, as illustrated in FIG. 27B. The main power supply section 2106 provides further DC signal conversion, such as down to a level of 5.4 volts DC. The main power supply section incorporates a suitable converter circuit 2108 to provide the step-down conversion. In one embodiment of the invention, converter circuit 2108 may be a 10V/20A constant current, constant voltage step-down converter.

The main power supply section provides a suitable DC voltage signal to the current source circuit 2120, which is coupled to the ultracapacitors to charge the ultracapacitors. Referring to FIG. 27A, the current source circuit 2120 includes sub-circuits 2122, 2124, which act as current sources. There is one current source circuit for each ultracapacitor to be charged (two ultracapacitors in the exemplary embodiment). The current source circuit 2122, 2124 are then coupled to trickle charge circuits 2126 and 2128, respectively, for each current source circuit. Each of the trickle charge circuits 2126 and 2128 provide a top-off of the charge for each of the respective ultracapacitors.

In accordance with one aspect of the invention, the current source circuit 2120, as illustrated in FIG. 27A, provides a three-point connection to the series connected ultracapacitors. As may be appreciated, two series connected ultracapacitors have a top point of connection to the first one of the ultracapacitors, a middle point of connection where each of the ultracapacitors connect to each other, and then a bottom or ground point of connection at the second ultracapacitor. Referring specifically to the connector 2130, as illustrated in FIG. 27A, the top point of connection to a first ultracapacitor is illustrated by circuit trace 2132. Circuit trace 2134 is the mid-point connection between the two ultracapacitors. Finally, circuit trace 2136 provides the ground connection to the second ultracapacitor. In that way, the various current source circuits 2122, 2124, and respective trickle charge circuits 2126, 2128 are coupled to each of the ultracapacitors in a three-point connection of traces 2132, 2134, 2136. Such a three-point connection provides rapid and efficient charging of the ultracapacitors, and also provides a complete charge that is generally equally distributed across the ultracapacitors.

Figure 27D:
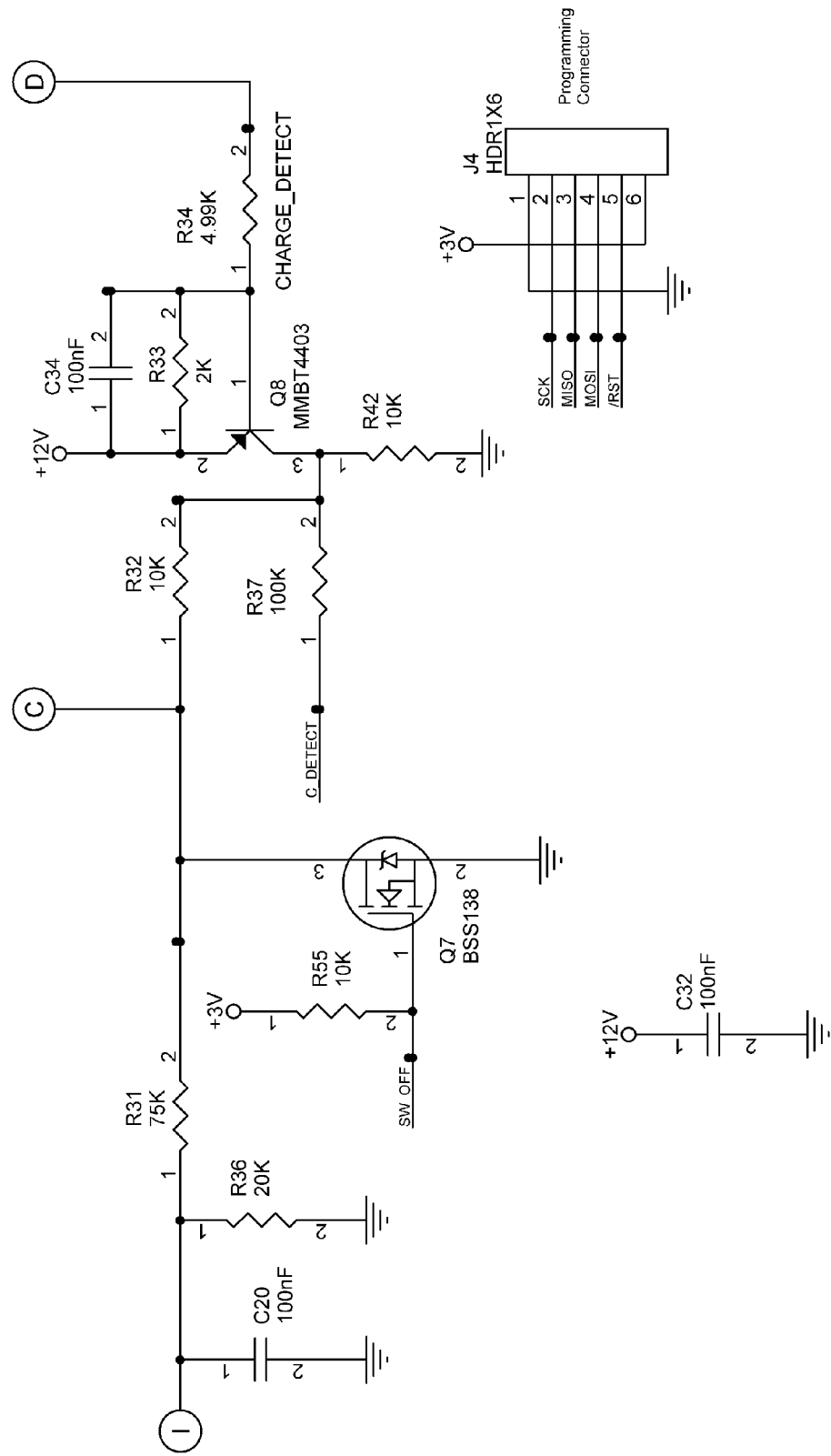
Figure 27E:
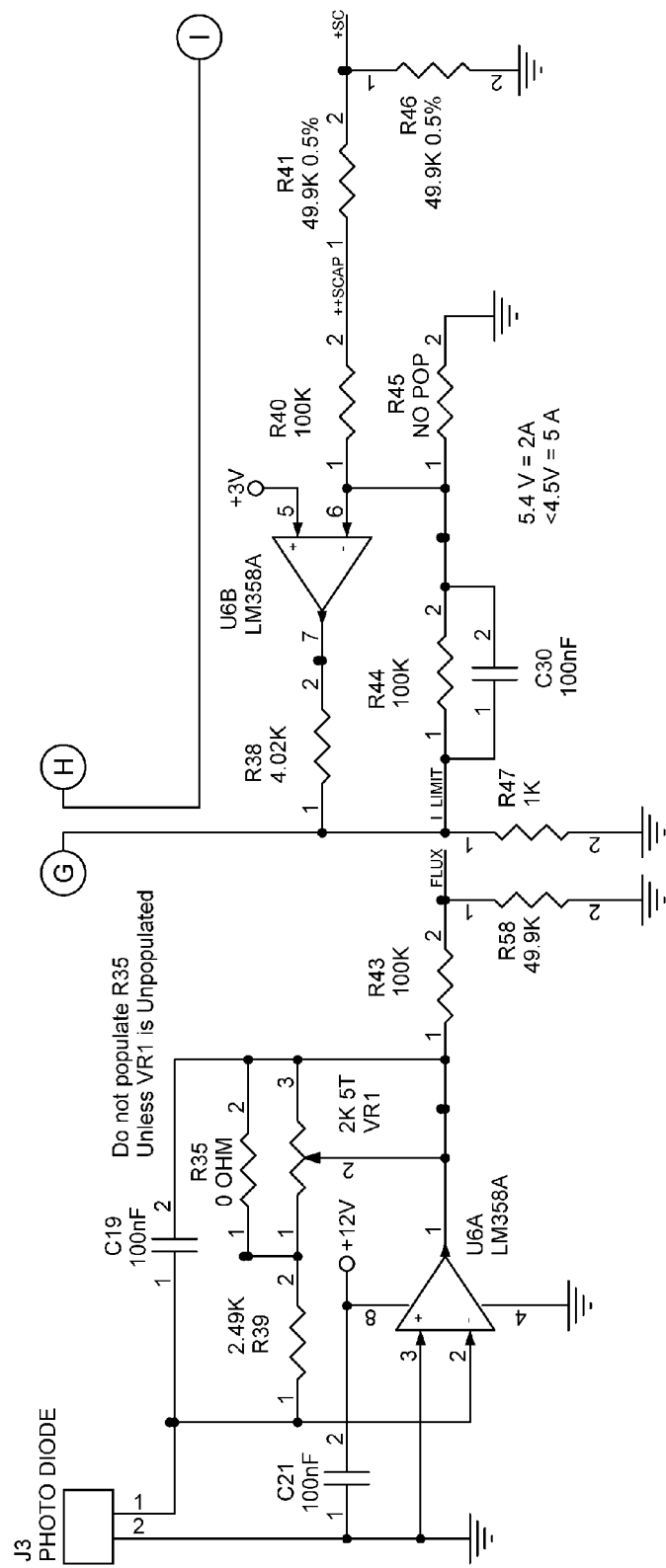

FIGS. 27D and 27E illustrate additional operational circuitry that provides the detection of the charging process, as well as an indication of the charging by a photodiode, such as to provide illumination of the indicator 1008.

Figure 27F:
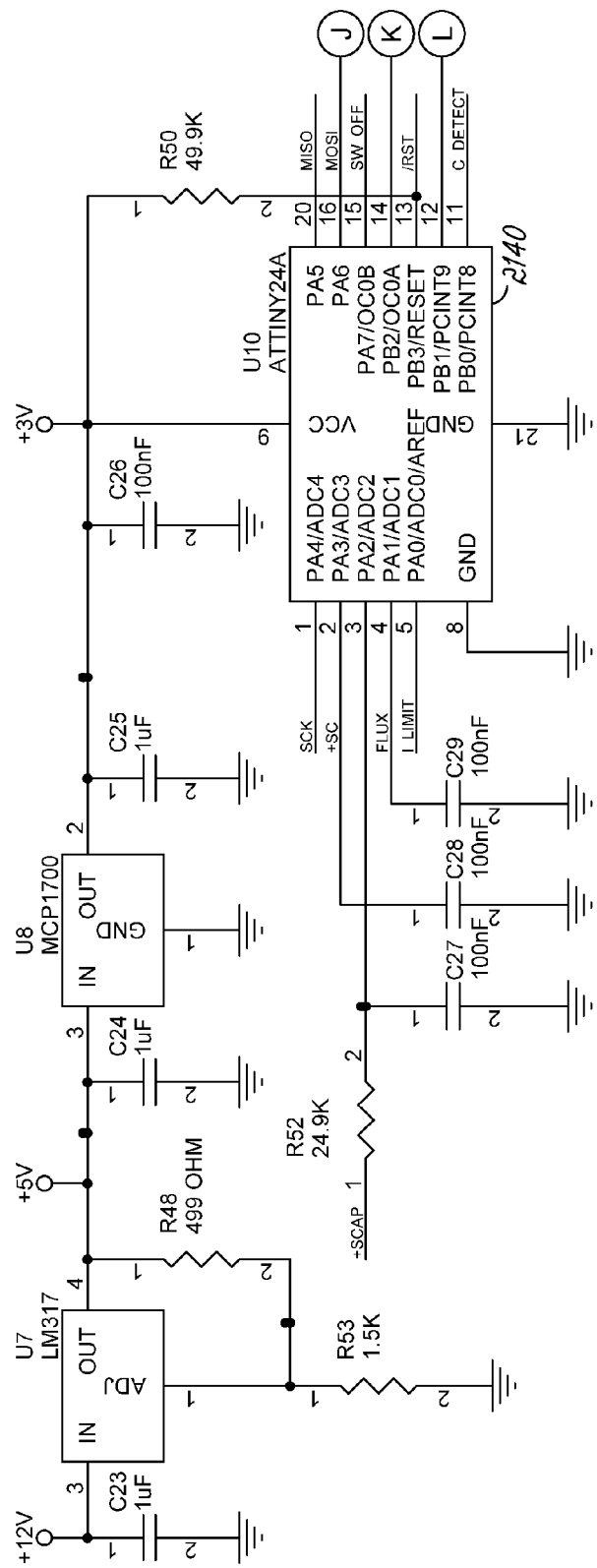
Figure 27G:
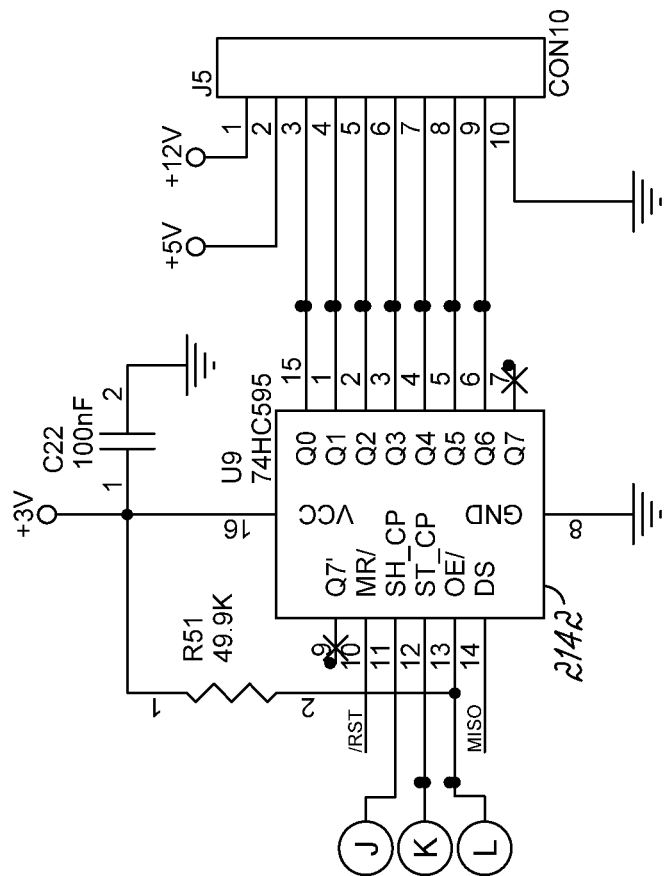

FIGS. 27F and 27G illustrate control circuitry for providing the desired control of the charging process, including a microprocessor or controller element 2140, as illustrated in FIG. 27F, and a register circuit 2142, as illustrated in FIG. 27G.

Figure 28:
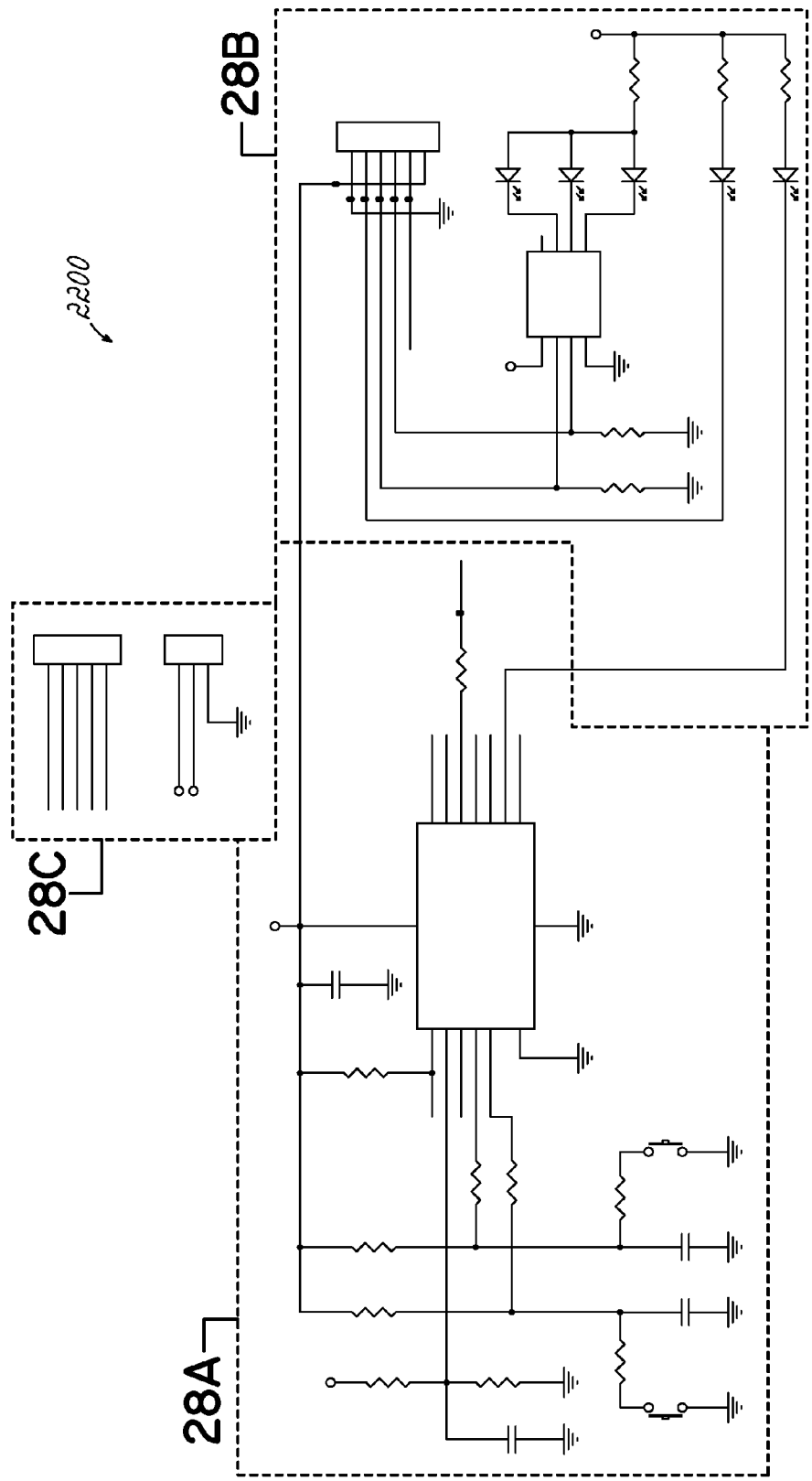
FIGS. 28-28C are circuit schematics for a main control circuit for a light device in accordance with the embodiment of FIG. 20.
Figure 28A:
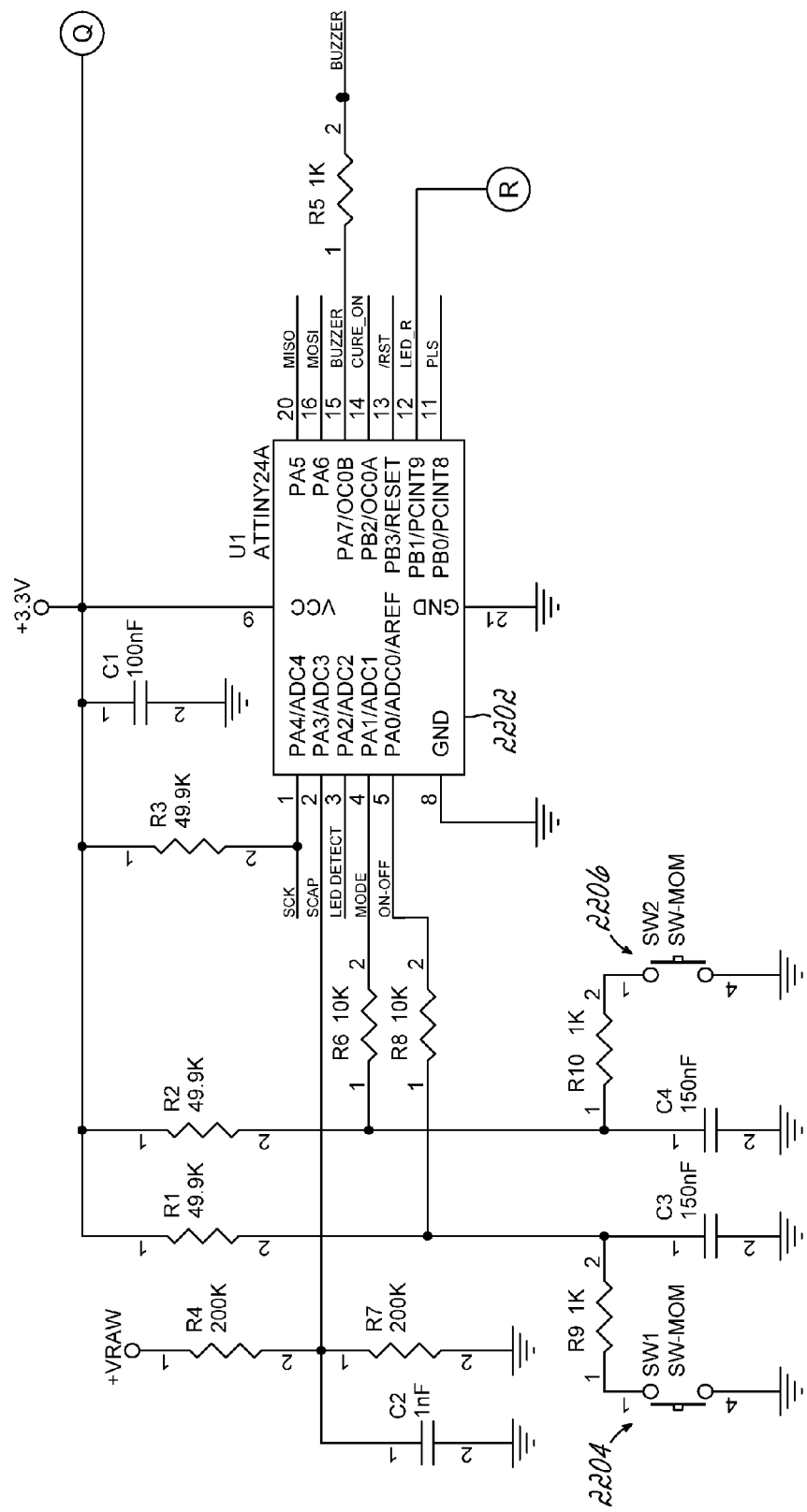

FIG. 28 illustrates a main control circuit 2200 for a light device 1002. Generally, the main control circuit will be on board 1072, in the control section 1060 of the light device body 1050. Referring to FIG. 28A, the main control circuit 2200 incorporates a control section, which includes a suitable processor or controller 2202 for controlling the operation of the light device. The controller 2202 interfaces with one or more switches 2204, 2206, which are actuated, such as by the buttons 1074, as illustrated in FIG. 25. The switches control the ON/OFF characteristics of the light device, as well as the modes that are selected for curing. The main control circuit further includes an indicator section, as illustrated in FIG. 28B, which includes various LEDs 2210, 2212, and a driver circuit 2214. The LEDs provide a desirable indication, such as through indicators 1094 to indicate the length of the cutting cycle (e.g. 5, 10, 20 seconds) as well as the particular mode, such as a PLS mode or a non-PLS mode.

As illustrated in FIG. 28C, the main control circuit will also include an appropriate connector 2216 for connecting to a discharge circuit for discharging the ultracapacitors and driving the light engine for a curing process.

Figure 29:
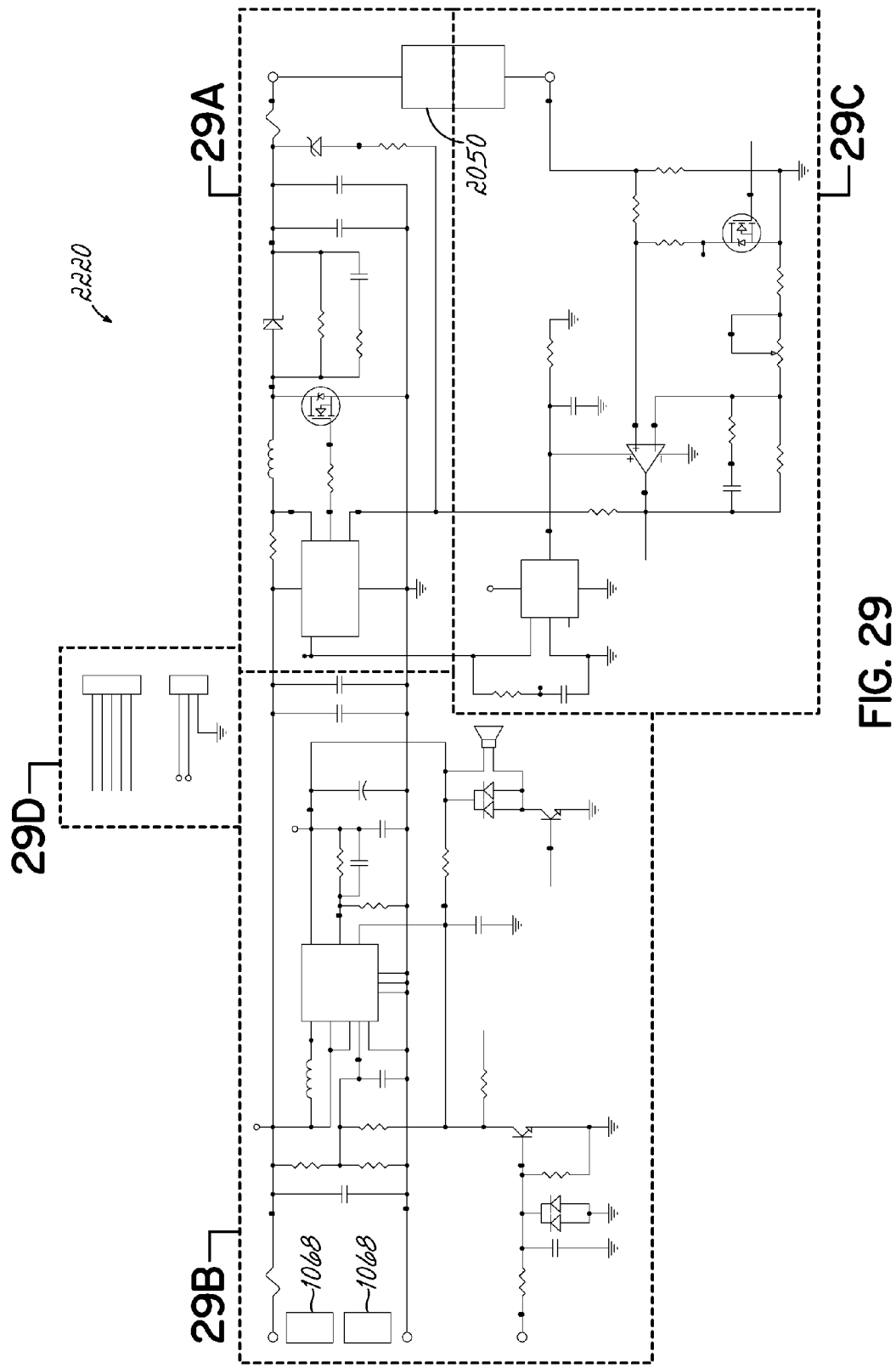
Figure 29A:
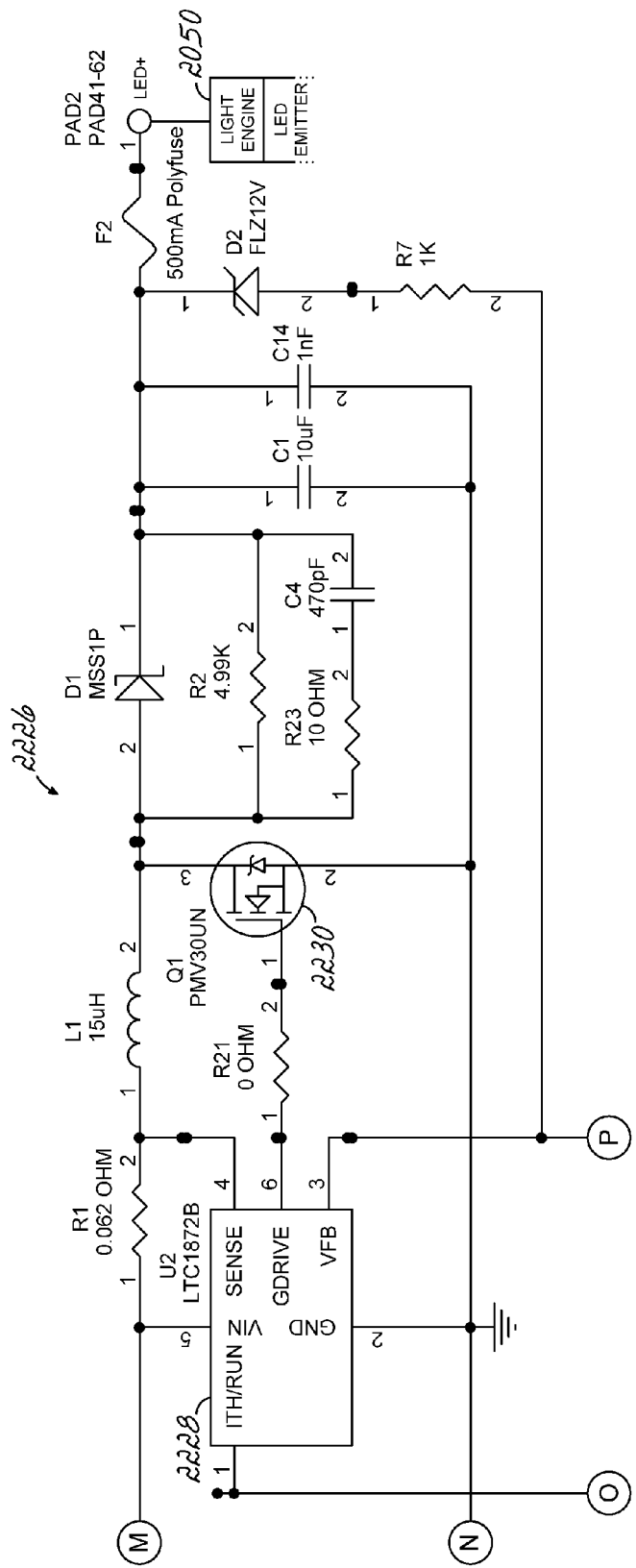
Figure 29B:
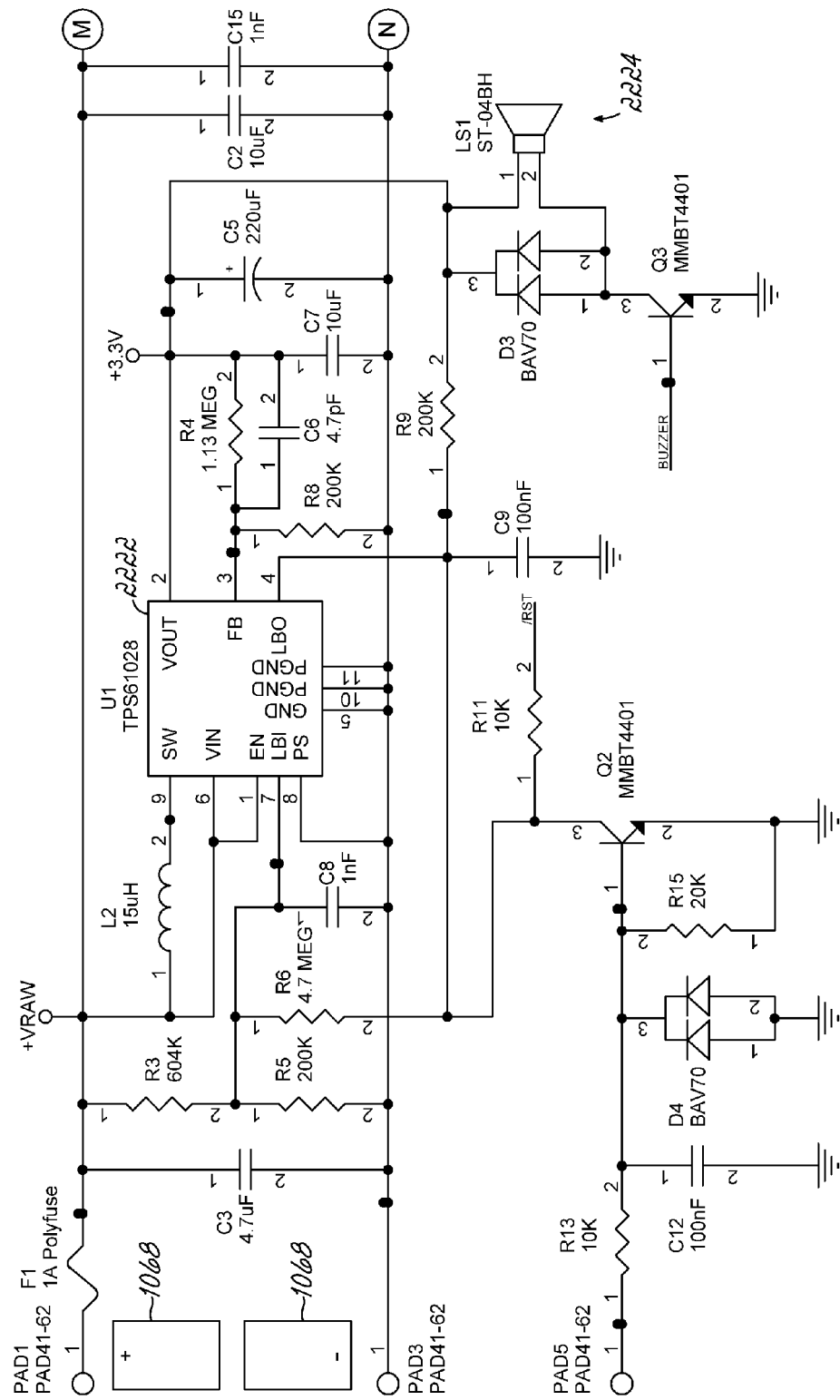
Figure 29C:
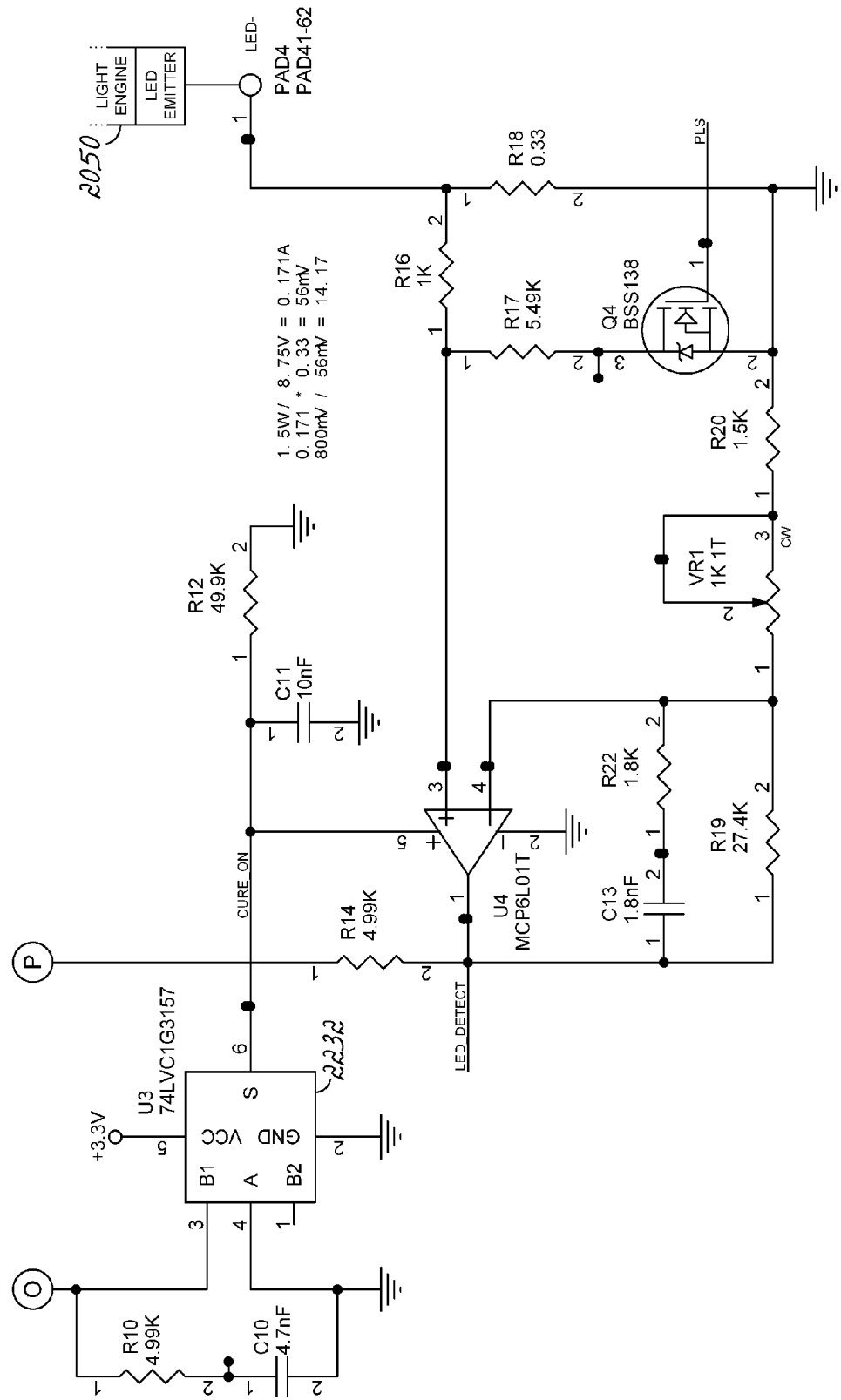

Referring to FIG. 29, a discharge circuit is illustrated in accordance with one embodiment of the invention. Discharge circuit 2220 provides an input section, as illustrated in FIG. 29B, that couples appropriately with ultracapacitors 1068. The ultracapacitors, as illustrated, are discharged in series and generally 5.2 volts DC is provided across the ultracapacitors, which is converted by an appropriate converter circuit component 2222, to around 3.3 volts. The input circuit may also provide an appropriate audio element, such as a buzzer or beeper 2224, for indicating the operation of the light device, such as the completion of a curing cycle. The appropriate control of the discharge is provided through a connector section 29D, which corresponds to the connector section 28C of the main control circuit 2200 (See FIG. 28). The output voltage signal from the input section of FIG. 29B is provided to discharge circuit sections 23A, 23C, which are coupled directly to the light engine LED emitters, as illustrated in FIG. 29. More specifically, the circuit section illustrated in FIG. 29A includes a boost converter circuit 2226 to drive the LED emitters of the light engine. The boost converter circuit 2226 includes an FET driver component 2228, which drives FET 2230. A solid state switch component 2232, as illustrated in FIG. 29C, provides switch control to turn the curing light device ON and OFF.

component 2228, which drives FET 2230. A solid state switch component 2232, as illustrated in FIG. 29C, provides switch control to turn the curing light device ON and OFF.

While the present invention has been illustrated by the description of the embodiments thereof, and while the embodiments have been described in considerable detail, it is not the intention of the Applicant to restrict or in any way limit the scope of the appended claims to such detail. Additional advantages and modifications will readily appear to those skilled in the art. Therefore, the invention in its broader aspects is not limited to the specific details representative apparatus and method, and illustrative examples shown and described. Accordingly, departures may be made from such details without departure from the spirit or scope of Applicant's general inventive concept.

What is claimed is:

1. A curing light device comprising:
a body including a housing and a socket at an end thereof;
a tip having a proximal end and a distal end, the proximal end configured for plugging into the body socket to removably secure the tip with the body;
the tip including a plurality of body elements formed of an electrically and thermally conductive material, the body elements electrically isolated from each other to form separate electrical conductors in the tip and collectively operating to provide thermal conduction of heat in the tip;
a light engine including at least one light emitting element operable for emitting light, the light engine positioned on the distal end of the tip and electrically coupled with the tip body elements to receive power and thermally coupled with the tip body elements for removing heat;
a non-imaging element coupled with the light engine at the distal end of the tip for capturing and collimating the emitted light;
a power supply positioned in the body housing and electrically coupled with electrical contacts in the socket, the tip body elements engaging the socket electrical contacts to conduct electrical enerqy to power the light engine, the power supply being rechargeable and including at least one ultracapacitor element.

2. The curing light device of claim 1 further comprising a magnetic mechanism configured for removably securing the tip in the socket.

3. The curing light device of claim 2 wherein the magnetic mechanism provides a force in the range of 0.5 to 6 pounds for securing the tip in the socket.

4. The curing light device of claim 2 wherein the magnetic mechanism includes a rare earth magnet.

5. The curing light device of claim 1 wherein the tip body elements come together to form the tip and are separated by an insulator element to electrically isolate the body elements.

6. The curing light device of claim 1 wherein the body elements of the tip are operable for drawing heat away from the light engine and the distal end of the tip.

7. The curing light device of claim 1 wherein the power supply further comprises a pair of ultracapacitors.

8. The curing light device of claim 1 wherein the power supply is operable for providing an operational run time of at least one minute.

9. The curing light device of claim 1 wherein the power supply is operable for providing an operational run time of up to 10 minutes.

10. The curing light device of claim 1 wherein power supply is operable for providing an operational run time of approximately 250 seconds.

11. The curing light device of claim 1 wherein the light engine includes three light emitting elements, the light engine operable for providing an output power of 1100-1800 mW/cm².

12. The curing light device of claim 6 wherein the body elements of the tip are configured to draw heat away from the distal end of the tip and prevent a rise in the temperature of the pulp of a tooth being cured greater than 5 degrees Centigrade.

13. The curing light device of claim 1 wherein the tip body elements are configured to form contact structures at the proximal end of the tip, the contact structures engaging the socket electrical contacts to conduct electrical energy.

14. The curing light device of claim 1 wherein at least one of the body elements has a solid portion and a hollowed out portion along the length of the body element.

15. The curing light device of claim 1 wherein the tip has a base that is wider than the proximal end, the proximal end of the tip extending beyond the base for plugging into the body socket.

16. The curing light device of claim 2 wherein the magnetic mechanism includes a magnet coupled with one of the body and the tip and a metal element coupled with the other of the body and the tip for removably securing the tip in the socket.

17. The curing light device of claim 1 further comprising a charger base for receiving the device body to recharge the power supply, the charger base providing a gravity force and including a plug that is configured to be received by a socket in the device body, the plug and socket requiring a removal force to separate the device and charger base that is less than the gravity force of the charger base to facilitate one hand removal of the light device from the charger base.

18. The curing light device of claim 1 wherein the charger base includes a radiometer sensor operable for measuring a light output of the light device.

19. The curing light device of claim 1 wherein the non-imaging element is a non-imaging lens having a frustoconical section.

\* \* \* \* \*